US009717439B2

(12) United States Patent
Giftakis et al.

(10) Patent No.: US 9,717,439 B2
(45) Date of Patent: Aug. 1, 2017

(54) PATIENT DATA DISPLAY

(75) Inventors: Jonathon E. Giftakis, Maple Grove, MN (US); Timothy J. Denison, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 2237 days.

(21) Appl. No.: 12/751,508

(22) Filed: Mar. 31, 2010

(65) Prior Publication Data

US 2011/0245629 A1    Oct. 6, 2011

(51) Int. Cl.
    *A61B 5/0476*     (2006.01)
    *A61B 5/11*     (2006.01)
    *A61B 5/00*     (2006.01)

(52) U.S. Cl.
    CPC .......... *A61B 5/0476* (2013.01); *A61B 5/1116* (2013.01); *A61B 5/4094* (2013.01); *A61B 5/742* (2013.01); *A61B 5/744* (2013.01); *A61B 5/686* (2013.01); *A61B 5/6823* (2013.01); *A61B 5/6828* (2013.01); *A61B 5/6868* (2013.01); *A61B 5/7435* (2013.01); *A61B 2560/0219* (2013.01); *A61B 2562/043* (2013.01)

(58) Field of Classification Search
CPC ....... A61B 5/0476; A61B 5/742; A61B 5/744; A61B 5/4094; A61B 5/1116; A61B 5/7435; A61B 2560/0219; A61B 2562/043; A61B 5/686; A61B 5/6828; A61B 5/6823; A61B 5/6868
USPC ........................................ 600/301, 544, 545
See application file for complete search history.

(56) References Cited

U.S. PATENT DOCUMENTS

| 4,080,653 | A | | 3/1978 | Barnes, Jr. et al. |
| 4,971,061 | A | | 11/1990 | Kageyama et al. |
| 5,224,486 | A | * | 7/1993 | Lerman et al. ............... 600/509 |
| 5,304,206 | A | | 4/1994 | Baker, Jr. et al. |
| 5,978,702 | A | | 11/1999 | Ward et al. |
| 6,248,080 | B1 | | 6/2001 | Miesel et al. |
| 6,360,122 | B1 | | 3/2002 | Fischell et al. |
| 6,361,508 | B1 | | 3/2002 | Johnson et al. |
| 6,366,813 | B1 | | 4/2002 | DiLorenzo |

(Continued)

FOREIGN PATENT DOCUMENTS

| WO | WO 97/42990 | 11/1997 |
| WO | WO 2006/119103 A2 | 11/2006 |

(Continued)

OTHER PUBLICATIONS

PCT International Search Report and Written Opinion dated Jun. 17, 2011.

(Continued)

*Primary Examiner* — Meredith Weare
(74) *Attorney, Agent, or Firm* — Shumaker & Sieffert, P.A.

(57) ABSTRACT

The temporal correlation between a bioelectrical brain signal of a patient and patient motion data, such as a signal indicative of patient motion or a patient posture indicator, is displayed by a display device. In some examples, the patient posture indicator comprises a graphical representation of at least a portion of a body of the patient. In some examples, the temporal correlation between a bioelectrical brain signal, a signal indicative of patient motion, and a signal indicative of cardiac activity of the patient is displayed by the display device.

25 Claims, 15 Drawing Sheets

(56) References Cited

U.S. PATENT DOCUMENTS

| | | |
|---|---|---|
| 6,788,975 B1 | 9/2004 | Whitehurst et al. |
| 7,006,872 B2 | 2/2006 | Gielen et al. |
| 7,167,751 B1 | 1/2007 | Whitehurst et al. |
| 7,385,443 B1 | 6/2008 | Denison |
| 7,395,113 B2 | 7/2008 | Heruth et al. |
| 7,409,373 B2 | 8/2008 | Knagenhjelm |
| 7,447,545 B2 | 11/2008 | Heruth et al. |
| 7,519,431 B2 | 4/2009 | Goetz et al. |
| 7,610,083 B2 | 10/2009 | Drew et al. |
| 2002/0035338 A1* | 3/2002 | Dear et al. ............... 600/544 |
| 2002/0169485 A1 | 11/2002 | Pless et al. |
| 2004/0172089 A1 | 9/2004 | Whitehurst et al. |
| 2005/0107722 A1* | 5/2005 | Ozaki et al. ............... 600/587 |
| 2005/0203366 A1 | 9/2005 | Donoghue et al. |
| 2005/0209644 A1 | 9/2005 | Heruth et al. |
| 2005/0245790 A1 | 11/2005 | Bergfalk et al. |
| 2006/0135877 A1 | 6/2006 | Giftakis et al. |
| 2006/0135881 A1 | 6/2006 | Giftakis et al. |
| 2006/0136006 A1 | 6/2006 | Giftakis et al. |
| 2006/0195144 A1 | 8/2006 | Giftakis et al. |
| 2006/0212093 A1* | 9/2006 | Pless et al. ............... 607/45 |
| 2006/0224067 A1 | 10/2006 | Giftakis |
| 2006/0264777 A1 | 11/2006 | Drew |
| 2007/0027500 A1 | 2/2007 | Maschino et al. |
| 2007/0038137 A1* | 2/2007 | Arand ............... A61B 5/0402 600/509 |
| 2007/0050715 A1 | 3/2007 | Behar |
| 2007/0150026 A1 | 6/2007 | Bourget et al. |
| 2007/0238939 A1 | 10/2007 | Giftakis et al. |
| 2007/0239054 A1 | 10/2007 | Giftakis et al. |
| 2007/0239060 A1 | 10/2007 | Giftakis et al. |
| 2007/0239230 A1 | 10/2007 | Giftakis et al. |
| 2007/0249968 A1 | 10/2007 | Miesel et al. |
| 2007/0255118 A1* | 11/2007 | Miesel et al. ............... 600/300 |
| 2007/0260147 A1 | 11/2007 | Giftakis et al. |
| 2007/0260286 A1 | 11/2007 | Giftakis et al. |
| 2007/0260289 A1 | 11/2007 | Giftakis et al. |
| 2007/0265536 A1 | 11/2007 | Giftakis et al. |
| 2007/0265677 A1 | 11/2007 | Giftakis et al. |
| 2007/0276439 A1 | 11/2007 | Miesel et al. |
| 2008/0033490 A1 | 2/2008 | Giftakis et al. |
| 2008/0071324 A1 | 3/2008 | Miesel et al. |
| 2008/0091090 A1* | 4/2008 | Guillory et al. ............... 600/301 |
| 2008/0146958 A1* | 6/2008 | Guillory et al. ............... 600/544 |
| 2008/0177194 A1 | 7/2008 | Zhang et al. |
| 2008/0194998 A1 | 8/2008 | Holmstrom et al. |
| 2008/0269631 A1 | 10/2008 | Denison et al. |
| 2008/0269812 A1 | 10/2008 | Gerber et al. |
| 2008/0300641 A1 | 12/2008 | Brunekreeft et al. |
| 2008/0319281 A1 | 12/2008 | Aarts |
| 2009/0046056 A1 | 2/2009 | Rosenberg et al. |
| 2009/0062696 A1 | 3/2009 | Nathan et al. |
| 2009/0082640 A1 | 3/2009 | Kovach et al. |
| 2009/0082691 A1 | 3/2009 | Denison et al. |
| 2009/0099467 A1 | 4/2009 | Toren-Herrinton et al. |
| 2009/0099624 A1 | 4/2009 | Kokones et al. |
| 2009/0171168 A1* | 7/2009 | Leyde et al. ............... 600/301 |
| 2010/0010383 A1 | 1/2010 | Skelton et al. |
| 2010/0010584 A1 | 1/2010 | Skelton |
| 2010/0121215 A1* | 5/2010 | Giftakis et al. ............... 600/544 |
| 2010/0228103 A1 | 9/2010 | Schecter |
| 2011/0066044 A1* | 3/2011 | Moon et al. ............... 600/485 |

FOREIGN PATENT DOCUMENTS

| | | |
|---|---|---|
| WO | WO 2006/119103 A3 | 11/2006 |
| WO | WO 2007/034476 A2 | 3/2007 |
| WO | WO 2008/085008 A1 | 7/2008 |
| WO | WO 2008/133626 A1 | 11/2008 |
| WO | 2011034881 A1 | 3/2011 |

OTHER PUBLICATIONS

Tormans et al., "Nocturnal monitoring of pediatric patients with epilepsy based on accelerometers," 3 pgs., Oct. 2007.

"Nocturnal Monitoring of Pediatric Patients with Epilepsy Based on Accelerometers," http://www.mobilab-khk.be/mobilab/Research/BioMed/Projects/epileptic, printed Mar. 31, 2009.

Cuppens et al., "Detection of Nocturnal Epileptic Seizures of Pediatric Patients Using Accelerometers: Preliminary Results," IEEE Benelux EMBS Symposium, 4 pgs., Dec. 6-7, 2007.

Intracranial Pressure, Retrieved from the Internet: URL:web.archive.org/web/20071016060909/http://en.wikipedia.org/wiki/Intracranial_pressure, dated Sep. 28, 2007, retrieved on Oct. 16, 2007 (6 pgs.).

Gabor et al., "Intracranial Pressure During Epileptic Seizures," Electroencephalography and clinical Neurophysiology, 57, pp. 497-506 (Jan. 1984).

Actigraphy to measure day structure as a therapeutic variable in the treatment of schizophrenic patients, Hans-Joachim Haug 1 , Anna Wirz-Justice 2 , Wulf Rössler 1, 1 Psychiatric Department of the University of Zurich and 2 Psychiatric Department of the University of Basel, Switzerland, 1st International Zurich Conference on Clinical and Social Psychiatry, Zurich, Sep. 9-12, 1999. 2000 (5 pgs.).

U.S. Appl. No. 61/113,441, filed Nov. 11, 2008, entitled "Seizure Disorder Evaluation Based on Intracranial Pressure and Patient Motion", by Giftakis et al.

U.S. Appl. No. 12/359,037, filed Jan. 23, 2009, entitled "Seizure Disorder Evaluation Based on Intracranial Pressure and Patient Motion", by Giftakis et al.

U.S. Appl. No. 12/359,055, filed Jan. 23, 2009, entitled "Seizure Disorder Evaluation Based on Intracranial Pressure and Patient Motion", by Giftakis et al.

U.S. Appl. No. 61/174,464, filed Apr. 30, 2009, entitled "Anxiety Disorer Monitoring," by Giftakis et al.

U.S. Appl. No. 61/174,355, filed Apr. 30, 2009, entitled "Machine Learning Technique for Medical Device Programming," by Carlson et al.

U.S. Appl. No. 12/694,042, filed Jan. 26, 2010, entitled "Patient State Detection Based on Support Vector Machine Based Algorithm," by Carlson et al.

U.S. Appl. No. 12/694,053, filed Jan. 26, 2010, entitled "Posture State Detection," by Denison et al.

U.S. Appl. No. 12/694,044, filed Jan. 26, 2010, entitled "Patient State Detection Based on Supervised Machine Learning Based Algorithm," by Carlson et al.

U.S. Appl. No. 12/694,035, filed Jan. 26, 2010, entitled "Patient State Detection Based on Support Vector Machine Based Algorithm," by Carlson et al.

U.S. Appl. No. 61/083,381, filed Jul. 24, 2008, entitled "Frequency Selective Monitoring of Physiological Signals," by Denison et al.

U.S. Appl. No. 61/025,503, filed Feb. 1, 2008, entitled "Frequency Selective Monitoring of Physiological Signals," by Jensen et al.

U.S. Appl. No. 61/975,372, filed Sep. 26, 2007, entitled "Frequency Selective Monitoring of Physiological Signals," by Jensen et al.

U.S. Appl. No. 12/432,268, filed Apr. 29, 2009, entitled "Seizure Detection Algorithm Adjustment," by Giftakis et al.

U.S. Appl. No. 12/751,537, filed Mar. 31, 2010, entitled "Anxiety Disorder Monitoring," by Giftakis et al.

* cited by examiner

PATIENT DATA DISPLAY

TECHNICAL FIELD

The disclosure relates to visualization of information and, more particularly, to a graphical display of patient data.

BACKGROUND

Some neurological disorders, such as epilepsy, are characterized by the occurrence of seizures. Seizures may be attributable to abnormal electrical activity of a group of brain cells. A seizure may occur when the electrical activity of certain regions of the brain, or even the entire brain, becomes abnormally synchronized. The onset of a seizure may be debilitating. For example, the onset of a seizure may result in involuntary changes in body movement, body function, sensation, awareness or behavior (e.g., an altered mental state). In some cases, each seizure may cause some damage to the brain, which may result in progressive loss of brain function over time.

SUMMARY

In general, the disclosure is directed to a graphical user interface that includes patient data useful for evaluating a patient condition. The graphical user interface includes a bioelectrical brain signal of a patient and a patient posture indicator that provides a graphical representation of a posture state of the patient at a particular point in time. The bioelectrical brain signal and the patient posture indicator are displayed such that the temporal correlation is readily ascertained. In this way, the graphical user interface is configured such that the patient posture indicator indicates the patient posture state when a specific portion of the bioelectrical brain signal was observed. In some examples, the graphical user interface includes a plurality of patient posture indicators that each indicates a patient posture state at a different point in time, such that together, patient posture indicators illustrate a time course of patient motion.

In some examples, the graphical user interface also presents a signal indicative of motion of the patient in conjunction with the bioelectrical brain signal and the patient posture indicator (also referred to as "patient posture state indicator"). The patient posture indicator can be generated based on the signal indicative of patient motion. In addition, in some examples, the graphical user interface displays a cardiac signal indicative of cardiac activity of the patient and temporally correlated to the bioelectrical brain signal.

In one example, the disclosure is directed to a method that includes displaying, with a display device, a representation of a bioelectrical brain signal of a patient, and generating and displaying, with the display device, a patient posture indicator that is temporally correlated with a segment of the bioelectrical brain signal, wherein the patient posture indicator comprises a graphical representation of at least a portion of a body of the patient.

In another example, the disclosure is directed to a system that includes a user interface and a processor that displays via the user interface a bioelectrical brain signal of a patient and a patient posture indicator that is temporally correlated with a segment of the bioelectrical brain signal, wherein the patient posture indicator comprises a graphical representation of at least a portion of a body of the patient.

In another example, the disclosure is directed to a system that includes means for displaying a bioelectrical brain signal of a patient, and means for generating and displaying a patient posture indicator that is temporally correlated with a segment of the bioelectrical brain signal, wherein the patient posture indicator comprises a graphical representation of at least a portion of a body of the patient.

In another example, the disclosure is directed to a computer-readable medium that includes instructions that cause a processor to display a bioelectrical brain signal of a patient, and generate and display a patient posture indicator that is temporally correlated with a segment of the bioelectrical brain signal, wherein the patient posture indicator comprises a graphical representation of at least a portion of a body of the patient.

In another aspect, the disclosure is directed to an article of manufacture comprising a computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples are set forth in the accompanying drawings and the description below. Other features, objects, and advantages of the invention will be apparent from the description and drawings, and from the claims.

DETAILED DESCRIPTION

Figure 1:
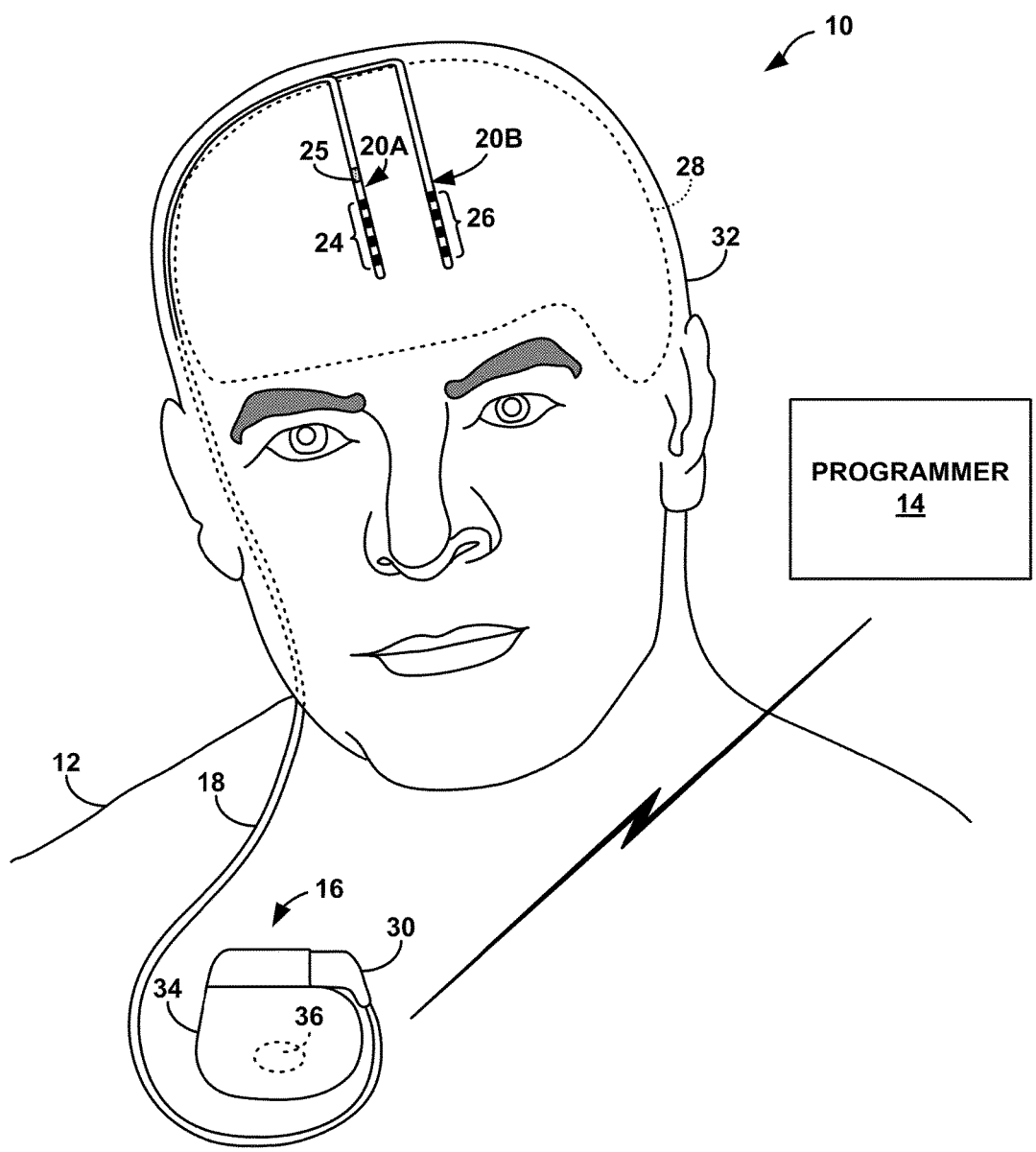
FIG. 1 is a conceptual diagram illustrating an example deep brain stimulation (DBS) system that includes one or more activity sensors that generate a signal indicative of patient activity.

A therapy system may be used to manage a seizure disorder of a patient, e.g., to mitigate the effects of the seizure disorder, shorten the duration of seizures, prevent the onset of seizures or notify a patient about an onset or potential onset of a seizure. For example, attempts to manage seizures have included the delivery of electrical stimulation to regions of the brain via a medical device and/or the delivery of drugs either orally or infused directly into regions of the brain via a medical device. In some electrical stimulation systems, a medical lead is implanted within a patient and coupled to an external or implanted electrical stimulator. The target stimulation site within the brain or elsewhere may differ between patients, and may depend upon the type of seizures being treated by the electrical stimulation system. In some therapy systems, electrical stimulation is continuously delivered to the brain. In other systems, the delivery of electrical stimulation is triggered by the detection or prediction of an event, such as the detection of a seizure based on bioelectrical brain signals sensed within the brain.

In automatic drug delivery systems, a catheter is implanted within a patient and coupled to an external or implanted fluid delivery device. The fluid delivery device may deliver a dose of an anti-seizure drug into the blood stream or into a region of the brain of the patient at regular intervals, upon the detection or prediction of some event, such as the detection of a seizure by electroencephalogram (EEG) or electrocorticogram (ECG) sensors implanted within the brain, or at the direction of the patient or clinician.

In examples described herein, a therapy system includes a display device (e.g., a medical device programmer or a computing device comprising a display) that displays a graphical user interface that presents a representation of a temporal correlation between a bioelectrical brain signal of the patient and motion of the patient. In this way, a graphical user interface can illustrate a patient posture indicator that is temporally associated, within the graphical user interface, with a particular segment of the bioelectrical brain signal. For example, the graphical user interface can include a bioelectrical brain signal of a patient and one or more patient posture indicators that each provides a graphical representation of a posture state of the patient at a respective point in time relative to the bioelectrical brain signal. That is, the posture state indicators can indicate the one or more patient posture states during a time period that overlaps with the time period in which the bioelectrical brain signal was sensed by a sensor.

As used herein, a posture state refers to a patient posture or a combination of posture and activity. For example, some posture states, such as upright, may be sub-categorized as upright and active or upright and inactive. Other posture states, such as lying down posture states, may or may not have an activity component, but regardless may have sub-categories such as lying face up or face down, or lying on the right side or on the left side. A patient posture indicator can be generated based on a signal indicative of motion of the patient. The one or more patient posture indicators can be displayed in the graphical user interface such that the brain activity of the patient (as indicated by the bioelectrical brain signal) and the patient posture state of the patient at the time the brain activity occurred are readily visually ascertained by a user.

The display of the temporal correlation between the bioelectrical brain signal and the patient posture indicator, may allow a user to visually ascertain the physiological activity of a patient during seizures, which can be useful for identifying portions of the bioelectrical brain signal that are relevant to the occurrence of a particular type of seizure. For example, a clinician may monitor and analyze the physiological activity of the patient, e.g., bioelectrical brain activity and patient motor activity, during seizures based on the patient data presented by the graphical user interface. Indeed, differentiating between different types of seizures may be useful for patient monitoring and evaluation, as well as medical device programming.

Monitoring and analyzing the physiological activity of a patient during seizures may provide useful information for various purposes, such as evaluating the patient (e.g., for diagnostic purposes), determining a therapy regimen for the patient, and/or modifying one or more therapy parameter values for the therapy. For example, the ability to view several indicators of physiological activity of a patient during a common time frame may allow the user, e.g., a clinician, to classify one or more seizures as a particular type of seizure based on particular characteristics of the physiological activity. The user may also be able to identify a particular indicator of seizure activity that regularly precedes other indicators, which may facilitate the generation of or modification to a therapy program that effectively manages the seizure disorder of the patient. For example, the user may determine that a particular signal characteristic (e.g., an amplitude or a frequency domain characteristic) of the patient's bioelectrical brain signal regularly precedes a particular type of motor activity of the patient during a seizure, and may modify delivery of therapy or generate a new therapy program based on the correlation.

FIG. 1 is a conceptual diagram illustrating an example therapy system 10 that delivers therapy to manage a seizure disorder (e.g., epilepsy) of patient 12. Patient 12 ordinarily will be a human patient. In some cases, however, therapy system 10 may be applied to other mammalian or non-mammalian, non-human patients. While seizure disorders are primarily referred to herein, in other examples, therapy system 10 may also provide therapy to manage symptoms of other patient conditions in addition to a seizure disorder, such as, but not limited to, psychological disorders, movement disorders, or other neurodegenerative impairments.

Therapy system 10 may be used to manage the seizure disorder of patient 12 by, for example, minimizing the severity of seizures, shortening the duration of seizures, minimizing the frequency of seizures, preventing the onset of seizures, and the like. Therapy system 10 includes medical device programmer 14, implantable medical device (IMD) 16, lead extension 18, and one or more leads 20A and 20B with respective sets of electrodes 24, 26. Selected electrodes 24, 26 may deliver therapy to patient 12 and may also, in some examples, sense bioelectrical brain signals within brain 28 of patient 12.

In addition to delivering therapy to manage a seizure, therapy system 10 may include a sensing module (also referred to as a sensor) that generates a signal indicative of patient motion (e.g., patient posture and/or activity), such as one or more two-axis or three-axis accelerometers, piezoelectric crystals, or pressure transducers. In some examples, a therapy delivery element, such as lead 20A, includes an activity sensor 25 that generates a signal indicative of patient motion. As described in further detail below, therapy system 10 also includes a component that includes a user interface that displays a temporal correlation between data related to bioelectrical brain activity of patient 12 and data related to motor activity of patient 12, and, in some examples, data related to cardiac activity of patient 12. In some examples, the component that includes the user interface is programmer 14. However, in other examples, the component can be a computing device separate from programmer 14.

IMD 16 includes a therapy module that comprises a stimulation generator that generates and delivers electrical stimulation therapy to patient 12 via a subset of electrodes 24 and 26 of leads 20A and 20B, respectively. In the example shown in FIG. 1, electrodes 24, 26 of leads 20A, 20B are positioned to deliver electrical stimulation to a tissue site within brain 28, such as a deep brain site under the dura mater of brain 28 of patient 12. In some examples, delivery of stimulation to one or more regions of brain 28, e.g., an anterior nucleus, thalamus, or cortex of brain 28, may provide an effective treatment to manage a seizure disorder. However, the specific target tissue sites can vary depending on the particular patient 12 for which therapy system 10 is implemented to treat, and the type of seizure disorder afflicting patient 12.

Therapy system 10 includes sensing module that senses bioelectrical signals within brain 28 of patient 12. The bioelectrical brain signals may reflect changes in electrical current produced by the sum of electrical potential differences across brain tissue. Examples of bioelectrical brain signals include, but are not limited to, an EEG signal, an ECoG signal, a local field potential (LFP) sensed from within one or more regions of a patient's brain, and action potentials from single cells within the patient's brain. In addition, in some examples, a bioelectrical brain signal includes a single indicative of the measured impedance of tissue of brain 28 over time. In some examples, IMD 16 includes the sensing module, which senses bioelectrical signals within brain 28 via a subset of electrodes 24, 26. Examples in which IMD 16 comprises senses bioelectrical signals within brain 28 are described herein. However, in other examples, the sensing module that senses bioelectrical signals within brain 28 can be physically separate from IMD 16.

In some examples, IMD 16 detects the onset of a seizure or the possibility of the onset of a seizure based on the bioelectrical brain signal. In some examples, IMD 16 may detect the seizure based on the bioelectrical brain signal prior to a physical manifestation of the seizure. Upon detecting the seizure, IMD 16 may deliver therapy to brain 28 of patient 12 to help mitigate the effects of the seizure or, in some cases, to prevent the onset of the seizure. In this way, the bioelectrical brain signals may be used to control therapy delivery to patient 12. IMD 16 may use, for example, a seizure detection algorithm that may include receiving bioelectrical brain signals sensed within brain 28 of patient 12 via, e.g., electrodes 24, 26, analyzing the signals, and producing an output that triggers the delivery of therapy or generation of a patient alert.

Examples of systems and methods that include adjusting therapy based on seizure detection algorithms are described in commonly-assigned U.S. patent application Publication No. 2010/0121215 by Giftakis, et al., entitled "SEIZURE DETECTION ALGORITHM ADJUSTMENTS," which was filed on Apr. 29, 2009 and is incorporated herein by reference in its entirety. Examples of detecting a bioelectrical brain signal indicative of a seizure are described in U.S. Pat. No. 7,006,872 to Gielen et al., entitled, "CLOSED LOOP NEUROMODULATION FOR SUPPRESSION OF EPILEPTIC ACTIVITY," which issued on Feb. 28, 2006. U.S. Pat. No. 7,006,872 to Gielen et al. is incorporated herein by reference in its entirety. As described in U.S. Pat. No. 7,006,872 to Gielen et al., therapy may be delivered when the EEG data exhibits a certain characteristic indicative of a likelihood of an onset of a seizure.

Another example of a seizure detection algorithm that IMD 16 may implement to detect a seizure is described in commonly-assigned U.S. Patent Application Publication No. 2008/0269631 by Denison et al., which is entitled, "SEIZURE PREDICTION" and was filed on Apr. 30, 2007. U.S. Patent Application Publication No. 2008/0269631 by Denison et al. is incorporated herein by reference in its entirety. In these examples, processor 60 may detect a seizure of patient 12 based on impedance of tissue within brain 28, which may be sensed via any suitable combination of electrodes 24, 26. For example, as described in U.S. Patent Application Publication No. 2008/0269631 by Denison et al., an impedance of brain 28 (FIG. 1) of patient 12 is measured by delivering a stimulation current to brain 28 via implanted electrodes. The stimulation current may be relatively low to prevent inadvertent stimulation of tissue and to prevent patient 12 from feeling the stimulation current. For example, the stimulation current may be in a range of about 500 nanoamps (nA) to about 10 microamps (µA), although other stimulation currents may be used. The stimulation current that is delivered to measure impedance may differ from that used to deliver stimulation therapy to the patient to prevent a seizure from occurring or to mitigate the effects of a seizure. As described in U.S. Patent Application Publication No. 2008/0269631 by Denison et al., examples of frequencies that may be used for the input stimulation current to measure impedance of the brain include, but are not limited to range of about 1 kilohertz (kHz) to about 100 kHz, such as a range of about 4 kHz to about 16 kHz.

In other examples, rather than delivering therapy to brain 28 of patient 12 in a closed-loop manner, e.g., in response to detecting a seizure, IMD 16 can deliver therapy to patient 12 in an open-loop manner. For example, IMD 16 can deliver therapy to patient 12 on a continuous, substantially continuous or periodic basis to help mitigate the effects of the seizure or, in some cases, to prevent the onset of the seizure.

IMD 16 may be implanted within a subcutaneous pocket above the clavicle, or, alternatively, the abdomen, back or buttocks of patient 12, on or within cranium 32 or at any other suitable site within patient 12. Generally, IMD 16 is constructed of a biocompatible material that resists corrosion and degradation from bodily fluids. IMD 16 may comprise a hermetic outer housing 34 or hermetic inner housings within outer housing 34 to substantially enclose components, such as a processor, therapy module, and memory.

Implanted lead extension 18 is coupled to IMD 16 via connector 30. In the example of FIG. 1, lead extension 18 traverses from the implant site of IMD 16 and along the neck of patient 12 to cranium 32 of patient 12 to access brain 28. Lead extension 18 is electrically and mechanically connected to leads 20A, 20B (collectively "leads 20"). In the example shown in FIG. 1, leads 20 are implanted within the right and left hemispheres, respectively, of patient 12 in order to deliver electrical stimulation to one or more regions of brain 28, which may be selected based on the patient condition or disorder controlled by therapy system 10. Other implant sites for leads 20 and IMD 16 are contemplated. For example, IMD 16 may be implanted on or within cranium 32 or leads 20 may be implanted within the same hemisphere or IMD 16 may be coupled to a single lead. Although leads 20 are shown in FIG. 1 as being coupled to a common lead extension 18, in other examples, leads 20 may be coupled to IMD 16 via separate lead extensions or directly connected to connector 30 of IMD 16. In addition, in some examples, therapy system 10 may include more than two leads or one lead.

Leads 20 may be positioned to sense bioelectrical brain signals within a particular region brain 28 to manage patient symptoms associated with a seizure disorder of patient 12. of brain 28 and to deliver electrical stimulation to one or more target tissue sites within Leads 20 may be implanted to position electrodes 24, 26 at desired locations of brain 28 through respective holes in cranium 32. For example, electrodes 24, 26 may be surgically implanted under the dura mater of brain 28 via a burr hole in cranium 32 of patient 12, and electrically coupled to IMD 16 via one or more leads 20.

In the example shown in FIG. 1, electrodes 24, 26 of leads 20 are shown as ring electrodes. Ring electrodes may be useful in deep brain stimulation applications because they are relatively simple to program and are capable of delivering an electrical field to any tissue adjacent to electrodes 24, 26. Similarly, ring electrodes 24, 26 may be useful in sensing bioelectrical brain signals within brain 28 of patient 12 because they may be capable of sensing the signals in any tissue adjacent to electrodes 24, 26. In other examples, electrodes 24, 26 may have different configurations. For example, in some examples, at least some of the electrodes 24, 26 of leads 20 have a complex electrode array geometry that is capable of producing shaped electrical fields. The complex electrode array geometry may include multiple electrodes (e.g., partial ring or segmented electrodes) around the outer perimeter of each lead 20, rather than one ring electrode. In this manner, electrical stimulation may be directed to a specific direction from leads 20 to enhance therapy efficacy and reduce possible adverse side effects from stimulating a large volume of tissue. Similarly, a complex electrode array geometry of sensing electrodes 24, 26 may be capable of sensing changes in bioelectrical brain signals in only a particular portion of brain 28, e.g., the portion of brain 28 proximate to a particular electrode 24, 26. In some examples, housing 34 of IMD 16 includes one or more stimulation and/or sensing electrodes. In alternative examples, leads 20 may have shapes other than elongated cylinders as shown in FIG. 1. For example, leads 20 may be paddle leads, spherical leads, bendable leads, or any other type of shape effective in treating patient 12 and sensing bioelectrical brain signals within brain 28 of patient 12.

Activity sensor 25, which is coupled to lead 20A, generates a signal indicative of patient activity (e.g., patient movement or patient posture transitions). For example, activity sensor 25 may include one or more accelerometers, e.g., one or more micro-electromechanical accelerometers. The one or more accelerometers may include single-axis, two-axis, or three-axis accelerometers, capable of detecting static orientation or vectors in three-dimensions. In other examples, activity sensor 25 may include one or more gyroscopes, pressure transducers, piezoelectric crystals, or other sensors that generate a signal indicative of patient activity.

When activity sensor 25 is positioned within cranium 32, activity sensor 25 may generate an electrical signal indicative of movement of the head of patient 12. For example, in some patients, certain types of seizures may result in a pulling motion of the head. In these examples, activity sensor 25 may be used to detect seizures that include such pulling motion. As another example, activity sensor 25 may generate an electrical signal indicative of convulsive motion of patient 12. For some patients, certain types of seizures (e.g., a tonic-clonic seizure) may result in the patient undergoing involuntary, convulsive movement. The convulsive movement may include, for example, twitching or violent shaking of the arms, legs, and/or head.

Although FIG. 1 illustrates activity sensor 25 located proximal to electrodes 24, 26 on leads 20, in other examples, electrodes 24, 26 and activity sensor 25 may have any suitable arrangement. For example, one or more activity sensors may be located between one or more electrodes 24, 26. As another example, one or more activity sensors may be located distal to one or more electrodes 24, 26. A therapy system may include an activity sensor that is physically separate from leads 20 that deliver therapy to patient 12, and communicates with programmer 14, IMD 16 and/or another device via wireless communication techniques or a wired connection. Moreover, in some examples, one or more activity sensors may be carried by a therapy delivery element other than a lead, such as a catheter that delivers a therapeutic agent to patient 12.

In the example illustrated in FIG. 1, a second activity sensor 36 is located within or on outer housing 34 of IMD 16. As with activity sensor 25, activity sensor 36 generates a signal indicative of patient activity, such as patient motion associated with a seizure or a sudden change in patient posture associated with a seizure, e.g., as a result of a fall. Activity sensor 36 may include, for example, one or more accelerometers, gyroscopes, pressure transducers, piezoelectric crystals, or other sensors that generate a signal that changes as a function of patient activity. In some examples, an accelerometer may be a single or multi-axis accelerometer, e.g., may measure changes in acceleration along one or more axes.

As illustrated in FIG. 1, activity sensor 36 is positioned within a torso of patient 12, which may be a more central location within the body of patient 12 in comparison to the position of activity sensor 25 in cranium 32 of patient 12. In some examples, activity sensor 36 may more accurately indicate seizure-related patient activity because of the relatively central location of activity sensor 36 within the body of patient 12. For example, activity sensor 36 may generate a signal that indicates motion of more than one portion of the body of patient 12, in comparison to activity sensor 25 that, in some examples, may generate a signal that is generally indicative of motion of cranium 32 of patient 12. In addition, activity sensor 36 may be more sensitive to ripple effects generated by muscle tension in the body of patient 12 because of its location within the torso of patient 12. An ability to detect movement of more than one region of the body of patient 12 may be useful for detecting movement that occurs as a result of motor seizures, which are seizures that include a motor component. Because of the central location of activity sensor 36 relative to the limbs (e.g., arms and legs) and head of patient 12, activity sensor 36 may have the ability to more accurately detect movement of multiple parts of the body of patient 12 resulting from a seizure, in comparison to activity sensor 25 in cranium 32.

Activity sensor 36 may be more useful for detecting changes in patient posture than activity sensor 25. Due to the location of sensor 36 within a torso of patient 12, sensor 36 may generate a signal that is more indicative of patient posture than, for example, an activity sensor located within or on an arm, leg, or head of patient 12. In particular, an arm, leg, or head of patient 12 may be bent relative to the torso, such that the position of the arm, leg, or head does not accurately represent the overall posture of patient 12.

In some examples, therapy system 10 includes activity sensor 36 coupled to (e.g., located within or on) housing 34 of IMD 16 and does not include activity sensor 25. However, two or more activity sensors 25, 36 may be useful for determining relative motion between a head of patient 12 and the body of the patient. The relative motion qbetween activity sensors 25, 36 may be detected based on the signals from both activity sensors. In this way, particular patient postures or changes in patient postures may also be discerned based on signals generated by both activity sensors 25 and 36. In some examples, patient activity may also be detected via one or more EMG sensors that generate an electrical signal indicative of muscle movement or one or more intracranial pressure sensors that indicate a change in pressure in cranium 32, which may result from changes in patient posture or a change in patient activity level. Commonly-assigned U.S. patent application Publication No. 2010/0121213 by Giftakis et al., which is entitled, "SEIZURE DISORDER EVALUATION BASED ON INTRACRANIAL PRESSURE AND PATIENT MOTION" and was filed on Jan. 23, 2009, and U.S. patent application Publication No. 2010/0121214 by Giftakis et al., which is entitled, "SEIZURE DISORDER EVALUATION BASED ON INTRACRANIAL PRESSURE AND PATIENT MOTION" and was filed on Jan. 23, 2009 describe ways in which intracranial pressure information may be useful for detecting patient posture transitions. U.S. patent application Publication Nos. 2010/0121213 and 2010/0121214 are incorporated herein by reference in their entireties.

Figure 14:
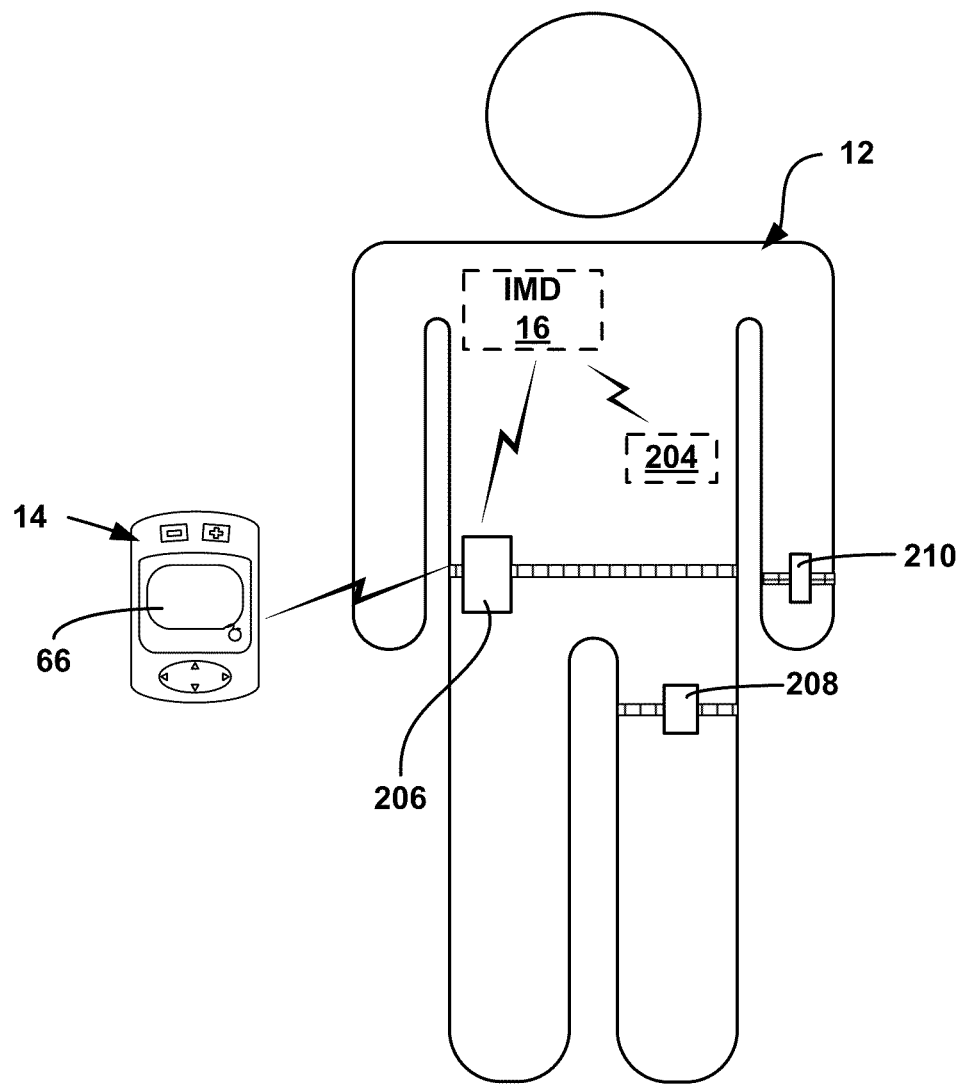
FIG. 14 is a diagram illustrating a therapy system that includes additional activity sensors.

Although FIG. 1 illustrates an example of therapy system 10 that includes two activity sensors 25, 36, in other examples, a therapy system may include any suitable number of activity sensors, e.g., one or more activity sensors. For example, in other examples, therapy system 10 may include an activity sensor other than or in addition to activity sensors 25, 36. In some examples, therapy system 10 may include an activity sensor carried by a lead that is a separate from leads 20 and electrically connected to IMD 16, or an activity sensor that is physically separate from leads 20 and IMD 16, such as an activity sensor that is enclosed in a separate outer housing that is implanted within patient 12 or external to patient 12. In examples in which an activity sensor is not implanted within patient 12, the activity sensor may be coupled to patient 12 at any suitable location and via any suitable technique. For example, an accelerometer may be coupled to a leg, torso, wrist, or head of patient 12, e.g., as illustrated in FIG. 14.

In some examples, IMD 16 senses bioelectrical brain signals continuously, e.g., at all times. In other examples, IMD 16 may sense bioelectrical brain signals intermittently. For example, IMD 16 may sense bioelectrical brain signals during selected periods of time in which activity sensor 25 and/or activity sensor 36 senses a signal indicative of a particular motion of patient 12, e.g., a syncope event.

Electrical stimulation generated by IMD 16 may be configured to manage a variety of disorders and conditions. In some examples, the stimulation generator of IMD 16 is configured to generate and deliver electrical pulses to patient 12 via electrodes of a selected subset of electrodes 24, 26 (referred to as an "electrode combination"). However, in other examples, the stimulation generator of IMD 16 may be configured to generate and deliver a continuous wave signal, e.g., a sine wave or triangle wave. In either case, a signal generator within IMD 16 may generate the electrical stimulation therapy for DBS according to a therapy program that is selected at that given time in therapy. In examples in which IMD 16 delivers electrical stimulation in the form of stimulation pulses, a therapy program may define values for a set of therapy parameters, such as a stimulation electrode combination for delivering stimulation to patient 12, pulse frequency, pulse width, and a current or voltage amplitude of the pulses. A stimulation electrode combination may indicate the specific electrodes 24, 26 that are selected to deliver stimulation signals to tissue of patient 12 and the respective polarities of the selected electrodes.

In the example shown in FIG. 1, IMD 16 includes a memory. The memory may, in some examples, store a plurality of therapy programs that each defines a set of therapy parameter values. In some examples, IMD 16 may select a therapy program from the memory based on various parameters, such as based on one or more characteristics of a bioelectrical brain signal, based on the time of day, based on a posture of patient 12, and the like. IMD 16 may generate electrical stimulation according to the therapy parameter values defined by the selected therapy program to manage the patient symptoms associated with a seizure disorder.

During a trial stage in which IMD 16 is evaluated to determine whether IMD 16 provides efficacious therapy to patient 12, a plurality of therapy programs may be tested and evaluated for efficacy. Therapy programs may be selected for storage within IMD 16 based on the results of the trial stage. During chronic therapy in which IMD 16 is implanted within patient 12 for delivery of therapy on a non-temporary basis, IMD 16 may generate and deliver stimulation signals to patient 12 according to different therapy programs. In addition, in some examples, patient 12 may modify the value of one or more therapy parameter values within a single given program or switch between programs in order to alter the efficacy of the therapy as perceived by patient 12 with the aid of programmer 14. IMD 16 may store instructions defining the extent to which patient 12 may adjust therapy parameters, switch between programs, or undertake other therapy adjustments. Patient 12 may generate additional programs for use by IMD 16 via external programmer 14 at any time during therapy or as designated by the clinician.

External programmer 14 wirelessly communicates with IMD 16 to retrieve information related to data sensed by electrodes 24, 26 and activity sensors 25, 36. Additionally, external programmer 14 may wirelessly communicate with IMD 16 to provide or retrieve information related to delivery of therapy to patient 12. Programmer 14 is an external computing device that a user, e.g., a clinician and/or patient 12, may use to communicate with IMD 16. For example, programmer 14 may be a clinician programmer that a clinician uses to communicate with IMD 16 in order to program one or more therapy programs for IMD 16. Alternatively, programmer 14 may be a patient programmer that allows patient 12 to select programs and/or view and modify therapy parameters. The clinician programmer may include more programming features than the patient programmer. In other words, more complex or sensitive tasks may only be allowed by the clinician programmer to prevent an untrained patient from making undesired changes to IMD 16.

In the examples described herein, programmer 14 also includes a user interface that includes a display that presents a graphical user interface that includes information indicating a temporal correlation between a bioelectrical brain signal and patient motion information. The bioelectrical brain signal can be, for example, a signal generated by a sensing module of IMD 16 or a sensing module physically separate from IMD 16. In some examples described herein, the patient motion information is provided by at least one patient posture indicator that provides a graphical representation of a posture of patient 12, whereby the posture can be determined based on a signal indicative of patient motion. In other examples, graphical user interface presents both the at least one patient posture indicator and the signal indicative of patient motion. The signal indicative of patient motion can be, for example, a signal generated by one or both activity sensors 25, 36 and/or a signal generated by an activity sensor separate from IMD 16 and leads 20 (e.g., implanted or external to patient 12).

In some examples, the patient posture indicator indicates the posture state of patient 12 at discrete points in time. A plurality of displayed patient posture indicators generated based on consecutive segments of a signal indicative of patient motion can provide a user (e.g., a clinician) with a graphical display that indicates the patient motion that is temporally correlated with the displayed bioelectrical brain signal and a signal indicative of patient motion. The plurality of displayed patient posture indicators that each indicates a patient posture state at a different point in time can illustrate a time course of patient motion, e.g., an animation of the patient movement over time.

A posture state can be the posture of patient 12 at a particular point in time. Example posture states include, but are not limited to, sitting, prone, recumbent, and upright. Other examples of posture states include upright, lying back (e.g., when patient 12 is reclining back in a dorsal direction), lying front (e.g., when patient 12 is lying chest down), lying left (e.g., when patient 12 is lying on a left side of the body), and lying right (e.g., when patient 12 is lying on a right side of the body). In addition, in some examples, the posture state of patient 12 can include an activity component. For example, therapy system 10 can be configured to distinguish between an upright and inactive posture state (e.g., when patient 12 is standing still), and an upright and active posture state (e.g., when patient is walking).

Although the examples described herein primarily refer to displaying information relating to bioelectrical brain signals of patient 12 and the motion of patient 12 on a user interface into programmer 14, in other examples, another suitable device, e.g., a computer separate from programmer 14, may include the user interface.

As used herein, a temporal correlation between the bioelectrical brain signal, the one or more patient posture indicators, the signal indicative of patient motion, and any other signal or information, refers to the relationship between the signals in time, e.g., the relationship between the signals in terms of the time period in which the signals were sensed. As an example, the bioelectrical brain signal and a patient posture indicator may be displayed on the user interface such that the patient posture indicator that indicates the patient posture state during a particular time period is substantially aligned with, e.g., directly above or below, the corresponding portion of the bioelectrical brain signal, e.g., the portion of the signal that was sensed during the same time period. As another example, if the bioelectrical brain signal and the signal indicative of patient motion are displayed, the signals may be aligned on the user interface such that a bioelectrical brain signal sensed in a particular time period is displayed parallel to, e.g., directly above or below, the corresponding patient motion signal sensed at substantially the same time.

A patient posture indicator that is temporally correlated to at least one of the bioelectrical brain signal, the signal indicative of patient motion, and any other signal, refers to a patient posture indicator that indicates the patient posture state of patient 12 for a certain time period during which the signal was observed. For example, a patient posture indicator can be temporally correlated to a discrete segment of a bioelectrical brain signal or a signal indicative of patient motion, where the segment can have any suitable duration (e.g., less than one second to about one minute or more). The patient posture indicator can be generated based on the patient posture state indicated by the discrete segment of the signal indicative of patient motion or indicated by a portion of the signal indicative of patient motion that was observed at substantially same time as the discrete segment of a bioelectrical brain signal or other signal to which the patient posture indicator is temporally correlated.

Programmer 14 may be configured to receive data indicative of bioelectrical brain activity of patient 12 and data indicative of motion of patient 12. For example, programmer 14 can receive the raw bioelectrical brain signal from IMD 16 (or another sensing module), a parameterized bioelectrical brain signal or data generated based on the raw bioelectrical brain signal. As another example, programmer 14 can receive the raw patient motion signal from one or both motion sensors 25, 36 (or another motion sensor), a parameterized patient motion signal or data generated based on the raw patient motion signal.

As described in further detail below, e.g., with reference to FIGS. 4A, 4B, and 5, in some examples, programmer 14 displays a received bioelectrical brain signal and patient posture information on a display of a user interface. In some examples, programmer 14 or another device may convert one or both the bioelectrical brain signal or the signal indicative of patient motion into a more intuitive graphical representation of the signal data and, alternatively or additionally, display the graphical representation. For example, instead of or in addition to generating and directly displaying a read-out of data acquired by one or both motion sensors 25, 36 (which can include, for example, signals indicating acceleration in each of the x-axis, y-axis, and/or z-axis directions), a processor within IMD 16, programmer 14, or another device may convert the accelerometer data into a graphical representation of at least a portion of the body of patient 12 that represents the posture of patient 12 at a particular point in time and programmer 14 may display the graphical representation of the body of patient 12 to a user via the user interface. The graphical representation that represents the posture of patient 12 is referred to herein as a patient posture indicator. In some examples, such as the examples shown in the figures, the patient posture indicator is a stick figure. However, other, more complex types of graphical representations of a posture state of patient are also contemplated, such as more realistic human figures.

In some examples described herein, the user interface of programmer 14 displays both the bioelectrical brain signal and one or more patient posture indicators in a manner that illustrates a temporal correlation between the bioelectrical brain signal and the patient posture indicators. In this way, the graphical user interface presented by programmer 14 may allow a user, e.g., a clinician, to view information related to electrographic activity that occurred within brain 28 of patient 12 and information related to the physical posture of patient 12 that occurred during substantially the same period of time. The one or more displayed patient posture indicator can provide a relatively easy to understand indication of the patient posture state, compared to, e.g., the raw signal generated by a motion sensor 25, 36. In some examples, this feature may allow a clinician to identify characteristics of the bioelectrical brain signal that occur substantially simultaneously, e.g., at substantially the same time point, with a particular motor activity (e.g., a fall) during a seizure event.

In some examples described herein, the user interface of programmer 14 also displays both the signal indicative of patient motion and the bioelectrical brain signal in a manner that illustrates a temporal correlation between the signals. In some examples, this feature may allow a clinician to identify characteristics of the bioelectrical brain signal and the signal indicative of patient motion that occur substantially simultaneously, e.g., at substantially the same time point, during a seizure event.

Additionally, the clinician may, in some examples, be able to identify a characteristic of the bioelectrical brain signal that regularly occurs before and/or after a particular patient motor event (e.g., a fall or another abrupt change in posture state) during or related to a seizure event. For example, in some examples, a clinician may determine that a particular characteristic of the bioelectrical brain signal regularly precedes a particular change in posture during a seizure event, e.g., abnormal activity within the bioelectrical brain signal regularly precedes a physical manifestation of the seizure such as a fall or syncope event. The clinician can readily determine the physical manifestation of the seizure based on the patient posture indicator temporally correlated with the abnormal bioelectrical brain signal activity. That is, the patient posture indicator provides a graphical representation of the patient posture state, which can eliminate the need for the clinician or other user to interpret a signal generated by motion sensor 25 or 36 in order to determine the patient posture state.

In examples in which both the bioelectrical brain signal and the signal indicative of patient motion are displayed, a user can determine that a particular characteristic of the bioelectrical brain signal regularly precedes a particular characteristic of the signal indicative of patient motion during a seizure event, e.g., abnormal activity within the bioelectrical brain signal regularly precedes a physical manifestation of the seizure such as a fall or syncope event.

The identification of the characteristic of one signal that regularly occurs before and/or after a particular motor activity of patient 12 during or after a seizure event can be useful for various purposes. The identified characteristic of the bioelectrical brain signal that occurred before a particular motor activity of patient 12 during or after a seizure event can indicate the bioelectrical brain signal characteristic that is indicative of a particular type of seizure, such as a motor seizure. The clinician can then program IMD 16 to automatically detect certain types of seizures, and, in some examples, take some action. For example, the bioelectrical brain signal characteristic can be stored in memory 42 of IMD 16 and processor 40 can control stimulation generator 44 upon detecting the stored bioelectrical brain signal characteristic. For example, the clinician may, in response to identifying a temporal relationship between a patient fall (as indicated by one or more patient posture indicators or even two or more patient posture indicators) and a bioelectrical brain signal characteristic, modify therapy delivery to patient 12 such that IMD 16 automatically initiates or adjusts therapy delivery upon detection of the characteristic of the bioelectrical brain signal in order to prevent or minimize the effects of the physical manifestation of the seizure. In this way, the graphical user interface that presents both the bioelectrical brain signal and corresponding patient posture indicators can be useful for programming IMD 16 to automatically detect certain types of seizures, and, in some examples, take some action.

In some examples, identification of one or more characteristics of a bioelectrical brain signal that regularly occurs before and/or after a particular motor activity of patient 12 during or after a seizure event can be useful for generating a seizure detection algorithm that processor 40 of programmer 14 implements to detect a seizure. For example, one or more characteristics of the bioelectrical brain signal identified via the graphical user interface provided by programmer 14 can be used to train a support vector machine or another type of supervised machine learning algorithm (e.g., any genetic algorithm or artificial neural network). Supervised machine learning is implemented to generate a classification boundary during a learning phase based on training data, e.g., values of two or more features (e.g., the identified characteristics of the bioelectrical brain signal) of one or more patient parameter signals known to be indicative of the patient being in the patient state and feature values of one or more patient parameter signals known to be indicative of the patient not being in the patient state. In some examples, the patient state can be a general seizure state and/or a seizure state for a specific type of seizure.

A feature is a characteristic of the bioelectrical brain signal, such as an amplitude or an energy level in a specific frequency band. The classification boundary delineates the feature values indicative of the patient being in the patient state and feature values indicative of the patient not being in the patient state. In this way, the classification boundary is used to predict or detect the occurrence of the patient state or evaluate the patient state. The patient state detection may be used to control various courses of action, such as controlling therapy delivery, generating a patient notification or evaluating a patient condition. The use of the graphical user interface in training a support vector machine or another type of supervised machine learning algorithm is discussed in further detail below with respect to FIG. 9.

Additional details regarding support vector machine-based algorithms are described in U.S. patent application Ser. No. 12/694,042 by Carlson et al., which is entitled, "PATIENT STATE DETECTION BASED ON SUPPORT VECTOR MACHINE BASED ALGORITHM," and was filed on Jan. 26, 2010, U.S. patent application Ser. No. 12/694,053 by Denison et al., which is entitled, "POSTURE STATE DETECTION," and was filed on Jan. 26, 2010, U.S. patent application Ser. No. 12/694,044 by Carlson et al., which is entitled, "PATIENT STATE DETECTION BASED ON SUPERVISED MACHINE LEARNING BASED ALGORITHM," and was filed on Jan. 26, 2010, and U.S. patent application Ser. No. 12/694,035 by Carlson et al., which is entitled, "PATIENT STATE DETECTION BASED ON SUPPORT VECTOR MACHINE BASED ALGORITHM," and was filed on Jan. 26, 2010. U.S. patent application Ser. Nos. 12/694,042, 12/694,053, 12/694,044, and 12/694,035 are hereby incorporated by reference in their entireties.

In other examples, the identification of the characteristic of one signal that regularly occurs before and/or after a particular motor activity of patient 12 during or after a seizure event can be useful for diagnosing the type or severity of the seizure disorder with which patient 12 is afflicted based on motor activity associated with a seizure detected based on the bioelectrical brain signal. While the clinician may be able to ascertain that a seizure occurred based on the bioelectrical brain signal, the clinician may not be able to readily determine the types of seizures or the severity of the seizures. For example, when presented with just the bioelectrical brain signal of patient 12, the clinician may not be able to readily identify what portions of the signal indicate a particular patient motor activity. In addition, when presented with just the bioelectrical brain signal of patient 12 and a signal indicative of patient motion, the clinician may not be able to readily identify what portions of the signal indicative of patient motion indicate a particular patient motor activity. However, the patient posture indicators generated and displayed by programmer 14 can translate the signal indicative of patient motion into a more intuitive graphical representation of the patient posture state. Based on a change in the posture state of patient 12 indicated by the patient posture indicators, the clinician can diagnose the types of seizures that occur, which can indicate the type or severity of the seizure disorder with which patient 12 is afflicted.

In some examples, programmer 14 can generate and display a graphical user interface that allows a user to review the bioelectrical brain signal information and the patient motion information that were sensed during a particular period of time selected by the user. In other examples, the user interface may allow a user to review bioelectrical brain signal information and patient motion information that include particular characteristics of interest, e.g., characteristics indicative of a particular patient motion such as a fall. Additionally, in some examples, therapy system 10 may include a feature that allows a user to classify a seizure as a particular type of seizure based on analyzing the bioelectrical brain signal and the signal indicative of patient motion via the user interface.

Programmer 14 may be a handheld computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of leads 20, the arrangement of electrodes 24, 26 on leads 20, the number and location of activity sensors 25, 36 within or on patient 12, the position of leads 20 within brain 28, the configuration of electrode array 24, 26, initial programs defining therapy parameter values, and any other information the clinician desires to program into IMD 16. Programmer 14 may also be capable of completing functional tests (e.g., measuring the impedance of electrodes 24, 26 of leads 20).

The clinician may also store therapy programs within IMD 16 with the aid of programmer 14. During a programming session, the clinician may determine one or more therapy programs that provide efficacious therapy to patient 12 to address symptoms associated with the seizure disorder. For example, the clinician may select one or more electrode combinations with which stimulation is delivered to brain 28. During the programming session, patient 12 may provide feedback to the clinician as to the efficacy of the specific program being evaluated or the clinician may evaluate the efficacy based on one or more physiological parameters of patient (e.g., heart rate, respiratory rate, or muscle activity). Programmer 14 may assist the clinician in the creation/identification of therapy programs by providing a methodical system for identifying potentially beneficial therapy parameter values.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain therapy parameters or set an available range of values for a particular therapy parameter.

Programmer 14 may also provide an indication to patient 12 when therapy is being delivered, when patient input has triggered a change in therapy or when the power source within programmer 14 or IMD 16 needs to be replaced or recharged. For example, programmer 14 may include an alert LED, may flash a message to patient 12 via a programmer display, generate an audible sound or somatosensory cue to confirm patient input was received, e.g., to indicate a patient state or to manually modify a therapy parameter. In addition, in examples in which IMD 16 or programmer 14 can automatically detect a seizure, e.g., using a seizure detection algorithm, programmer 14 may provide a notification to patient 12, a caregiver, and/or a clinician when a seizure is detected by IMD 16. A notification of a likelihood of a seizure may provide patient 12 with sufficient notice to, for example, prepare for the onset of the seizure (e.g., by stopping a vehicle if patient 12 is driving the vehicle).

Programmer 14 is configured to communicate with IMD 16 and, optionally, another computing device, via wireless communication. For example, IMD 16 may generate and wirelessly transmit bioelectrical brain signals and signals indicative of motion of patient 12 to programmer 14 for display on the user interface of programmer 14. Programmer 14 may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth (R) specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator, within patient 12 for relatively long-term treatment.

In addition to or instead of electrical stimulation therapy, IMD 16 may deliver a therapeutic agent to patient 12 to manage a seizure disorder. In such examples, IMD 16 may include a fluid pump or another device that delivers a therapeutic agent in some metered or other desired flow dosage to the therapy site within patient 12 from a reservoir within IMD 16 via a catheter. IMD 16 may deliver the therapeutic agent upon detecting a seizure with a seizure detection algorithm that detects the seizure based on bioelectrical brain signals or another patient parameter. The catheter used to deliver the therapeutic agent to patient 12 may include one or more electrodes for sensing bioelectrical brain signals of patient 12.

Examples of therapeutic agents that IMD 16 may deliver to patient 12 to manage a seizure disorder include, but are not limited to, lorazepam, carbamazepine, oxcarbazepine, valproate, divalproex sodium, acetazolamide, diazepam, phenytoin, phenytoin sodium, felbamate, tiagabine, levetiracetam, clonazepam, lamotrigine, primidone, gabapentin, phenobarbital, topiramate, clorazepate, ethosuximide, and zonisamide. Other therapeutic agents may also provide effective therapy to manage the patient's seizure disorder, e.g., by minimizing the severity, duration, and/or frequency of the patient's seizures. In other examples, IMD 16 may deliver a therapeutic agent to tissue sites within patient 12 other than brain 28.

The remainder of the disclosure describes various systems, devices, and techniques for displaying a temporal correlation between a bioelectrical brain signal of a patient and patient motion information, such as one or more successive patient posture indicators and/or a signal indicative of motion of the patient, for monitoring and treating a seizure disorder of a patient.

Figure 2:
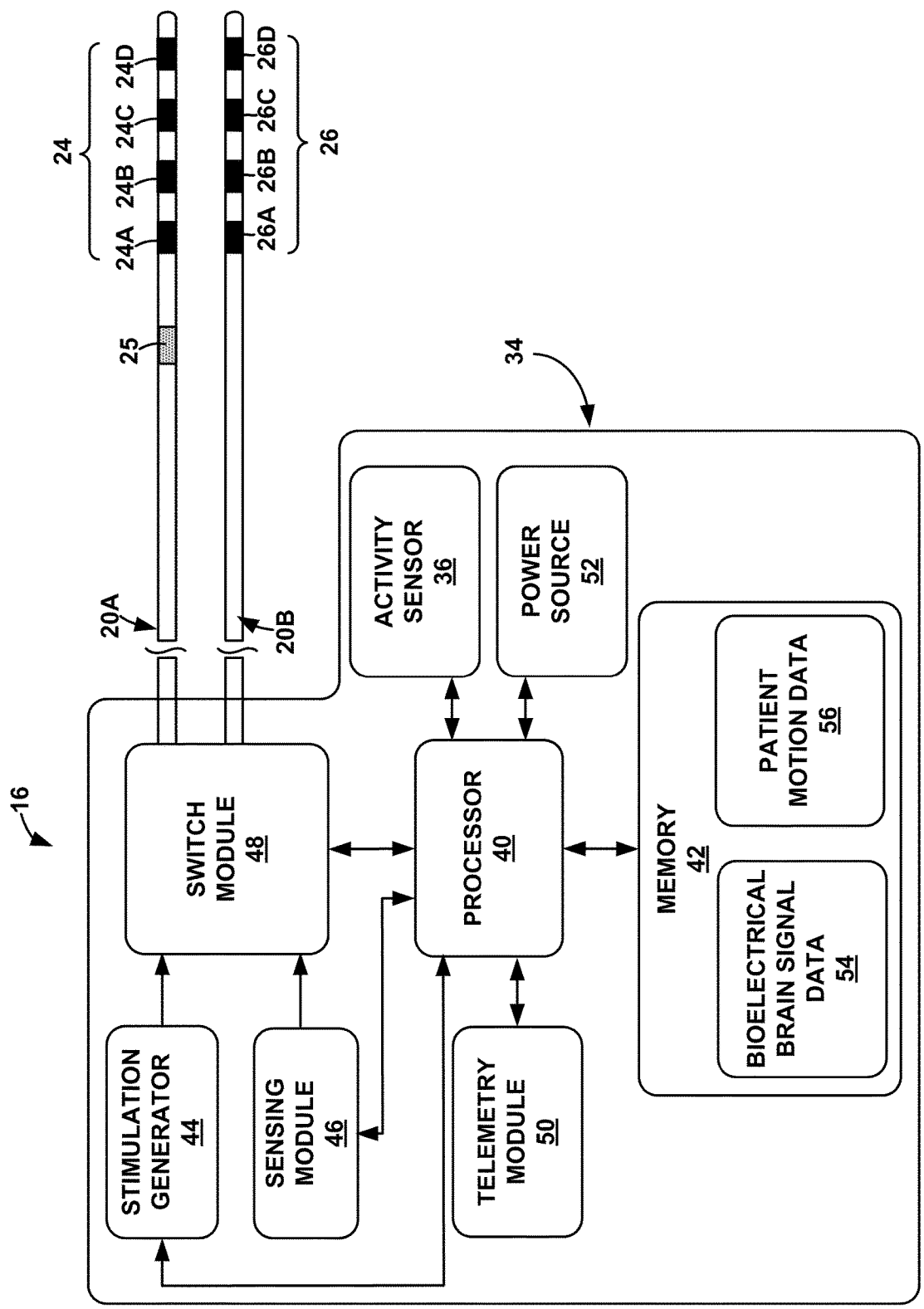
FIG. 2 is functional block diagram illustrating components of an example medical device.

FIG. 2 is a functional block diagram illustrating components of an example IMD 16. In the example shown in FIG. 2, IMD 16 includes activity sensor 25, activity sensor 36, processor 40, memory 42, stimulation generator 44, sensing module 46, switch module 48, telemetry module 50, and power source 52. Processor 40 may include any one or more microprocessors, controllers, digital signal processors (DSPs), application specific integrated circuits (ASICs), field-programmable gate arrays (FPGAs), and discrete logic circuitry. The functions attributed to processors described herein, including processor 40, may be provided by a hardware device and embodied as software, firmware, hardware, or any combination thereof.

In the example shown in FIG. 2, sensing module 46 senses bioelectrical brain signals of patient 12 via select combinations of electrodes 24, 26. Sensing module 46 may include circuitry that measures the electrical activity of a particular region, e.g., an anterior nucleus, thalamus or cortex of brain 28 via select electrodes 24, 26. Sensing module 46 may acquire the bioelectrical brain signal substantially continuously or at regular intervals, such as, but not limited to, a frequency of about 1 Hz to about 1000 Hz, such as about 250 Hz to about 1000 Hz or about 500 Hz to about 1000 Hz. Sensing module 46 includes circuitry for determining a voltage difference between two electrodes 24, 26, which generally indicates the electrical activity within the particular region of brain 28. One of the electrodes 24, 26 may act as a reference electrode, and, if sensing module 46 is implanted within patient 12, a housing of IMD 16 or the sensing module in examples in which sensing module 46 is separate from IMD 16, may include one or more electrodes that may be used to sense bioelectrical brain signals.

The output of sensing module 46 may be received by processor 40. In some cases, processor 40 may apply additional processing to the bioelectrical signals, e.g., convert the output to digital values for processing and/or amplify the bioelectrical brain signal. In addition, in some examples, sensing module 46 or processor 40 may filter the signal from the selected electrodes 24, 26 in order to remove undesirable artifacts from the signal, such as noise from electrocardiogram signals generated within the body of patient 12. Although sensing module 46 is incorporated into a common outer housing 34 with stimulation generator 44 and processor 40 in FIG. 2, in other examples, sensing module 46 is in a separate outer housing from outer housing 34 of IMD 16 and communicates with processor 40 via wired or wireless communication techniques. In other examples, a bioelectrical brain signal may be sensed via external electrodes (e.g., scalp electrodes).

Activity sensors 25, 36, which may also be referred to as motion sensors or posture sensors, each generate a signal indicative of patient activity, which may include patient movement and patient posture. The activity signals generated by sensors 25, 36 independently indicate patient activity. As previously indicated, activity sensors 25, 36 each include one or more accelerometers (e.g., single-axis or multiple-axis accelerometers), gyroscopes, pressure transducers, piezoelectric crystals, or other sensors that generate a signal indicative of patient movement. Processor 40 receives the signals generated by activity sensors 25, 36.

As previously indicated, in some examples, IMD 16 does not include activity sensor 25, while in other examples, IMD 16 does not include activity sensor 36. For ease of description, IMD 16 including activity sensor 36 and not including activity sensor 25 is referenced throughout the remainder of the description.

Processor 40 receives the signals generated by selected electrodes 24, 26 that sense bioelectrical brain signals. In addition, processor 40 receives the signals generated by activity sensor 36 indicative of patient motion. In some examples, processor 40 may store the sensed bioelectrical brain signals and the sensed patient motion signals within memory 42. Processor 40 may also generate time markers (e.g., a timestamp) to the sensed bioelectrical brain signal data and the patient motion signal stored by memory 42. For example, processor 40 may attach a label to each data point indicating the time at which the data point was sensed.

Memory 42 may include any volatile or non-volatile media, such as a random access memory (RAM), read only memory (ROM), non-volatile RAM (NVRAM), electrically erasable programmable ROM (EEPROM), flash memory, and the like. Memory 42 may store computer-readable instructions that, when executed by processor 40, cause IMD 16 to perform various functions described herein. In the example shown in FIG. 2, memory 42 stores bioelectrical brain signal data 54 and patient motion data 56 in separate memories within memory 42 or separate areas within memory 42.

Within bioelectrical brain signal data module 54 of memory 42, processor 40 can store raw bioelectrical brain signals, parameterized bioelectrical brain signals or data generated based on the raw bioelectrical brain signal and a plurality of timestamps that each indicates the time at which a respective data point or data segment was generated by sensing module 46. In some examples, processor 40 continuously, substantially continuously or periodically stores bioelectrical brain signal data 54, e.g., on a regular basis, or in response to a particular event (e.g., the detection of a seizure, a fall or another motor activity). In some examples, the bioelectrical brain signal generated by sensing module 46 can be stored in a loop recorder such that the portions of the signal sensed before the event can also be retrieved. An example loop recording technique is described in commonly assigned U.S. Pat. No. 7,610,083 by Drew et al., which is entitled, "METHOD AND SYSTEM FOR LOOP RECORDING WITH OVERLAPPING EVENTS" and issued on Oct. 27, 2009. U.S. Pat. No. 7,610,083 is incorporated herein by reference in its entirety. Other memory formats are also contemplated.

Within patient motion data module 56 of memory 42, processor 40 can store raw patient motion signals generated by activity sensor 36, parameterized patient motion signals or data generated based on the raw patient motion signals and a plurality of timestamps that each indicates the time at which a respective data point or data segment was generated by activity sensor 36. Processor 40 can continuously, substantially continuously or periodically store patient motion data 56, e.g., on a regular basis, or in response to a particular event (e.g., the detection of a seizure, a fall or another motor activity). In this way, processor 40 can determine that a physiological event such as a seizure has occurred, e.g., using a seizure detection algorithm, and may selectively store data related to bioelectrical brain signals and patient motion along with the corresponding temporal data occurring during the detected physiological event, e.g., processor 40 may store only data that includes characteristics of a seizure event.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 40 controls switch module 48 to sense bioelectrical brain signals with selected combinations of electrodes 24, 26. In particular, switch module 48 may create or cut off electrical connections between sensing module 46 and selected electrodes 24, 26 in order to selectively sense bioelectrical brain signals, e.g., in particular portions of brain 28 of patient 12. Processor 40 may also control switch module 48 to apply stimulation signals generated by stimulation generator 44 to selected combinations of electrodes 24, 26. In particular, switch module 48 may couple stimulation signals to selected conductors within leads 20, which, in turn, deliver the stimulation signals across selected electrodes 24, 26. Switch module 48 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 44 is coupled to electrodes 24, 26 via switch module 48 and conductors within leads 20. In some examples, however, IMD 16 does not include switch module 48.

Sensing module 46 is configured to sense bioelectrical brain signals of patient 12 via a selected subset of electrodes 24, 26. Processor 40 may control switch module 48 to electrically connect sensing module 46 to selected combinations of electrodes 24, 26. In this way, sensing module 46 may selectively sense bioelectrical brain signals with different combinations of electrodes 24, 26.

Stimulation generator 44 may be a single channel or multi-channel stimulation generator. For example, stimulation generator 44 may be capable of delivering, a single stimulation pulse, multiple stimulation pulses or a continuous signal at a given time via a single electrode combination or multiple stimulation pulses at a given time via multiple electrode combinations. In some examples, however, stimulation generator 44 and switch module 48 may be configured to deliver multiple channels on a time-interleaved basis. For example, switch module 48 may serve to time divide the output of stimulation generator 44 across different electrode combinations at different times to deliver multiple programs or channels of stimulation energy to patient 12.

Telemetry module 50 supports wireless communication between IMD 16 and an external programmer 14 or another computing device under the control of processor 40. Processor 40 of IMD 16 may, for example, transmit bioelectrical brain signals, signals indicative of patient motion, and temporal data via telemetry module 50 to a telemetry module within programmer 14 or another external device. Telemetry module 50 in IMD 16, as well as telemetry modules in other devices and systems described herein, such as programmer 14, may accomplish communication by radiofrequency (RF) communication techniques. In addition, telemetry module 50 may communicate with external medical device programmer 14 via proximal inductive interaction of IMD 16 with programmer 14. Accordingly, telemetry module 50 may send information to external programmer 14 on a continuous basis, at periodic intervals, or upon request from IMD 16 or programmer 14.

Power source 52 delivers operating power to various components of IMD 16. Power source 52 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Figure 3:
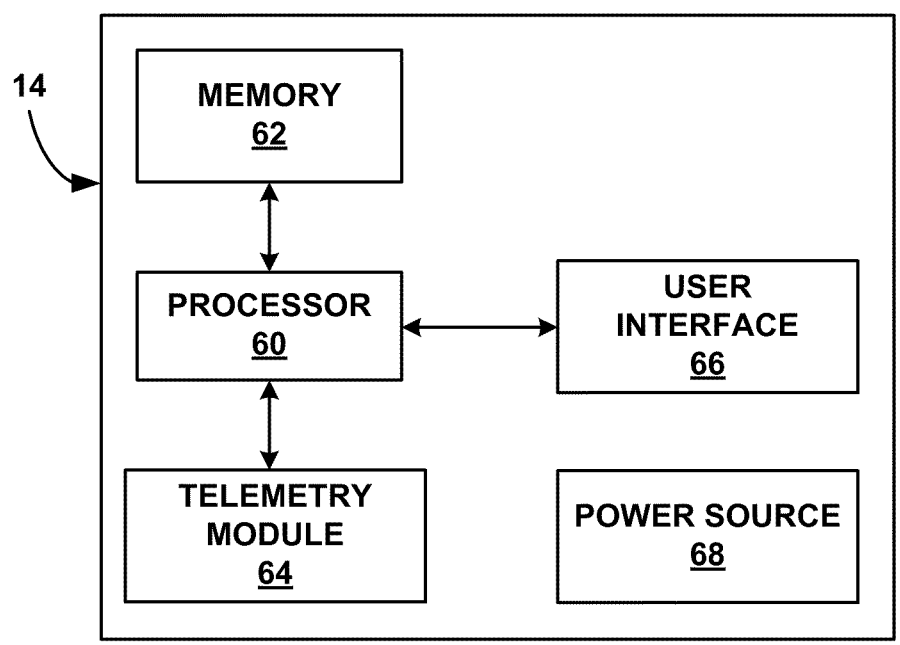
FIG. 3 is a functional block diagram illustrating components of an example medical device programmer.

FIG. 3 is a conceptual block diagram of an example external medical device programmer 14, which includes processor 60, memory 62, telemetry module 64, user interface 66, and power source 68. Processor 60 controls user interface 66 and telemetry module 64, and stores and retrieves information and instructions to and from memory 62. Programmer 14 may be configured for use as a clinician programmer or a patient programmer. Processor 60 may comprise any combination of one or more processors including one or more microprocessors, DSPs, ASICs, FPGAs, or other equivalent integrated or discrete logic circuitry. Accordingly, processor 60 may include any suitable structure, whether in hardware, software, firmware, or any combination thereof, to perform the functions ascribed herein to processor 60.

A user, such as a clinician or patient 12, may interact with programmer 14 through user interface 66. User interface 66 includes a display (not shown), such as a LCD or LED display or other type of screen, to present information related to the therapy, such as information related to bioelectrical signals sensed via a plurality of sense electrode combinations. The display may also be used to present a visual alert to patient 12 that IMD 16 has detected that a seizure event is impending or has already occurred. Other types of alerts are contemplated, such as audible alerts or somatosensory alerts. User interface 66 may also include an input mechanism to receive input from the user. The input mechanisms may include, for example, buttons, a keypad (e.g., an alphanumeric keypad), a peripheral pointing device or another input mechanism that allows the user to navigate though user interfaces presented by processor 60 of programmer 14 and provide input.

In the examples described herein, the display of user interface 66 presents a graphical user interface generated by processor 60 that indicates a temporal correlation between bioelectrical brain signal data and patient motion data (e.g., one or more patient posture indicators) of patient 12. As previously discussed, in other examples, a different user interface, e.g., a user interface of a device separate from programmer 14, may display the data.

If programmer includes buttons and a keypad, the buttons may be dedicated to performing a certain function, i.e., a power button, or the buttons and the keypad may be soft keys that change function depending upon the section of the user interface currently viewed on the display of user interface 66 by the user. Alternatively, the display (not shown) of programmer 14 may be a touch screen that allows the user to provide input directly to the user interface shown on the display. The user may use a stylus or a finger to provide input to the display. In other examples, user interface 66 also includes audio circuitry for providing audible instructions or notifications to patient 12 and/or receiving voice commands from patient 12, which may be useful if patient 12 has limited motor functions. Patient 12, a clinician or another user may also interact with programmer 14 to manually select therapy programs, generate new therapy programs, modify therapy programs through individual or global adjustments, and transmit the new programs to IMD 16.

In some examples, processor 60 may receive information related to bioelectrical brain signals and patient motion signals from IMD 16 or from a sensing module that is separate from IMD 16. The separate sensing module may, but need not be, implanted within patient 12. Processor 60 may, in addition, receive corresponding temporal information, e.g., timestamps, along with the bioelectrical brain signals and patient motion signals. In examples described herein, processor 60 generates a graphical representation that illustrates a temporal correlation between a bioelectrical brain signal of patient 12 and one or more patient posture indicators, and controls the display of user interface 66 to display the graphical representation to a user, e.g., a clinician. Examples techniques with which processor 60 can generate a graphical user interface that illustrates a temporal correlation between a bioelectrical brain signal of patient 12 and one or more patient posture indicators are described with respect to FIGS. 4 and 6.

Memory 62 may include instructions for operating user interface 66 and telemetry module 64, and for managing power source 68. Memory 62 may also store any therapy data retrieved from IMD 16 during the course of therapy, as well as seizure data (e.g., seizure indications that indicate the time and date of a seizure), sensed bioelectrical brain signals, activity sensor information (e.g., a signal indicative of patient motion), and temporal information corresponding to the bioelectrical brain signals and activity sensor information. Memory 62 may include any volatile or nonvolatile memory, such as RAM, ROM, EEPROM or flash memory. Memory 62 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 64. Accordingly, telemetry module 64 may be similar to the telemetry module contained within IMD 16. In alternative examples, programmer 14 may be capable of infrared communication or direct communication through a wired connection. In this manner, other external devices may be capable of communicating with programmer 14 without needing to establish a secure wireless connection.

Power source 68 delivers operating power to the components of programmer 14. Power source 68 may include a battery and a power generation circuit to produce the operating power. In some examples, the battery may be rechargeable to allow extended operation. Recharging may be accomplished by electrically coupling power source 68 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to obtain operating power. Power source 68 may include circuitry to monitor power remaining within a battery. In this manner, user interface 66 may provide a current battery level indicator or low battery level indicator when the battery needs to be replaced or recharged. In some cases, power source 68 may be capable of estimating the remaining time of operation using the current battery.

Figure 4A:
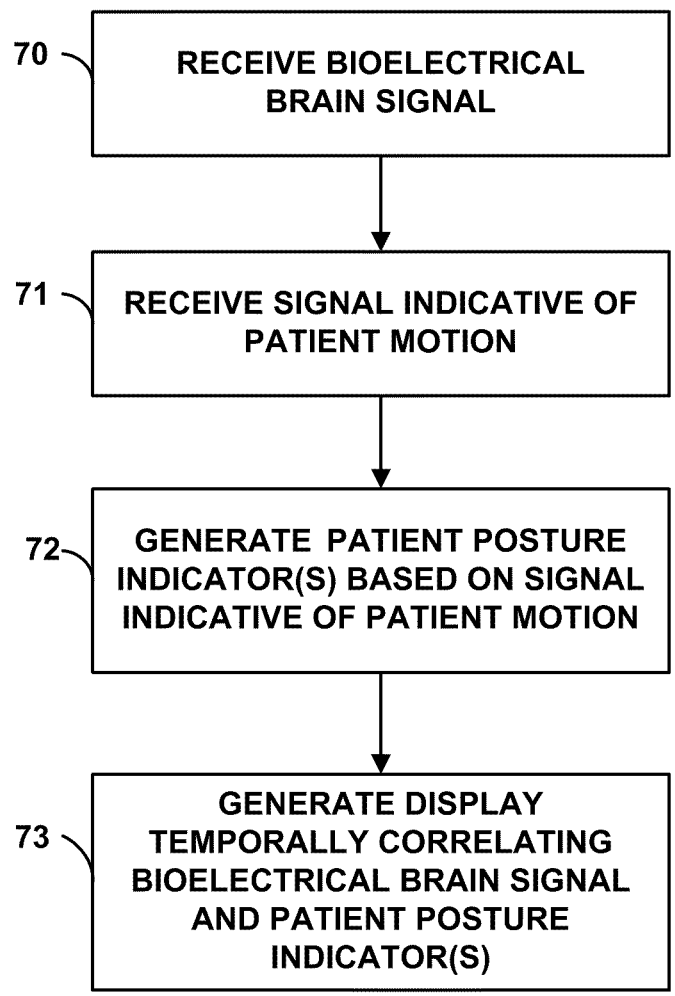
FIGS. 4A and 4B are flow diagrams illustrating examples of general techniques for generating a display that temporally correlates a bioelectrical brain signal of a patient and a signal indicative of patient motion.

FIG. 4A is a flow diagram illustrating an example of a general technique for generating a graphical user interface that temporally correlates a bioelectrical brain signal of a patient and patient motion data. Although the technique illustrated in FIG. 4A is described with respect to programmer 14 for ease of description, the technique may also be executed by another suitable device that includes a user interface.

Processor 60 of programmer 14 receives a signal that is indicative of bioelectrical activity within brain 28 of patient 12 (70). For example, sensing module 46 can, via selected electrodes 24, 26 of IMD 16 (FIG. 1), continuously or periodically sense electrical activity within brain 28 of patient 12 and continuously or periodically generate bioelectrical brain signals indicative of the electrical activity. In some examples, processor 40 stores the bioelectrical brain signals generated by sensing module 46 (FIG. 2) of IMD 16 in memory 42 (FIG. 2) of IMD 16. The bioelectrical signals may, in some examples, be stored as bioelectrical brain signal data 54 (FIG. 2). In other examples, the bioelectrical brain signals may not be stored in memory 42 of IMD 16. Instead, in some examples, the bioelectrical brain signals generated by sensing module 46 may be directly transmitted to programmer 14 via the respective telemetry modules 50 and 66 of IMD 16 and programmer 14, respectively. Processor 60 of programmer 14 can store the received bioelectrical brain signals in memory 62 (FIG. 3).

Processor 40 of IMD 16 may, in some examples, generate a timestamp or other temporal data and associate the timestamp (or other temporal data) with the bioelectrical brain signal data 54 generated by sensing module 46. For example, processor 40 may associate a plurality of different time domain segments of a bioelectrical brain signal with a respective timestamp, which can indicate, for example, the time of day at which the particular signal was sensed in brain 28 of patient. The segments of the bioelectrical brain signal can each have any suitable duration, such as about less than one second to about one minute or more. In addition, each segment of the bioelectrical brain signal associated with a timestamp (or other temporal data) can have different durations of time. For example, if processor 40 of IMD 16 determines that the amplitude or frequency of the bioelectrical brain signal is indicative of a possible seizure (e.g., based on comparison to a threshold value), processor 40 can shorten the duration of each segment of the bioelectrical brain signal associated with a timestamp, such that a more robust picture of the progression of the seizure can be generated via the more frequent time stamps and the greater number of discrete bioelectrical brain signal segments. Processor 40 may store the bioelectrical brain signals and corresponding temporal data within memory 42, e.g., within bioelectrical brain signal data module 54.

In some examples, IMD 16 may transmit the bioelectrical brain signal data 54 to programmer 14 via telemetry module 50. Telemetry module 64 of programmer 14 may receive the data from telemetry module 50 of IMD 16. In some examples, processor 60 may store the received data within memory 62 of programmer 14. In other examples, processor 60 need not store the data within memory 62 of programmer 14 and may only display the data received from IMD 16.

Programmer 14 may also receive a signal that is indicative of motion of patient 12 (71). For example, activity sensor 36 of IMD 16 may include an accelerometer, e.g., a three-axis accelerometer, that senses changes in acceleration of patient 12 along one or more axes. The changes in acceleration may be indicative of changes in a posture of patient 12. In examples in which activity sensor 36 includes a three-axis accelerometer, activity sensor 36 may generate at least three sets of data indicative of motion of patient 12. For example, activity sensor 36 may generate signals indicative of changes in acceleration in at least the x-axis, y-axis, and z-axis directions. Processor 40 of IMD 16 can store the signals generated by activity sensor 36 as patient motion data 56 of memory 42.

As with the bioelectrical brain signals, in some examples, processor 40 of IMD 16 associates a timestamp (or other temporal data) to segments of the patient motion signal generated by activity sensor 36. Processor 40 may store the signals indicative of patient motion and the corresponding temporal data within memory 42, e.g., as patient motion data module 56. IMD 16 may transmit the signals indicative of patient motion to programmer 14 via telemetry module 50. Telemetry module 64 of programmer 14 is configured to receive the patient motion data 56 transmitted by telemetry module 50 of IMD 16. In some examples, processor 60 stores the received patient motion data within memory 62 of programmer 14.

After receiving a bioelectrical brain signal and a signal indicative of patient motion, processor 60 generates at least one patient posture indicator based on the signal indicative of patient motion (72). As previously indicated, the patient posture indicator comprises a graphical representation of at least a portion of the body of patient 12 that corresponds to the signal indicative of patient motion. In some examples, processor 60 first determines the patient posture state based on a segment of the signal indicative of the patient motion and then determines the relevant icon or other object to be displayed via user interface 66 to represent the determined patient posture state. The segment of the signal indicative of the patient motion on which processor 60 determines the patient posture state can have any suitable duration. In some examples, processor 60 determines a patient posture state based on a discrete point of the signal, while in other examples, processor 60 determines a patient posture state based on a time window, such as about 0.5 seconds to about 60 seconds, or about 1 second to about 5 seconds of the signal.

The patient posture state can be determined based on the signal indicative of patient motion using any suitable technique. In some examples, memory 62 of programmer 14 or a memory of another device (e.g., IMD 16) stores definitions for each of a plurality of posture states of patient 12. In one example, the definitions of each posture state may be illustrated as a cone in three-dimensional space. Whenever the posture state parameter value, e.g., a vector, from the three-axis accelerometer of one or both motion sensors 25, 36 resides within a predefined cone or volume, processor 60 indicates that patient 12 is in the posture state of the cone or volume. In other examples, a posture state parameter value from the 3-axis accelerometer may be compared to values in a look-up table or equation to determine the posture state indicated by the patient motion signal segment. Examples techniques for detecting a patient posture state include examples described in U.S. Patent Application Publication No. 2010/0010383 A1 by Skelton et al., entitled "REORIENTATION OF PATIENT POSTURE STATES FOR POSTURE-RESPONSIVE THERAPY," filed Apr. 30, 2009, the entire content of which is incorporated by reference herein.

In another example, each posture state of a plurality of posture states can be defined by a threshold value of a signal characteristic (e.g., an amplitude, frequency or power level in a particular frequency band) of the patient motion signal generated by one or both motion sensors 25 or 36. Processor 60 can determine the patient posture state by comparing a patient motion signal characteristic to a threshold value. A plurality of threshold values can be stored and associated with respective patient posture states. If processor 60 determines the patient posture state based on a segment of the signal indicative of patient motion having varying amplitude or another varying signal characteristic (e.g., frequency), processor 60 can compare the mean, median, peak or lowest signal characteristic value to the threshold value to determine the patient posture state.

In another example, each posture state of a plurality of posture states can be defined by a signal template or other predetermined motion sensor output stored in memory 62 of programmer 14 (or another device). Processor 60 can determine the patient posture state by comparing the segment of the signal indicative of patient motion to a template stored in memory 62 or another device or to another predetermined motion sensor output stored in memory 62. A plurality of templates or motion sensor outputs can be stored and associated with respective patient posture states.

After determining the patient posture state based on the signal indicative of patient motion, processor 60 determines the relevant patient posture indicator to be displayed via user interface 66 to represent the determined patient posture state. Memory 62 of programmer 14 or a memory of another device can store a plurality of icons or other objects with associated patient posture states, and processor 60 can select the stored icon or other object associated with the determined patient posture state and display the selected icon or other object as the patient posture indicator. The icon or other object can be, for example, a graphical representation of at least a portion of a human body that visually indicates the patient posture state. While stick figures are described below, in other examples, the icon or other object displayed as the patient posture indicator can have any suitable complexity or form.

After generating the patient posture indicator, programmer 14 generates a display that temporally correlates the bioelectrical brain signal and the patient posture indicator (73). In some examples, generation of the display may be initiated when a clinician or other user provides input to programmer 14, e.g., by pushing a button on user interface 66 and/or programmer 14 or entering text on user interface 66, instructing programmer 14 to generate such a display. In other examples, programmer 14 may continuously acquire data from IMD 16 and, alternatively or additionally, user interface 66 may continuously include a display that temporally correlates the bioelectrical brain signal and the signal indicative of patient motion.

Figure 5:
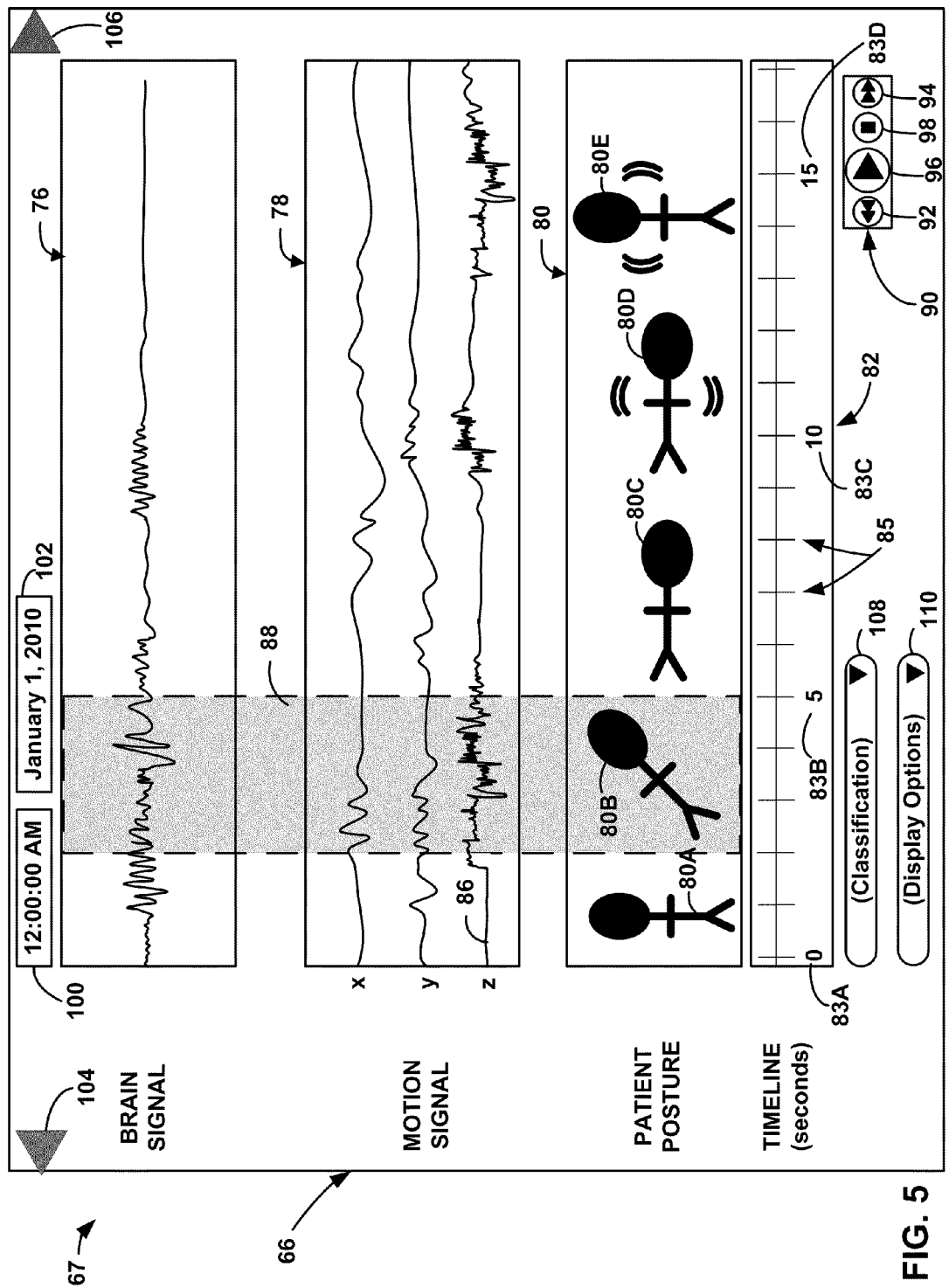
FIG. 5 is diagram illustrating an example user interface that temporally correlates a bioelectrical brain signal and a signal indicative of patient motion.
Figure 9:
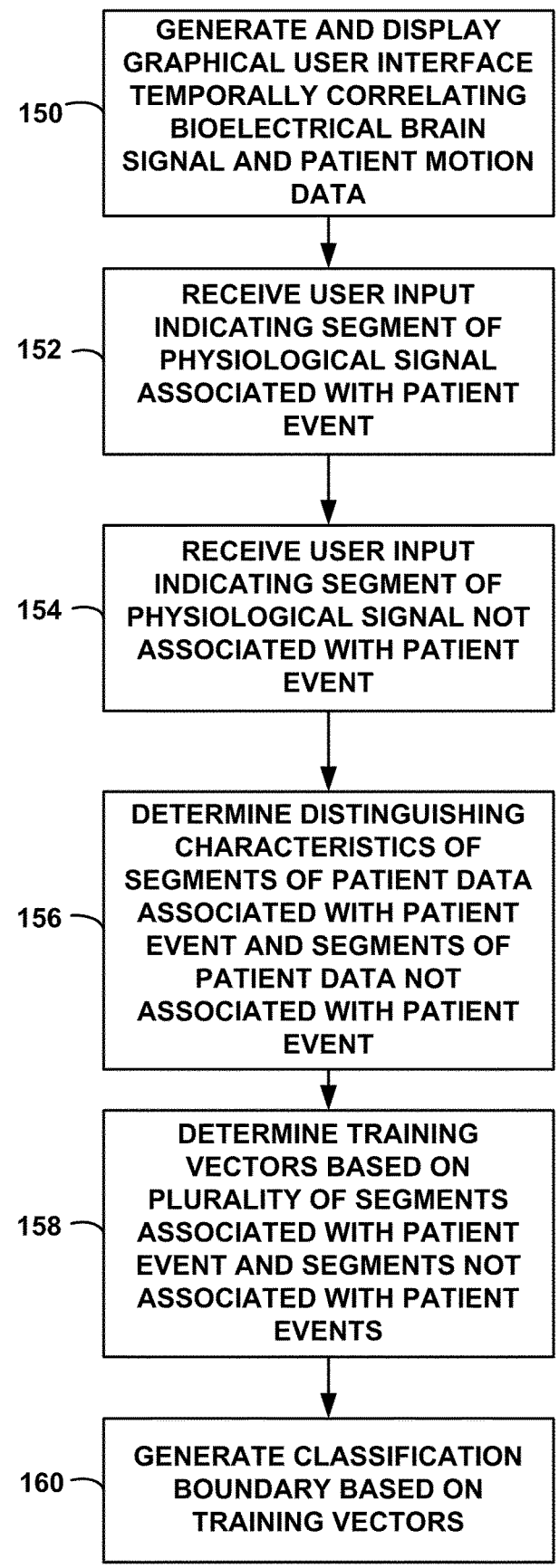
FIG. 9 is a flow diagram illustrating an example technique for training a support vector machine using a graphical user interface that temporally correlates a bioelectrical brain signal of a patient and a signal indicative of patient motion.

Processor 60 of programmer 14 accesses the bioelectrical brain signal and the signal indicative of patient motion and generates a display that illustrates a temporal correlation of the bioelectrical brain signal with a patient posture indicator, e.g., the displays illustrated in FIGS. 5 and 9. For example, processor 60 may display an EEG signal of patient 12, e.g., sensed by sensing module 46 of IMD 16 via a selected subset of electrodes 24, 26, and a plurality of patient posture indicators that are determined based on an accelerometer signal of patient 12, e.g., generated by activity sensor 36, on user interface 66. Processor 60 can display the EEG and patient posture indicators on user interface 66 such that the data from the EEG and patient posture indicators that are temporally associated with each other (e.g., were sensed at the same point in time) are generally aligned on user interface 66.

Figure 4B:
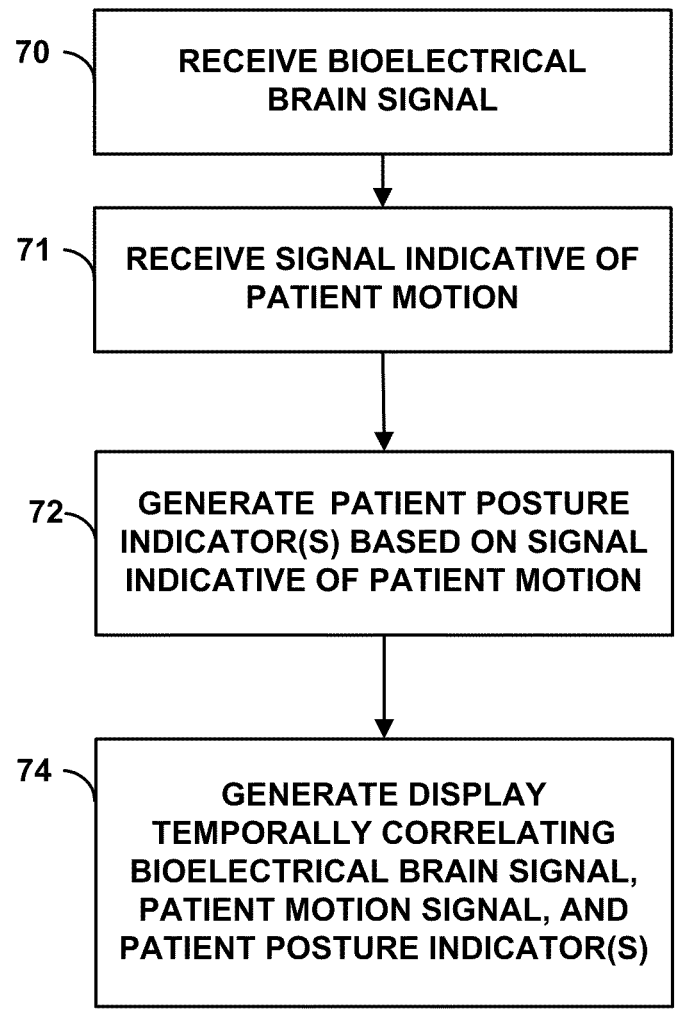

As shown in FIG. 4B, which is a flow diagram of another example technique, processor 60 of programmer 14 can also display the signal indicative of the patient motion (74) along with the bioelectrical brain signal and one or more patient posture indicators. Processor 60 can display the signals on user interface 66 such that they are generally aligned to show the temporal correlation of the signals. For example, processor 60 can display EEG and accelerometer signals on user interface 66 such that the data from the EEG and the accelerometer that are temporally associated with each other (e.g., were sensed at the same point in time) are generally aligned on user interface 66.

FIG. 5 illustrates an example graphical user interface 67 displayed by processor 60 of programmer 14 on a display of user interface 66, where graphical user interface 67 illustrates a temporal correlation of a bioelectrical brain signal 76, a signal 78 indicative of patient motion, and patient state indicators 80A-80E (collectively referred to as "patient posture indicators 80") determined based on signal 78 indicative of patient motion. In the example illustrated in FIG. 5, user interface 66 displays physiological data that was sensed during pre-ictal stage, an ictal stage, and during a post-ictal stage of a seizure occurrence of patient 12. In the examples described herein, a seizure event includes an ictal stage, during which the seizure is actually occurring, and, therefore, the patient's seizure symptoms are present. In addition, in some cases, the seizure event can include other periods of time in which bioelectrical brain signal 76 exhibits abnormal (e.g., compared to when a seizure is not occurring) activity. These periods of time may include the pre-ictal stage, which precedes the ictal stage, and the post-ictal stage, which follows the ictal stage. During the ictal and post-ictal stages, manifestations of the seizure may result in changes to the patient's physical activity (e.g., as indicated by a posture state).

In some examples, seizure events may be classified by the particular type of seizure. In some examples, a seizure may be classified by the part of brain 28 that is affected by the seizure. For example, a partial seizure affects only a localized area of the brain, while a generalized seizure affects both hemispheres of the brain. Each of these categories of classification may include particular sub-classifications of seizures, such as simple partial seizures, complex partial seizures, absence seizures, tonic-clonic seizures, myoclonic seizures, atonic seizures, and the like. Seizure events may also, in some examples, be classified based on whether the seizure event includes associated patient motion. For example, seizures that include only abnormal bioelectrical brain activity but do not include a motor component may be classified as sensory seizures. In some examples, sensory seizures may be less severe than motor seizures, which are seizure events that include a motor component, e.g., a fall. Sensory seizures may, in some examples, not greatly affect the patient's day-to-day activities because no physical manifestation of the seizure has occurred. In some examples, the patient may not be aware that a sensory seizure has occurred.

In some examples, the seizure disorder of patient 12 may be evaluated based on a patient activity level or a patient posture that is associated with a respective detected seizure. As an example, the patient activity level or patient posture state temporally correlated to a seizure may indicate the type of seizure or the severity of the seizure. For example, a relatively severe seizure, such as a tonic-clonic seizure, may result in involuntary patient movement, e.g., in the form of convulsive muscle movement. The convulsive movement may include, for example, twitching or violent shaking of the arms and legs. It may be desirable to monitor the patient's activity level during a seizure to detect seizures in which convulsive movement or other involuntary movement of patient 12 is observed. In contrast, a relatively minor seizure, e.g., a sensory seizure, may not have a motor component such that patient 12 does not undergo any characteristic movements during the seizure. In addition, a relatively severe seizure may result in a fall or another sudden change in posture by patient 12. Determining patient posture state or patient activity level temporally correlated with a bioelectrical brain signal may be useful for identifying relatively severe seizures, which can then be used to determine characteristics of the bioelectrical brain signal that are indicative of the relatively severe seizure.

User interface 66 displays bioelectrical brain signal 76, patient motion signal 78, patient posture indicator 80, and time indicator 82. Bioelectrical brain signal 76 is indicative of electrical activity within brain 28 of patient 12. In the example illustrated in FIG. 5, bioelectrical brain signal 76 represents an EEG signal sensed by, for example, sensing module 46 of IMD 16 via electrodes 24, 26 implanted within brain 28 of patient 12. In other examples, as previously discussed, bioelectrical brain signal 76 may include any suitable data that is indicative of electrical activity within brain 28 of patient 12, e.g., an ECoG signal, a LFP sensed from within one or more regions of a patient's brain, and/or action potentials from single cells within brain 28. In some examples, bioelectrical brain signal 76 may be representative of electrical activity within brain 28 while having a different appearance than bioelectrical brain signal 76 illustrated in FIG. 5. That is, bioelectrical brain signal 76 displayed by processor 60 can be a parameterized signal, or another signal that is generated based on a raw bioelectrical brain signal.

Patient motion signal 78 includes signal data generated by activity sensor 36 which, in the example shown in FIG. 5, is a three-axis accelerometer. Activity sensor 36 generates a signal that indicates a change in acceleration of patient 12 in multiple directions, e.g., in the x-axis direction, the y-axis direction, and the z-axis direction. Thus, in the example shown in FIG. 5, patient motion signal 78 is comprised of three signals that each represents patient motion in one of the x-axis, y-axis or z-axis directions. A signal that indicates a change in acceleration of patient 12 in a particular direction may represent the change in motion of patient 12 in the particular direction. In other examples, as previously discussed, activity sensor 36 may include one or more gyroscopes, pressure transducers, piezoelectric crystals, or other sensors that generate a signal indicative of patient activity. In these examples, processor 60 can generate a graphical user interface that includes a motion signal 78 that corresponds to the data acquired by activity sensor 36, e.g., in these examples, motion signal 78 may have a different appearance than motion signal 78 illustrated in FIG. 5.

In some examples, graphical user interface 67 includes only particular components of motion signal 78. For example, in some examples, user interface 66 may only include z-axis component 86 of motion signal 78. Z-axis component 86 may be more indicative of the overall posture of patient 12, e.g., may be indicative of whether patient 12 is in an upright position or has fallen, in comparison to the x-axis and y-axis components of motion signal 78. Thus, user interface 66 that includes only z-axis component 86 may provide an indication to a user of the posture of patient 12 while minimizing the information presented to the user, which can help simplify the display relating to the seizure event. However, a patient posture state can also be determined based on two or more axial components of the motion signal 78.

Patient posture indicators 80 are each a graphical representation of at least a portion the body of patient 12 that provides an indication of the patient posture state of patient 12. In the example shown in FIG. 5, patient posture indicators 80 are each graphical representations of the entire body of patient 12. In particular, patient posture indicators 80 are each displayed as stick figures that assume a particular configuration based on the particular patient posture state that corresponds to the particular segment of patient motion signal 78. In the examples described herein, patient posture indicators 80 are determined based on the posture state indicated by patient motion signal 78. As described above, processor 60 of programmer 14 or another device (e.g., processor 40 of IMD 16) determines a patient posture state at a particular point in time (e.g., a discrete time or a particular range of time) based on patient motion signal 78 and subsequently selects a patient posture indicator 80 that is associated with the patient posture state.

As shown in FIG. 5, patient posture indicators 80 each visually indicate the patient posture state using an intuitive graphical object. In some examples, processor 60 of programmer 14, or another processor of therapy system 10, may generate each patient posture indicator 80 by correlating particular characteristic of patient motion signal 78 with particular orientations of the stick figure that are visually representative of the posture of patient 12, e.g., using an algorithm.

A graphical representation of the body of patient 12, such as patient posture indicators 80, may provide a more intuitive indication of patient posture or motion in comparison to a signal generated by a sensor, such as patient motion signal 78. Consequently, patient posture indicator 80 may be useful in displaying the posture state of patient 12 to a user. Although FIG. 5 illustrates patient posture indicators 80 as stick figures, in other examples, patient posture indicators 80 may each include another representation of at least a portion of the body of patient 12. For example, patient posture indicators 80 may each include a more detailed representation of the body of patient 12, e.g., an avatar of patient 12, or a representation of only a portion of the body of patient 12, e.g., a limb of patient 12, that corresponds to patient motion signal 78 generated by activity sensor 36.

Graphical user interface 67 displays and highlights changes in a posture state of patient 12 over a period of time, e.g., the period of time represented by the data displayed on user interface 66 of programmer 14. In some examples, graphical representations of the body of patient 12 may highlight changes in the posture state of patient 12. For example, in some examples, each of patient posture indicators 80 may represent a different posture state of patient 12. A plurality of patient posture indicators 80 are displayed in FIG. 5. In some examples, a patient posture indicator 80 is displayed at regular intervals of time, such that the patient posture indicators 80 represent the posture state of patient 12 for substantially equal periods of time. That is, in some examples, processor 60 of programmer 14 generates each of the patient posture indicators 80 based on segments of motion signal 78 have substantially equal durations of time. In these cases, graphical user interface 67 can display substantially similar patient state indicators 80 in series, e.g., if the patient posture state remained unchanged for successive periods of time.

In other examples, graphical user interface 67 displays patient posture indicators 80 only when there is a change in patient posture. In this example, patient posture indicators 80 may each represent the posture state of patient 12 for different durations of time. That is, in these examples, processor 60 of programmer 14 can generate each of the patient posture indicators 80 based on segments of motion signal 78 have substantially different durations of time. Thus, in other examples, one patient posture indicator 80 may represent the posture state of patient 12 during an entire seizure event. In these examples, a single patient posture indicator 80 can graphically display a type of seizure (or other patient event relevant to the patient condition). For example, the tonic phase of a tonic-clonic seizure may be represented by a particular patient posture indicator 80, e.g., a stick figure within the fetal position.

In the example illustrated in FIG. 5, patient 12 may have undergone a tonic-clonic seizure. A tonic-clonic seizure may be characterized by a tonic phase, in which, during the ictal stage, the muscles of patient 12 may tense and cause patient 12 to fall, if standing. The tonic phase of the seizure event is represented, in the example illustrated in FIG. 5, by patient posture indicators 80B and 80C. Patient posture indicator 80B illustrates the initial falling motion of patient 12 and patient posture indicator 80C illustrates patient 12 in a horizontal position, e.g., patient 12 may be on the ground after the fall. The clonic phase of the seizure may be characterized by rapid contraction and relaxation of muscles of patient 12. Patient posture indicator 80D represents the rapid contraction and relaxation of muscles of patient 12 during the clonic phase of the seizure event, illustrated by the markings present on either side of patient posture indicator 80D in FIG. 5.

In FIG. 5, patient posture indicator 80A represents the upright posture state of patient 12 before the seizure event, and patient posture indicator 80E represents the resumption of the upright posture state of patient 12 in the post-ictal period, after the occurrence of the seizure. For example, patient 12 may move from the lying down posture state occupied during the seizure to an upright and active posture state in which patient 12 re-occupies the upright posture state.

As FIG. 5 illustrates, graphical user interface 67 generated by processor 60 of programmer 14 based on signals 76, 78 can be useful for showing the time course of patient 12 motion during a seizure event. This can be useful for a clinician to determine, for example, during an evaluation period after the sensing and storing of bioelectrical brain signal 76 and patient motion signal 78, what motor activity patient 12 underwent during the seizure. This automatic determination of the patient motor activity can lower the burden on patient 12 or a patient caretaker compared to examples in which patient 12 (or the patient caretaker) manually inputs or otherwise acquires data relating to the patient motor activity during the seizure. In addition, the clinician, alone or with the aid of processor 60, can determine when a seizure occurred based on bioelectrical brain signal 76. This automatic recording of bioelectrical brain signal 76 can also lower the burden on patient 12 (or a patient caretaker) to keep a log or other record of each seizure occurrence, which can be burdensome on patient 12 because of the occurrence of frequent seizures or because of the inconvenience of recording such data.

In addition, graphical user interface 67 presents relevant data with which the user can relatively quickly ascertain whether a seizure indicated by bioelectrical brain signal 76 was relatively severe (e.g., as indicated by temporally correlated motor activity) or whether the seizure was relatively minor (e.g., as indicated by the absence of motor activity). If, for example, patient posture indicators 80 indicate patient 12 changed posture state during a seizure event or exhibited a certain pattern in posture state changes, the user can determine that the seizure event was associated with motor activity. On the other hand, if patient posture indicators 80 indicate patient 12 maintained the same or similar posture state during a seizure event, the user can determine that the seizure event was a sensory seizure not associated with a motor component.

In some examples, the user manually identifies an occurrence of a seizure based on the display of bioelectrical brain signal 76, while in other examples, processor 60 of programmer 14 automatically identifies an occurrence of a seizure based on the display of bioelectrical brain signal 76 (e.g., using thresholds, template matching or any other suitable technique). For example, processor 60 can implement a seizure prediction technique discussed in commonly-assigned U.S. Pat. No. 7,006,872, entitled, "CLOSED LOOP NEUROMODULATION FOR SUPPRESSION OF EPILEPTIC ACTIVITY," which discloses a technique in which a seizure is predicted based on whether a sensed EEG starts to show synchrony as opposed to the normal stochastic features.

The particular posture state represented by each of patient posture indicators 80 is representative of the data contained within the segment of patient motion signal 78 aligned with, e.g., directly above the particular patient posture indicator 80 in graphical user interface 67. Example posture states include, but are not limited to, the posture state associated with a fall associated with loss of consciousness during a seizure, sitting upright after regaining consciousness from a seizure, standing upright after regaining consciousness from a seizure, tonic seizure component (e.g., stiffening of the body), clonic seizure component (e.g., jerking of the body), tonic-clonic seizure, convulsive activity (e.g., twisting or shaking), nocturnal seizure activity, dystonic-type movements, tic, and the like. In other examples, as shown in FIG. 5, a plurality of patient posture indicators 80 represent a tonic-clonic seizure.

In some examples, a user may view posture state indicators 80 and determine that patient motion that may correlate to a seizure occurred during the time period represented by graphical user interface 67. The user may then view the temporally correlated segments of bioelectrical brain signal 76 to determine whether bioelectrical brain signal 76 also exhibits characteristics of a seizure event or which characteristic of bioelectrical brain signal 76 are indicative of the seizure event. In the example illustrated in FIG. 5, the user may determine that activity within bioelectrical brain signal 76 that temporally, correlates to posture state indicators 80B and 80C, e.g., increased frequency and amplitude of bioelectrical brain signal 76, is indicative of a tonic phase of a seizure. Although FIG. 5 illustrates only one seizure event, in other examples, graphical user interface 67 may display data related to more than one event. For example, graphical user interface 67 may display data that represents two or more events of interest within the same display.

As discussed above, programmer 14 may use any suitable technique to determine that patient 12 was in a particular posture state for a particular period of time. For example, programmer 14 may analyze patient motion signal 78 using an algorithm that determines that patient 12 was in a particular posture state for a particular period of time if patient motion signal 78 exhibits a particular characteristic for the particular period of time.

In some examples, user interface 66 may not include patient posture indicators 80, e.g., user interface 66 may only include one or more components of motion signal 78. In other examples, user interface 66 may not include motion signal 78, e.g., user interface 66 may include only patient posture indicators 80 as graphical displays of patient motion. Patient posture indicators 80 may provide a more intuitive representation of the motion of patient 12 to a user, e.g., a clinician, in comparison to motion signal 78. For example, a user may recognize the changes in posture state indicators 80 as being representative of changes in a posture state of patient 12 more easily than recognizing changes in the accelerometer signal readings of motion signal 78.

In the example of graphical user interface 67 shown in FIG. 5, bioelectrical brain signal 76, patient motion signal 78, and patient posture indicators 80 are aligned vertically on top of one another in a manner that illustrates a temporal correlation between bioelectrical brain signal 76, patient motion signal 78, and patient posture indicators 80. That is, in the example illustrated in FIG. 4, bioelectrical brain signal 76, patient motion signal 78, and patient posture indicators 80 are stacked vertically such that a segment of bioelectrical brain signal 76, a segment of patient motion signal 78, and individual patient posture indicators 80 that are displayed substantially directly on top of one another are representative of events that occurred during the same period of time.

In some examples, user interface 66 also includes time indicator 82. In the example illustrated in FIG. 5, time indicator 82 includes labels 83A, 83B, 83C, and 83D (collectively "labels 83") and markings 85 that provide a temporal reference for a user. For example, time indicator 82 provides a visual indication of the passage of time during the time period for which data is currently displayed on user interface 66. In the example illustrated in FIG. 5, time indicator 82 includes markings 85 that each visually represents a particular amount of time. For example, in the example illustrated in FIG. 5, the space between two consecutive markings 85 is representative of approximately one second of time. Thus, a segment of bioelectrical brain signal 76 or patient motion signal 78 that is positioned substantially directly above and extends between two consecutive markings 85 occurred over approximately one second. In the example illustrated in FIG. 5, labels 83 denote particular values in order to attach significance to markings 85. For example, in some examples, time indicator 82 includes labels 83 denoting, in combination with markings 85, the passage of a particular amount of time, e.g., a particular number of seconds, minutes, hours, or the like. In the example illustrated in FIG. 5, for example, time indicator 82 includes labels 83A, 83B, 83C, and 83D denoting, in combination with markings 85, the passage of approximately 0 second, approximately 5 seconds, approximately 10 seconds, and approximately 15 seconds, respectively. With the reference points provided by labels 83 and markings 85, a user may determine that the event illustrated on user interface 66 occurred during a particular amount of time, e.g., approximately 17 seconds.

Time indicator 82 may allow a user to identify particular characteristics of the patient data related to passage of time. In some examples, time indicator 82 may be useful for indicating, for example, the amount of time spent by patient 12 within a particular posture state, the time delay between a particular characteristic of bioelectrical brain signal 76 and a particular characteristic of motion signal 78, the duration of a physiological event, e.g., a seizure event, and the like. The amount of time spent by patient 12 within a particular posture state can be useful for evaluating the severity of the seizure event. For example, if patient 12 occupied a lying down posture state for a relatively long period of time (e.g., as indicated by a predetermined threshold value stored in memory 62 of programmer or another device), a user may determine that the seizure was relatively debilitating and, therefore, severe. Graphical user interface 67 can indicate the duration of time patient 12 occupied a lying down posture state during the seizure event via time indicator 82. That is, a user can identify the patient state indicators 80C, 80D associated with lying down posture states and determine, based on time indicator 82, the period of time with which the patient state indicators 80C, 80D are associated. In the example shown in FIG. 5, the user may observe that patient state indicators 80C, 80D associated with lying down posture states are displayed for approximately 8 seconds.

In the example illustrated in FIG. 5, time indicator 82 includes label 83A that denotes the passage of zero seconds, or that denotes the starting point for the segment of patient data displayed on graphical user interface 67. In other examples, instead of denoting the passage of time relative to substantially the entire segment of patient data displayed on graphical user interface 67, time indicator 82 may be positioned to denote the passage of time relative to a particular characteristic in bioelectrical brain signal 76 or patient motion signal 78, or relative to a particular patient event, e.g., a detected seizure event. For example, in some examples, time indicator 82 may be configured such that label 83A, which denotes the passage of zero seconds, indicates the starting point of abnormal activity within bioelectrical brain signal 76, instead of denoting the starting point for the entire segment of patient data displayed on graphical user interface 67. That is, processor 60 of programmer 14 (or another computing device) can position label 83A within graphical user interface 67 substantially directly below the portion of bioelectrical brain signal 76 that is initially indicative of seizure activity within brain 28 of patient 12. In this way, label 83A provides a reference that may more effectively allow a user to assess motion changes of patient 12 (via, e.g., patient posture indicators 80) relative to the seizure activity within bioelectrical brain signal 76, in comparison to time indicator 82 that denotes the passage of time relative to substantially the entire segment of patient data displayed on graphical user interface 67. In some examples, graphical user interface 67 may include a different type of time indicator 82 that is operable for providing a visual reference that relates the data displayed on user interface 66, e.g., bioelectrical brain signal 76 and patient motion signal 78, to a corresponding amount of time during which the data was collected. For example, time indicator 82 may be representative of a clock that illustrates the passage of time during replay of the events on graphical user interface 67, e.g., time indicator 82 may be similar to a stopwatch. In other examples, graphical user interface 67 may not include time indicator 82 because bioelectrical brain signal 76 and patient motion signal 78 are displayed on user interface 66 in a manner that visually temporally correlates the signals.

In some examples, user interface 66 of programmer 14 may include a feature (not shown) that allows a user to selectively display particular data on user interface 66. The component can be, for example, a button, a keypad, or another input mechanism. For example, user interface 66 may include a component that allows a user to select whether to display none, any, or all of the components of motion signal 78 on graphical user interface 67, e.g., a drop-down menu. A user may also be able to select whether to include patient posture indicator 80 and time indicator 82 in graphical user interface 67. In some examples, user interface 66 may be a touch screen that allows a user to select, align, and manipulate components of graphical user interface 67 with, e.g., a finger or a stylus. In this way, graphical user interface 67 may be customized to the needs and preferences of a user.

In some examples, as illustrated in FIG. 5, graphical user interface 67 includes sliding window 88. Processor 60 of programmer 14 controls the movement of sliding window 88 in a horizontal direction across user interface 66 in order to highlight segments of bioelectrical brain signal 76, motion signal 78, and patient posture indicators 80 that are representative of bioelectrical brain activity and patient motion that occurred within the same period of time. In this way, sliding window 88 of graphical user interface 67 can be an additional tool to aid a user's visualization of the seizure data, e.g., bioelectrical brain signal 76, patient motion signal 78, and patient state indicators 80, that temporally correlate to each other.

In some examples, a user may control the motion of sliding window 88. For example, in the example illustrated in FIG. 5, graphical user interface 67 includes controls 90 that allow a user to control the motion of sliding window 88 in order to actively highlight particular segments of interest. Controls 90 include rewind button 92, forward button 94, play button 96, and pause button 98. Rewind button 92 may be selected to move sliding window 88 from a currently highlighted portion of patient data to a portion of data from a period of time preceding that currently highlighted by sliding window 88. For example, in the example illustrated in FIG. 5, rewind button 92 may be useful for moving sliding window to the left to highlight a portion of bioelectrical brain signal 76, patient motion signal 78, and one or more patient posture indicators 80 that are positioned to the left of a currently highlighted portion.

Similarly, forward button 94 may be selected to move sliding window 88 from a currently highlighted portion of patient data to a portion of data indicating physiological data for a time period subsequent to the currently highlighted portion. For example, in the example illustrated in FIG. 5, a user can select forward button 94 to shift sliding window 88 to the right of the currently highlighted portion. In some examples, each activation (e.g., by physically pushing a button or interacting with a touch screen) of rewind button 92 and forward button 94 shift sliding window 88 by discrete movements in the respective direction, such that the user can only highlight pregrouped segments of the signals 76, 78. In other examples, rewind button 92 and forward button 94 shift sliding window 88 by any interval of time selected by a user. For example, the user can activate (e.g., by physically pushing a button or interacting with a touch screen) rewind button 92 and forward button 94, and, in response, processor 60 or programmer 14 can smoothly move sliding window 88 in the respective direction until the user activates pause button 98 or otherwise deactivates rewind button 92 and forward button 94.

Play button 96 may be selected to initiate movement of sliding window 88 forward with respect to time, e.g., to the right in FIG. 5. Upon selection of play button 96, sliding window 88 may continue to move forward, scrolling through and highlighting successive segments of the patient data. Pause button 98 may be selected in order to cause sliding window 88 to stop moving, e.g., to highlight a particular segment of user interface 66 for an extended period of time. Play button 96 may shift sliding window 88 at a slower rate than forward button 94.

In some examples, graphical user interface 67 only presents one or fewer than all patient posture indicators 80 temporally correlated with the displayed bioelectrical brain signal 76 or patient motion signal 78 at a time. For example, processor 60 may control graphical user interface 67 to display only one patient posture indicator that temporally correlates with a highlighted segment of bioelectrical brain signal 76 or patient motion signal 78, and does not display the patient posture indicators 80 associated with the non-highlighted segments of bioelectrical brain signal 76 or patient motion signal 78. In some examples, upon receiving input from a user activating play button 96, processor 60 can generate and display a plurality of successive patient posture indicators 80, such that the patient motion associated with successive segments of bioelectrical brain signal 76 or patient motion signal 78 is recreated and displayed in graphical user interface 67. The successive patient posture indicators 80 can be displayed one at a time, or each posture state indicator 80 can remain within graphical user interface 67 after being displayed, so as to leave a trail of posture state indicators 80.

In the example illustrated in FIG. 5, user interface 66 is a touch screen that is configured to directly accept input from a user via, e.g., a finger or a stylus. However, in other examples, controls 90 may be buttons or keys on a keypad. Controls 90 may also have any suitable configuration, e.g., controls 90 may not look like controls 90 illustrated in FIG. 5. For example, controls 90 may include written text describing the function of each of controls 90, e.g., in some examples, control 92 may display "back," control 94 may display "forward," control 96 may display "play," and control 98 may display "pause." As another example, in some examples, graphical user interface 67 includes only one of forward button 94 or play button 96. Other types of techniques for receiving user input for moving sliding window 88 or another highlighting object are contemplated.

Alternatively or additionally, user interface 66 may be capable of directly accepting input from a user that controls the position of sliding window 88. For example, a user may directly manipulate the position of sliding window 88 on user interface 66 by, e.g., selecting and dragging sliding window 88 to a desired location in order to highlight a desired portion of patient data using, e.g., a finger or a stylus in examples in which user interface 66 is a touch screen. In some examples, a user may select one or more options from a menu of options related to the position of sliding window 88.

In the example illustrated in FIG. 5, sliding window 88 also highlights changes in posture state of patient 12 that are represented by patient posture indicators 80. In some examples, sliding window 88 may move within graphical user interface 67 in increments that are determined based on patient posture indicators 80. For example, sliding window 88 may scroll across graphical user interface 67 by visibly skipping from one patient posture indicator 80 to the next consecutive patient posture indicator 80. As another example, sliding window 88 may scroll across graphical user interface 67 by visibly skipping from one patient posture indicator 80 indicating a first posture state to the next patient posture indicator 80 that indicates a different posture state. In these examples, the width of sliding window 88 may indicate the amount of time spent in a particular posture state represented by a particular patient posture indicator 80. In this way, the position of sliding window 88 indicates that patient 12 was in a particular posture state over the time period highlighted by sliding window 88.

Moving sliding window 88 at increments determined based on patient posture indicators 80 can be useful for, for example, quickly ascertaining the relevant segments of bioelectrical brain signal 76 and/or patient motion signal 78 associated with the patient posture state. For example, if the user is interested in determining a characteristic of bioelectrical brain signal 76 that occurred before a patient fall, the user can move sliding window 88 within graphical user interface 67 to either patient posture indicator 80A or patient posture indicator 80B in order to highlight the relevant segment of bioelectrical brain signal 76. In this way, graphical user interface 67 includes a visual feature that identifies the particular posture state of patient 12 during the time period highlighted by sliding window 88. For example, patient posture indicators 80 provide icons that display the posture state of patient 12, e.g., upright before seizure event, upright after seizure event, fall associated with loss of consciousness, etc., when a particular patient posture indicator 80 is highlighted by sliding window 88.

In some examples, however, sliding window 88 may not move within graphical user interface 67 at increments based on patient posture indicators 80. For example, in some examples, sliding window 88 may smoothly scroll across user interface 66, instead of visibly skipping.

In some examples, graphical user interface 67 may include a feature that allows a user to view a selected portion of patient data in greater detail. For example, processor 60 may identify a segment of patient data that includes a particular event of interest, e.g., seizure activity within bioelectrical brain signal 76 or a behavioral event illustrated by particular patient posture indicators 80, and highlight the segment of patient data, e.g., via sliding window 88. Upon identifying the particular segment of patient data, processor 60 may display, via graphical user interface 67, a more detailed version of the particular segment of patient data. That is, graphical user interface 67 may include a "zoom" feature that allows a user to zoom in on a particular segment of patient data in order to view a more detailed version of the particular data, e.g., a version of the data that includes more data samples. For example, processor 60 may cause graphical user interface 67 to expand the segment of patient data to fill a larger portion, e.g., the entire area, of graphical user interface 67 and to include more samples of the signal data. This feature may allow the user to more accurately assess the physiological activity, e.g., brain activity or motion activity, of patient 12 during the time period associated with the event of interest. In some examples, a user, instead of or in addition to processor 60, may identify the particular segment of patient data, e.g., by moving sliding window 88 to highlight the particular segment of patient data. The user may input a "zoom" command that instructs processor 60 to generate graphical user interface 67 that includes more detailed patient data for the particular patient data of interest.

In some examples, graphical user interface 67 also includes an indicator of the date and/or time in which the data displayed via graphical user interface 67 were initially sensed and recorded by IMD 16 or another device. In the example illustrated in FIG. 5, user interface 66 includes time stamp 100 and date stamp 102. Time stamp 100 indicates the time, e.g., the time of day, at which the bioelectrical brain signal 76 and the patient motion signal 78 currently displayed on user interface 66 were sensed by IMD 16, e.g., beginning at 12:00:00 AM in the example of FIG. 5. Similarly, date stamp 102 indicates the date on which the bioelectrical brain signal 76 and the patient motion signal 78 were initially sensed within patient 12, e.g., Jan. 1, 2010 in the example of FIG. 5. Time stamp 100 and date stamp 102 may automatically change based on the data that is displayed on user interface 66. For example, each data record stored in memory 62 may be correlated with time and/or date data, and processor 60 may automatically update time stamp 100 and date stamp 102 based on the particular data values displayed on user interface 66. Alternatively, user interface 66 may not include time stamp 100 and date stamp 102, or may include date and time indicators with a different configuration than time stamp 100 and date stamp 102.

In some examples, graphical user interface 67 also includes a feature that allows a user to select and view data sensed at a different time than the data currently displayed on user interface 66. For example, in the example illustrated in FIG. 5, a user may select controls 104 and 106 in order to view data from patient 12 other than the data that is currently displayed on user interface 66. Upon receipt of user input via control 104, processor 60 may control user interface 66 to display data that was collected during a period of time prior to the period of time in which the data currently displayed on user interface 66 was collected, e.g., prior to 12:00:00 AM on Jan. 1, 2010 in the example illustrated in FIG. 5. Similarly, upon receipt of user input via control 106, processor 60 may generate and display a graphical user interface that includes data that was collected during a period of time after the period of time in which the data currently displayed on user interface 66 was collected, e.g., after 12:00:00 AM on Jan. 1, 2010.

In FIG. 5, controls 104 and 106 are represented by left-facing and right-facing arrows, respectively. The arrows may be a graphical representation that allows a user to intuitively determine the function of controls 104 and 106, e.g., scrolling backward and forward through data that was collected at a different time than the data currently displayed on user interface 66 without additional instructions, e.g., without having to read an instruction manual. In other examples, controls 104 and 106 may have a different configuration. For example, controls 104 and 106 may be buttons that include written words, e.g., control 104 may include a written word such as "back" and control 106 may include a written word such as "forward." In some examples, a user may be able to enter a particular date and/or time or range of dates and/or times that are of interest and user interface 66 can display the data that corresponds to the particular dates and/or times upon the request of the user.

In the example illustrated in FIG. 5, user interface 66 is a touch screen that is configured to directly accept input from a user via, e.g., a finger or a stylus. Consequently, controls 104 and 106 are buttons on the touch screen that are directly responsive to user input. However, in other examples, controls 90 may be buttons or keys on a keypad.

In some examples, user interface 66 includes a component that allows a user to control the particular data type that is included in graphical user interface 67 and displayed on user interface 66. In the example illustrated in FIG. 5, user interface 66 includes display options menu 110 by which a user may control the particular data that is displayed on user interface 66, e.g., a user may filter the patient data to display only data types of interest. For example, in some examples, a user may determine that time periods that include a particular type of patient motion, e.g., a patient fall, are of particular interest. A user may select, from display options menu 110, an indicator of the particular type of motion, e.g., a selection such as "events that include a fall," in order to instruct processor 60 of programmer 14 to display only bioelectrical brain signal 76, posture state indicators 80 and/or other data related to events that include a fall.

In other examples, a user may be particularly interested in time periods that include both a fall and a bioelectrical brain signal indicative of, e.g., a seizure event. In these examples, a user may select, from display options menu 110, an indicator such as "events that include a fall and seizure activity." As another example, a user can select a type of patient posture indicator (e.g., by selecting a textual description of a particular patient posture or selecting a graphical representation of the posture indicator) and, in response, processor 60 can display a user interface that includes bioelectrical brain signal 76 and/or other physiological signal that temporally correlate to the selected types of patient posture indicators.

Although FIG. 5 illustrates display options menu 110 as a drop-down menu, in other examples, user interface 66 may include a different component that allows a user to control the particular data that is displayed. For example, user interface 66 may display an additional screen in which the user may select the type of patient data that is of particular interest, e.g., prior to displaying a screen that includes the patient data.

In some examples, in order to filter patient data, processor 60 may execute one or more algorithms: For example, in order to determine whether a particular characteristic related to patient motion, e.g., a fall, has occurred, processor 60 may execute an algorithm using the data included in patient motion signal 78. The algorithm may compare patient motion signal 78 to previously-defined templates or thresholds in order to determine whether a particular type of motor activity event, e.g., an event that includes a fall, has occurred. Similarly, processor 60 may monitor and analyze bioelectrical brain signal 76 by, for example, executing a seizure detection algorithm, to determine whether bioelectrical brain signal 76 exhibits characteristics indicative of a seizure.

Upon receiving input via display options menu 110, processor 60 can filter out patient data other than data that fits the criteria selected by the user. Consequently, when the user selects, for example, controls 104 and 106 in order to view data associated with a time period different than the data that is currently displayed, processor 60 can instruct user interface 66 to scroll between only events with the particular criteria specified by the user.

Graphical user interface 67 generated by processor 60 includes one or more features through which a user can provide input to organize the patient data received from IMD 16 or another sensor. For example, graphical user interface 67 can include a feature that allows a user to classify a particular posture state, a particular seizure event, and/or another type of event, e.g., a set of data that includes a series of posture states of interest. In the example illustrated in FIG. 5, classification bar 108 allows a user to select a classification label from a list and associate the label with a particular posture state or a particular event. In FIG. 5, classification bar 108 is a drop-down menu that displays a list of classification options to a user when the user selects the arrow of classification bar 108. In other examples, user interface 66 may include any suitable component that allows a user to classify a particular posture state and/or a particular physiological event.

In the example illustrated in FIG. 5, a user may select a particular segment of data (e.g., bioelectrical brain signal 76, signal 78 indicative of patient motion, or one or more patient posture indicators 80) in order to classify a posture state, e.g., the posture of patient 12 at a particular point in time, associated with the data segment. The user can select a segment of data using any suitable technique, such as by providing input to user interface 66 marking the segment of data or highlighting the segment of data with sliding window 88. For example, a user may observe the bioelectrical brain activity 76, the patient motion signal 78, and/or the patient posture indicator 80 and determine that the posture state of patient 12 associated with the data segment highlighted by sliding window 88 may appropriately be classified as a "fall associated with loss of consciousness during a seizure." Other examples may include, but are not limited to, "sitting/standing upright after regaining consciousness from a seizure," a "tonic seizure component (stiffening)," a "clonic seizure component (jerking)," "convulsive activity," and "nocturnal seizure activity." Processor 60 of programmer 14 may associate the classification with the particular data segment, e.g., within a memory such as memory 42 of IMD 16 or memory 62 of programmer 14. A user may refer to the classification if, for example, the user is interested in observing patterns in the signals associated with particular seizure events.

In other examples, a user may select a particular segment of data that includes multiple changes in posture states. In some examples, the user may select an entire event, e.g., a series of posture states, that may be of interest. For example, with respect to the example illustrated in FIG. 5, upon identifying that a particular segment of the patient physiological data includes characteristics that are consistent with a particular physiological event, a user may select substantially all of the data illustrated on user interface 66 and may classify the series of posture states (as indicated by posture state indicators 80) as a particular type of event, e.g., a tonic-clonic seizure. In this example, the user may highlight substantially all of the data, e.g., by dragging the tip of a stylus around the area of user interface 66 that includes the data of interest, in examples in which user interface 66 is a touch screen, and may select "tonic-clonic seizure" from the drop-down menu of classification bar 108. Other examples may include, but are not limited to, "sensory seizure," "motor seizure," "pre-ictal stage of seizure," "post-ictal stage of seizure," "myoclonic seizure," "atonic seizure," "partial seizure," and the like Processor 60 of programmer 14 may then associate the classification with the particular data segment, e.g., within a memory such as memory 62.

The user can drag the tip of a stylus or otherwise provide input via a input mechanism of user interface 66 selecting any portion of bioelectrical brain signal 76, signal 78 indicative of patient motion, and/or one or more patient posture indicators 80. In some examples, upon receiving input selecting a segment of bioelectrical brain signal 76, processor 60 automatically includes the segment of signal 78 and/or posture state indicators 80 temporally correlated with the user selected segment of bioelectrical brain signal 76 as part of the data associated with the user-provided classifier. In this way, processor 60 can automatically determine relevant patient physiological data in response to the patient input. Similarly, upon receiving input selecting a segment of signal 78 indicative of patient motion, processor 60 automatically includes the segment of bioelectrical brain signal 76 and/or posture state indicators 80 temporally correlated with the user selected segment of signal 78 as part of the data associated with the user-provided classifier. In addition, upon receiving input selecting one or more patient posture indicators 80, processor 60 automatically includes the segment of bioelectrical brain signal 76 and/or signal 78 indicative of patient motion temporally correlated with the user selected segment of bioelectrical brain signal 76 as part of the data associated with the user-provided classifier.

In some examples, processor 60 automatically generates and places a visual marker (e.g., a hash mark) that indicates a change in posture state of patient 12 on bioelectrical brain signal 76 shown in graphical user interface 67. A visual marker that marks the time at which patient 12 changed from a first posture state to a second posture state may be useful for, for example, allowing a user to relatively quickly identify changes in the bioelectrical brain signal 76 that correspond to changes in posture state. The user may employ this information regarding the patient posture change to, for example, identify segments of bioelectrical brain signal 76 temporally correlated with the posture change. The segment can be useful for identifying patterns within bioelectrical brain signal 76 that may provide indicators of a change in posture state of patient 12, e.g., before the change in posture state occurs.

Processor 60 can determine when patient 12 changed posture state based on signal 78 indicative of patient motion. As discussed above, processor 60 can implement any suitable algorithm for determining a patient posture state based on signal 78 indicative of patient motion. For example, processor 60 may associate one or more characteristics (e.g., amplitude, pattern or frequency domain characteristics) of signal 78 with a particular patient posture, such as sitting, prone, recumbent, upright, and so forth. Processor 60 can determine a first portion of signal 78 that indicates a different patient posture state than the immediately preceding portion of signal 78 and identify the time associated with the first portion of signal 78 as a time at which a patient posture state change occurred. Processor 60 can then determine which portion of bioelectrical brain signal 76 temporally correlates with the first portion of signal 78 and generate and place the visual marker at the temporally correlated portion of bioelectrical brains signal 76 in order to mark when patient 12 changed posture state.

The time point at which patient 12 changes posture state may, in some examples, be identified by other processors of therapy system 10, e.g. processor 40. In other examples, graphical user interface 67 can be configured to receive user input marking changes in posture state on bioelectrical brain signal 76. In response to receiving the user input, processor 60 of programmer 14 can generate and place the visual marker within graphical user interface 67 at the location indicated by the user.

Figure 6:
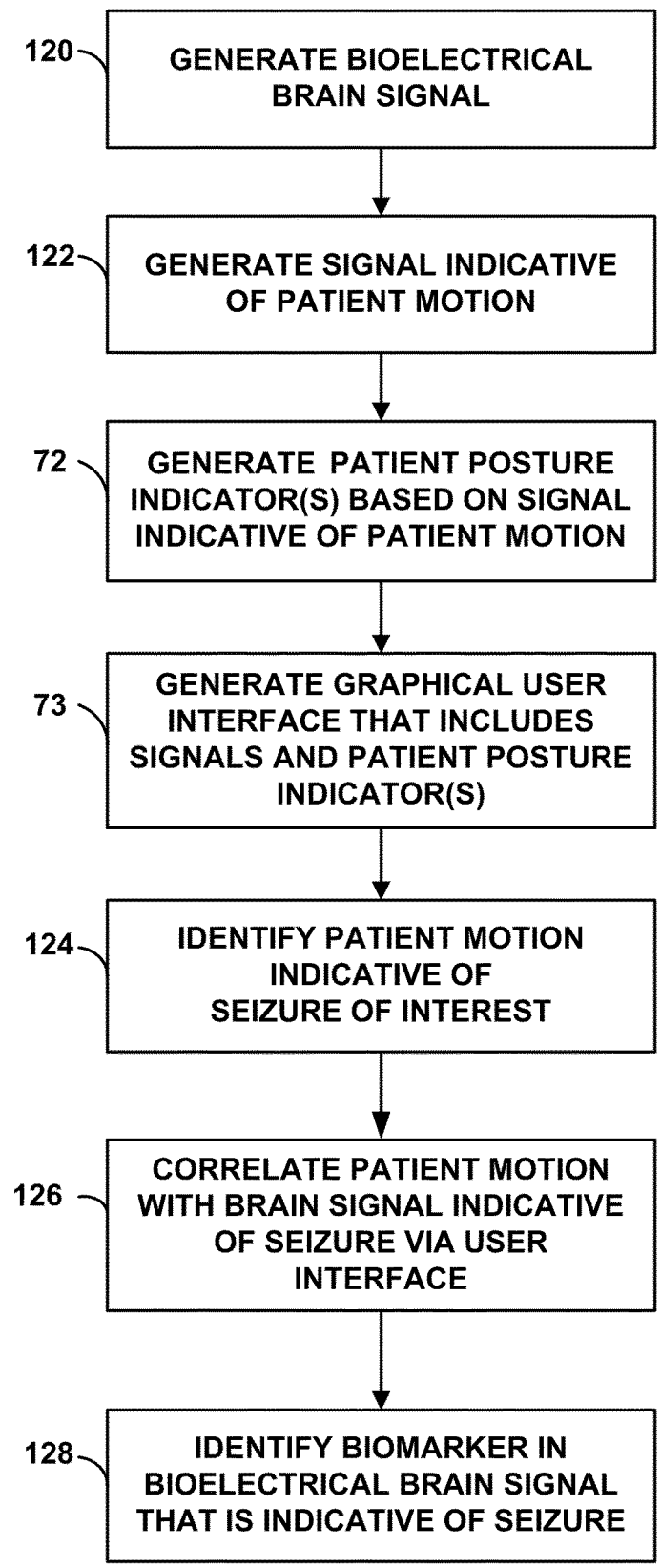
FIG. 6 is a flow diagram illustrating an example technique for identifying a biomarker indicative of a seizure based on a display that temporally correlates a bioelectrical brain signal of a patient and a patient motion signal.

FIG. 6 is a flow diagram of an example technique for determining a biomarker indicative of a seizure based on a graphical user interface (e.g., graphical user interface 67) that displays a bioelectrical brain signal of patient 12 and a patient motion data. The biomarker may be, for example, a mean, median, peak or lowest amplitude of bioelectrical brain signal within a particular segment, a frequency domain characteristic (e.g., the power level within a particular frequency band or a ratio of power levels within two frequency bands) or a particular pattern within a bioelectrical brain signal that regularly occurs during a seizure event of a patient. The technique is described with respect to user interface 67 presented by programmer 14 in FIG. 5. In other examples, however, the technique may be applicable to any user interface that illustrates a temporal correlation between a bioelectrical brain signal and graphical indicators of patient posture or motion. In addition, while FIG. 6 is primarily described with respect to programmer 14 and its components, in other examples, any part of the technique shown in FIG. 6 can be performed by another device.

In the technique shown in FIG. 6, sensing module 46 (FIG. 2) of IMD 16 generates bioelectrical brain signal 76 (120). As previously discussed, bioelectrical brain signal 76 is a signal that is indicative of electrical activity within brain 28 of patient 12. In general, bioelectrical brain signal 76 may include, but is not limited to, any one or more of an EEG signal, an ECoG signal, a LFP signal sensed from within one or more regions of a patient's brain, or a signal indicating action potentials from single cells within brain 28 of patient 12. In addition, in some examples, bioelectrical brain signal 76 includes a measured impedance of tissue of the brain of the patient.

Sensing module 46 can sense electrical activity within brain 28 of patient 12 via a selected subset of electrodes 24, 26 (FIG. 2) and generate bioelectrical brain signal 76 corresponding to the sensed electrical activity. IMD 16 may transmit sensed bioelectrical brain signal 76 to programmer 14, e.g., via wireless telemetry, and processor 60 of programmer 14 can generate and display graphical user interface 67 that includes the representation of bioelectrical brain signal 76.

Activity sensor 36 (or activity sensor 25) of therapy system 10 generates motion signal 78 (122). Motion signal 78 is a signal that is indicative of motion of patient 12. For example, activity sensor 36 can output signal 78 as patient 12 moves and changes postures. In some examples, e.g., the example illustrated in FIG. 5, activity sensor 36 may be a three-axis accelerometer that senses changes in the acceleration of patient 12 in three directions, e.g., x-axis direction, y-axis direction, and z-axis direction, and generates a component of patient motion signal 78 that corresponds to the changes in motion in each of the directions.

In some examples, processor 60 of programmer 14 generates patient posture indicators 80 (72) based on motion signal 78, as described above with respect to FIGS. 4A and 4B. Patient posture indicators 80 each provides a graphical representation of at least a portion of the body of patient 12 that corresponds to the posture state indicated by patient motion signal 78. Patient posture indicator 80 provides an indication to a user of the posture of patient 12 that may be more intuitive and recognizable than the raw patient motion signal 78.

After generating the one or more patient posture indicators, processor 60 generates graphical user interface 67 that temporally correlates bioelectrical brain signal 76 and the patient posture indicators (73). In addition, as described with respect to FIG. 4B, in some examples, processor 60 can also include patient motion signal 78 within graphical user interface 67, as shown in the example graphical user interface 67 of FIG. 5. Bioelectrical brain signal 76 and patient motion signal 78 can be displayed in graphical user interface 67 in a manner that illustrates a temporal correlation between the signals.

In some examples, graphical user interface 67 displayed on user interface 66 of programmer 14 may facilitate recognition of one or more characteristics of the bioelectrical brain signal 76 and/or the patient motion signal 78 that are indicative of a particular physiological event. In example technique of FIG. 6, processor 60 may display patient physiological data (e.g., signals 76, 78 and patient posture indicators 80) via graphical user interface 67 for seizure events, which are identified based on bioelectrical brain signal 76, patient input, or any combination of the two. Based on patient posture indicators 80, a user can relatively quickly identify patient motion that is indicative of a seizure of interest (124).

A seizure of interest can be particular type of seizure, e.g., a tonic-clonic seizure. As an example, a seizure of interest can be, for example, an electrographic seizure (as indicated by an EEG or an ECG signal) is associated with motor components (e.g., movement of patient 12 characteristic of a seizure). A seizure detected by detecting certain characteristics of sensed bioelectrical brain signal 76 may be referred to as an electrographic seizure. In some cases, an electrographic seizure is associated with motor component. During an electrographic seizure that is associated with a motor component, patient 12 may undergo motions, e.g., a repetitive motion, that are characteristic of a seizure rather than other patient motions (e.g., day-to-day activities such as walking, running, riding in a car, and the like). An electrographic seizure that is associated with a motor component is also referred to as a motor seizure. In contrast, an electrographic seizure that is not associated with a motor component may be referred to as a sensory seizure. In some cases, the user may determine that a detected seizure was severe if the seizure was associated with a relatively high activity level (e.g., indicating a convulsive seizure or a motor seizure) or associated with a sudden change in posture (e.g., indicating a fall). Thus, these types of seizures may be categorized as a seizure of interest.

In some examples, a user may view patient posture indicators 80 of graphical user interface 67 and determine that a particular patient motion occurred, e.g., a fall, at a particular point in time based on the patient posture indicators 80 that graphically represent the fall (e.g., by illustrating a patient figure that is in an upright position in one time frame and in a lying down position in an immediately subsequent time frame). In some examples, the user may provide input to user interface 66 in order to denote, e.g., highlight, the patient posture indicators 80 that are indicative of the seizure of interest.

In other examples, processor 60 of programmer 14 may automatically identify one or more patient posture indicators 80 that indicate the seizure of interest. For example, processor 60 may execute an algorithm that analyzes patient posture indicators 80 or patient motion signal 78 and determines that a particular patient motion of interest has occurred, e.g., by comparing the patient posture indicators 80 or patient motion signal 78 to a previously-defined template associated with the motor activity corresponding to the seizure of interest. Processor 60 can then generate and display a visual marker, e.g., by highlighting, the portion of patient motion signal 78 or the patient posture indicators 80 that includes the patient motion of interest. In some examples, processor 60 automatically filter patient data that is displayed via graphical user interface 67 such that only segments of data that include a patient motion of interest are displayed.

After patient motion indicative of a seizure of interest has been identified, e.g., identified visually by the user or automatically by processor 60 of programmer 14, a user may view graphical user interface 67 which temporally correlates bioelectrical brain signal 76 and patient posture indicators 80, and identify the segment of bioelectrical brain signal 76 that is temporally correlated with the patient motion indicative of the seizure of interest (126). In this way, processor 60 or the user can temporally correlate the relevant patient posture indicators 80 indicative of the seizure of interest with the segment of bioelectrical brain signal 76 indicative of the electrographic activity of brain 28 of patient 12 at the time the seizure of interest occurred.

In some examples, particularly in examples in which programmer 14 automatically identifies and denotes, e.g., highlights, the patient motion data displayed via graphical user interface 67 that may be indicative of the seizure of interest, processor 60 of programmer 14 may also generate and display a visual marker that denotes the temporally corresponding segment of bioelectrical brain signal 76. For example, processor 60 can control the position of sliding window 88 (FIG. 5) within graphical user interface 67 and align sliding window with the patient posture indicators 80 (and, if relevant, the motion signal 78) that indicate the seizure of interest.

In the technique shown in FIG. 6, a user, e.g., a clinician, identifies a biomarker within the segment of bioelectrical brain signal 76 that is indicative of the seizure of interest based on the patient data included in graphical user interface 67 (128). For example, the user may readily identify that the displayed bioelectrical brain signal 76 exhibits an abnormal characteristic (e.g., a relatively abrupt change in amplitude or frequency) during a time period immediately preceding the patient motion indicative of the seizure of interest. This abnormal characteristic can then be characterized as the biomarker of bioelectrical brain signal 76 that is indicative of the seizure of interest.

In other examples, processor 60 automatically determines the bioelectrical brain signal characteristic (e.g., an amplitude, frequency, pattern or other time domain or frequency characteristic) that is indicative of the seizure of interest (128). Processor 60 can determine the biomarker based on the segment of bioelectrical brain signal 76 temporally correlated with patient posture indicators 80 indicative of the patient motion associated with the seizure of interest. In some cases, more than one seizure of interest may need to be viewed on graphical user interface 67 in order to determine the biomarker that is indicative of the seizure of interest (128). Patient data from multiple seizures of interest can be useful for confirming that the selected biomarker is indicative of the seizure of interest, or even identifying which bioelectrical brain signal characteristic of a plurality of signal characteristics is revealing of the seizure of interest. For example, processor 60 or the user may select, as the biomarker, a particular characteristic of bioelectrical brain signal 76 that precedes the occurrence of the seizure of interest in a majority, if not all, of the occurrences of the seizures of interest.

Identifying occurrences of the seizure of interest based on a biomarker determined based on bioelectrical brain signal 76 can be useful for various purposes. In some examples, processor 60 of programmer 14 stores the biomarker in memory 62 or transmits the biomarker to IMD 16 for storage in memory 62. IMD 16 or programmer 14 can automatically detect the seizure of interest based on a sensed bioelectrical brain signal by detecting the presence of the biomarker within the sensed bioelectrical brain signal. The automatic detection of the seizure by IMD 16 or programmer 14 can be useful for patient monitoring purposes, such as for diagnosing the seizure disorder of patient 12, generating a log that indicates the types and frequencies of seizures that occur, and the like.

In addition, in some examples, the automatic detection of the seizure by IMD 16 or programmer 14 can be used to automatically control therapy delivery to patient 12. For example, processor 40 of IMD 16 can automatically select a particular therapy program from memory 42 upon detecting the seizure of interest, where the therapy program includes therapy parameter values selected to help mitigate or even prevent the onset of the seizure of interest. As another example, processor 40 of IMD 16 can automatically select a seizure detection algorithm from memory 42 upon detecting that the seizure of interest has occurred. The occurrence of the seizure of interest may indicate that the currently implement seizure detection algorithm is not effective because, for example, processor 40 is not controlling therapy delivery to mitigate or event prevent the seizure of interest in a timely manner.

In some examples, the user may provide input to user interface 66 indicating that a particular biomarker, e.g., a particular pattern of signal amplitudes and/or frequencies, within bioelectrical brain signal 76 is indicative of a particular type of seizure. Processor 60 may, consequently, associate the particular biomarker with the particular type of seizure within a memory, e.g., memory 42 or memory 62. In some examples, a user may interact with graphical user interface 67 to provide input requesting that only seizure events comprising the seizure of interest be viewed. Processor 60 can filter the patient data based on the determined biomarker, such that only segments of patient data that include the particular biomarker are presented in graphical user interface 67. That is, processor 60 may only display segments of patient data which are associated with the particular biomarker within the memory.

In the example technique shown in FIG. 6, processor 60 first determines whether an electrographic seizure occurred and then identifies patient posture indicators 80 that indicate patient motion that is indicative of the seizure of interest. In other examples, a user or processor 60 of programmer 14 can first identify the patient motion that is indicative of the seizure of interest via the displayed patient posture indicators 80 and subsequently determine whether bioelectrical brain signal 76 is indicative of a seizure. For example, processor 60 can compare bioelectrical brain signal 76 with a threshold or template that is indicative of a seizure. If bioelectrical brain signal 76 exhibits abnormal activity indicative of a seizure, processor 60 (or the user) can temporally correlate bioelectrical brain signal 76 with the motion of interest (e.g., a fall) (126) and identify a biomarker in bioelectrical brain signal 76 that is indicative of the seizure of interest (128).

Figure 7:
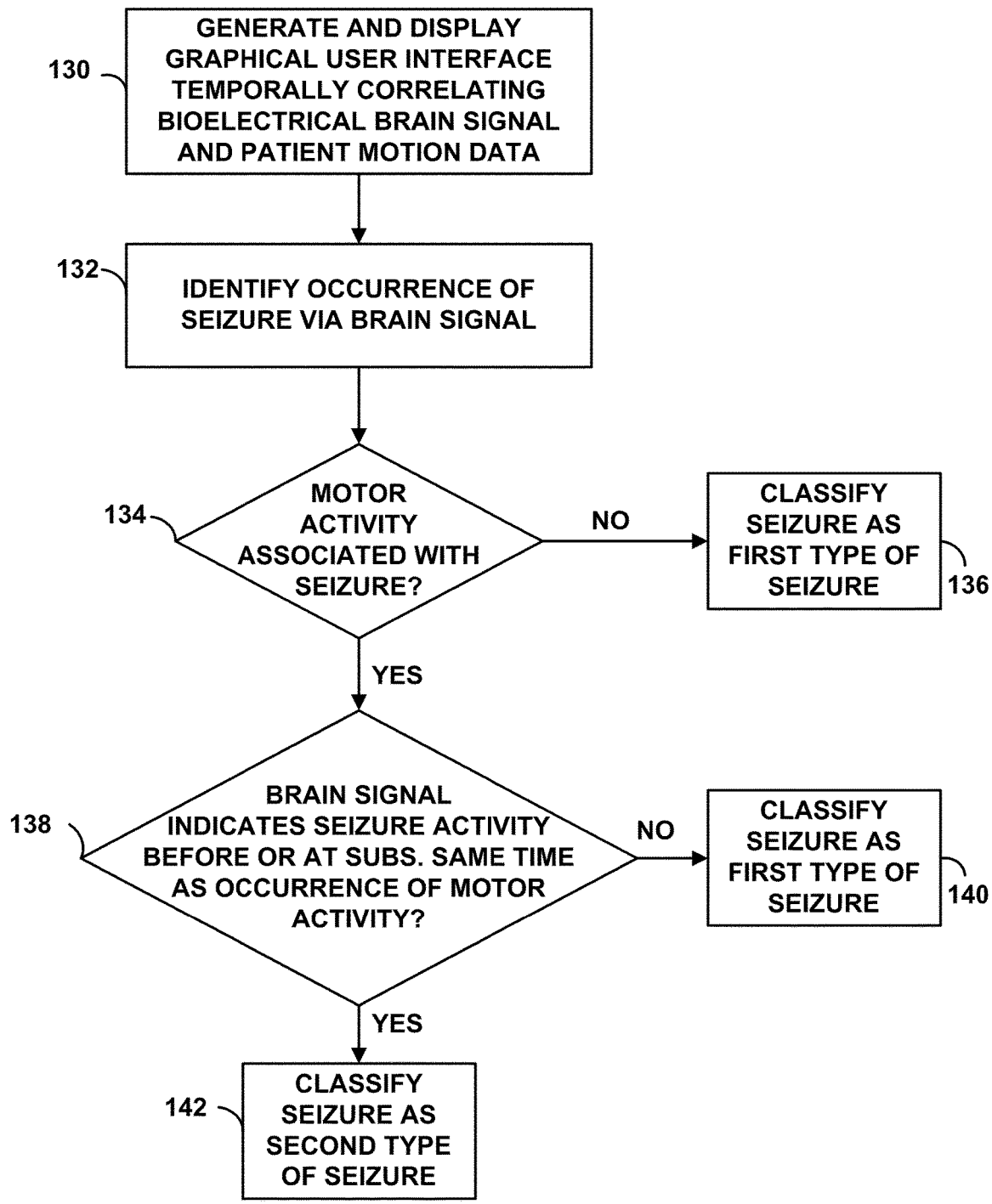
FIG. 7 is a flow diagram illustrating an example technique for classifying a seizure as a particular type of seizure based on the data displayed on user interface that illustrates a temporal correlation between a bioelectrical brain signal and a signal indicative of patient motion.

FIG. 7 is a flow diagram of an example technique that includes classifying a seizure as a particular type of seizure based on the data included in graphical user interface 67 and displayed on user interface 66 of programmer 14. As described above, graphical user interface 67 includes bioelectrical brain signal 76 and patient posture indicators 80 that provide a graphical representation of the patient posture state at periods of time temporally correlated with the bioelectrical brain signal 76. In addition, in the example shown in FIG. 5, graphical user interface 67 includes patient motion signal 78, which is visually temporally correlated with bioelectrical brain signal. While processor 60 of programmer 14 is primarily referred to throughout the description of FIG. 7, in other examples, a processor of another device can perform any part of the technique shown in FIG. 7.

In the technique illustrated in FIG. 7, processor 60 of programmer 14 generates graphical user interface 67 that temporally correlates the representation of bioelectrical brain signal 76 and patient posture indicators 80 (130). The user may view bioelectrical brain signal 76 shown in graphical user interface 67 in order to identify one or more segments of bioelectrical brain signal 76 that are indicative of brain activity associated with a seizure within brain 28 of patient 12, referred to herein as an electrographic seizure (132). For example, the user may scroll through various portions of bioelectrical brain signal 76, e.g., using controls 104 and 106, in order to identify portions of bioelectrical brain signal 76 that may be indicative of seizure activity within brain 28. In other examples, a seizure detection algorithm executed by processor 60 may identify segments of bioelectrical brain signal 76 that may be indicative of seizure activity and automatically include the relevant segments of bioelectrical brain signal In graphical user interface 67 that are displayed via a display of user interface 66 of programmer 14.

The user may view one or more particular segments of bioelectrical brain signal 76 that include activity indicative of seizure and identify the one or more patient posture indicators 80 that are temporally correlated with the particular segments of bioelectrical brain signal 76. The user may determine whether motor activity associated with the electrographic seizure, as indicated by one or more temporally correlated patient posture indicators 80, indicate a seizure of interest (e.g., a motor seizure or a convulsive seizure) occurred (134). That is, the user may view the segment of bioelectrical brain signal 76 that includes an indicator of seizure and the one or more patient posture indicators 80 that are temporally correlated with the segment of bioelectrical brain signal 76. The user may determine whether the graphical representation of the patient posture state indicated by the one or more patient posture indicators 80 indicate a particular type of motor activity occurred during the electrographic seizure.

If the one or more patient posture indicators 80 temporally correlated with the segment of bioelectrical brain signal 76 indicating the seizure activity do not indicate the motor activity of interest occurred, the user characterizes the seizure as a first type of seizure (136). In this example, the first type of seizure can be, for example, a seizure that does not include a motor component, such as a sensory seizure.

If, on the other hand, graphical user interface 67 displays one or more patient posture indicators 80 that indicate the occurrence of the motor activity of interest (e.g., a fall or convulsions) temporally correlated with the segment of bioelectrical brain signal 76 indicating the seizure activity, the user may determine whether the bioelectrical brain signal 76 indicates seizure activity began before or at substantially the same time as the occurrence of the motor activity (138). For example, the user may determine whether the electrographic seizure indicated by bioelectrical brain signal 76 is displayed first in time (e.g., up to thirty minutes before, such as about one to about ten minutes before, or within another pre-determined window of time) or at substantially the same time as (e.g., within a few seconds of, such as within one second of) the one or more patient posture indicators 80 that graphically indicate the motor activity of interest (e.g., as indicated by time indicator 82 of graphical user interface).

If the user determines via graphical user interface 67 that the seizure activity indicated by bioelectrical brain signal 76 began substantially after (e.g., more than at least one second after) the motor activity indicated by patient posture indicators 80 began, i.e., that the motor activity began substantially before the seizure activity began and is considered unrelated, the user classifies the seizure as the first type of seizure (140). As discussed above, in the example shown in FIG. 7, the first type of seizure is a seizure that does not include a motor component, e.g., a sensory seizure. Thus, if the user determines that the motor activity began substantially before the seizure activity, the user may determine that the seizure activity did not cause the motor activity. If, on the other hand, the user determines based on bioelectrical brain signal 76 and patient posture indicators 80 shown via graphical user interface 67 that the seizure activity within bioelectrical brain signal 76 began before or at substantially the same time as the motor activity indicated by one or more patient posture indicators 80 began, the user may characterize the seizure as a second type of seizure (142). In the example shown in FIG. 7, the second type of seizure can be a seizure that includes a motor component, e.g., a motor seizure or a convulsive seizure.

As discussed above, in most examples, the user may classify a seizure as a second type of seizure, e.g., a seizure with a motor component, if graphical user interface 67 indicates that seizure activity within bioelectrical brain signal 76 occurred before or at substantially the same time as motor activity indicated by one or more patient posture indicators 80. However, in other examples, motor activity indicated by one or more patient posture indicators 80 may precede the appearance of seizure activity in bioelectrical brain signal 76, but may be related to the seizure activity. For example, in some examples, sensing electrodes 24, 26 may be positioned within a portion of brain 28 that is away from the portion of brain 28 in which the seizure activity occurred. Consequently, the sensing electrodes 24, 26 may not have detected the seizure activity at exactly the moment in which the activity occurred. In some examples, the user may determine that the motor activity was related to the seizure activity if the seizure activity began within a particular predetermined period of time of the initial motor activity, e.g., within about two seconds of when the motor activity began, or within another pre-determined window of time.

Motor activity and seizure activity indicated by bioelectrical brain signal 76 can be considered related when the motor activity of interest and seizure activity of interest occur within a particular time range of each other. In some patients, an electrographic seizure as indicated by seizure activity within bioelectrical brain signal 76, can occur at substantially the same time as the corresponding motor activity. However, in other patients or even within the same patients at a different time, the electrographic seizure can precede the occurrence of related motor activity or other behavioral activity related to the seizure by several seconds to a minute or even several minutes (e.g., 2 minutes to about 30 minutes or more). Thus, in some examples, the user may classify a seizure as a second type of seizure, e.g., a seizure with a motor component, if graphical user interface 67 indicates that seizure activity within bioelectrical brain signal 76 occurred within a certain time range (e.g., about one second to about 30 minutes or more) as motor activity indicated by one or more patient posture indicators 80.

Although FIG. 7 illustrates a technique that involves classifying a seizure as a sensory seizure or a motor seizure, other examples include classifying a seizure in a different way. For example, other examples may involve more specifically classifying a seizure, such as classifying a seizure as a tonic-clonic seizure, a myoclonic seizure, an atonic seizure, or the like based on viewing bioelectrical brain signal 76 and patient posture indicators 80 that are temporally correlated on graphical user interface 67.

Moreover, in some examples, the classification of the seizures can be automatically performed by processor 60 based on input provided by a user. The user can provide input, for example, identifying a segment of bioelectrical brain signal 76 that indicates an occurrence of an electrographic seizure or input characterizing the type of motor activity indicated by patient posture indicators 80. User interpretation of patient posture indicators 80 can be useful for characterizing the motor activity as, e.g., a fall, convulsive activity, and the like.

As discussed above, a seizure associated with a motor component can be relatively debilitating or at least inconvenient for patient 12. In some examples, programmer 14 (or another device) provides a patient alert (e.g., a notification) that notifies patient 12 that a motor seizure is imminent. In order to provide an alert that is meaningful, the alert may be timed to give patient 12 sufficient time to take an appropriate action that may, in some examples, ensure the safety of patient 12 during the seizure event. However, depending on the type of seizure, there may not be sufficient time to give patient 12 a meaningful alert.

In accordance with some techniques, processor 60 of programmer 14 determines the types of seizures for which an alert is desirable, such as by determining the biomarker indicative of a motor seizure (e.g., as described with respect to FIG. 6). Processor 60 also determines which motor seizures (e.g., as identified by the corresponding biomarker) exhibit a sufficient latency between the onset of the electrographic seizure and the onset of motor activity. The duration of the latency may indicate whether there is sufficient time for programmer 14 to provide patient 12 with an alert. For example, a relatively short latency (e.g., less than about one second) may not provide programmer 14 with enough time to provide patient 12 with a meaningful alert. On the other hand, a relatively long latency (e.g., about fifteen minutes to about thirty minutes) can provide enough time for programmer 14 to provide patient 12 with an alert and for patient 12 to take a responsive action.

Figure 8:
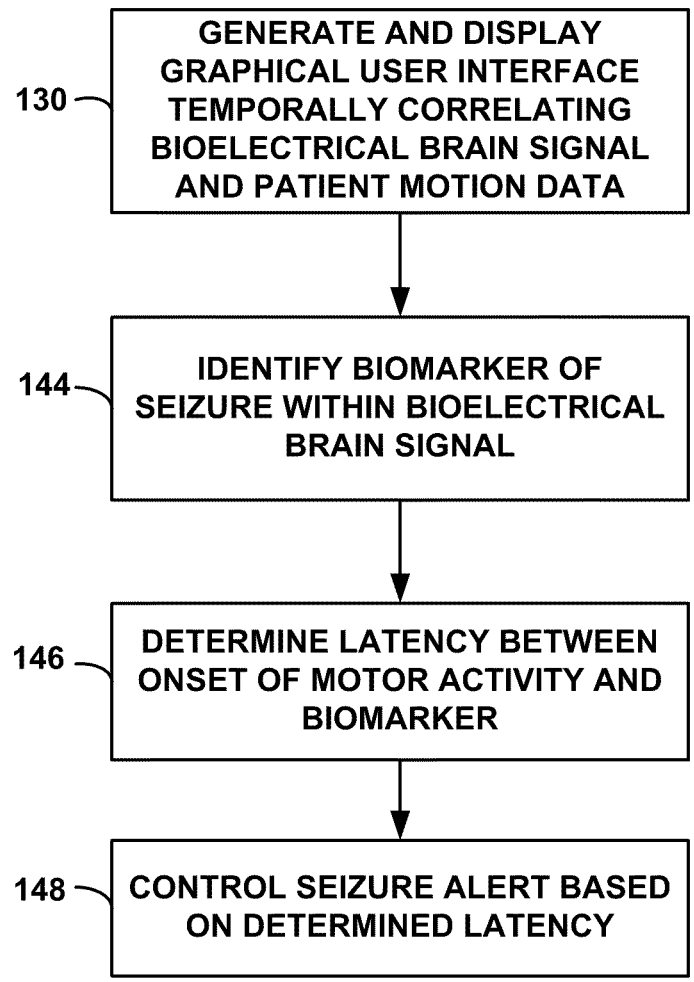
FIG. 8 is a flow diagram illustrating an example technique for identifying a latency between onset of seizure activity within a bioelectrical brain signal and onset of motor activity within a signal indicative of patient motion.

FIG. 8 is flow diagram illustrating an example technique for identifying a latency, e.g., a time delay, between onset of seizure activity identified based on bioelectrical brain signal 76 and onset of motor activity identified based on patient posture indicators 80. The technique shown in FIG. 8 is described with respect to programmer 14. However, in other examples, a processor of another device can perform any part of the technique shown in FIG. 8. In addition, in some examples, at least part of the technique shown in FIG. 8 is implemented based on user input.

Processor 60 of programmer 14 generates and displays graphical user interface 67 via a display of user interface 66, where graphical user interface 67 temporally correlates bioelectrical brain signal 76 with patient motion data (e.g., patient posture indicators 80) (130). Processor 60, alone or with the input from a user, identifies one or more segments of bioelectrical brain signal 76 that include a biomarker indicative of seizure activity within brain 28 of patient 12 (144). In the example described with respect to FIG. 8, the biomarker indicative of seizure is observed within bioelectrical brain signal 76 prior to a change in patient posture state as indicated by patient posture indicators 80. For example, the seizure activity within brain 28 occurred before a change in patient motion or posture was induced.

Processor 60, alone or with the input from a user, determines the amount of time between the onset of electrographic seizure activity indicated by bioelectrical brain signal 76 and the onset of motor activity (146). For example, the user may use a time indicator, e.g., time indicator 82 of FIG. 5, as a reference to determine the latency, e.g., time delay, between a biomarker indicative of seizure activity and a patient posture indicator 80 that indicates the onset of a particular motor activity. The user can then provide input via user interface 66 that indicates the determined amount of time. As another example, the user can provide input to processor 60 that marks the biomarker indicative of electrographic seizure activity and the patient posture indicator 80 that indicates the onset of the particular motor activity, and processor 60 can automatically determine the amount of time between the onset of the electrographic seizure and the onset of the motor activity (e.g., as indicated by the time at which a posture change occurred).

Processor 60 determines the latency between onset of seizure activity within bioelectrical brain signal 76 and the onset of motor activity indicated by patient posture indicator 80 based on a plurality of seizure occurrences. For example, processor 60 may determine the latency for a plurality of seizure events and select the mean, median, highest or lowest latency as indicative of the latency between the onset of an electrographic seizure and the onset of motor activity for a particular type of seizure.

Processor 60 can store the determined latency in memory 62 (or a memory of another device) and control the delivery of a seizure alert to patient 12 based on the latency (148). For example, processor 60 can generate and present an alert to patient 12 via user interface 66 of programmer 14, whereby the alert notifies patient 12 that motor activity resulting from the occurrence of the seizure will occur in a particular amount of time. The alert can be, for example, a visual alert provided on a display of user interface 66, an auditory alert, or a somatosensory alert. In response to receiving the seizure alert, the patient 12 and/or the user may take appropriate actions that may, in some examples, ensure the safety of patient 12 during the seizure event. Providing patient 12 with a specific timeline for the onset of the motor activity can help patient 12 take any action necessary to prepare for the motor activity (e.g., sitting down, calling for help, stopping a car if patient 12 is driving, and the like). A motor seizure may place patient 12 in a compromising situation when patient 12 is engaged in certain activities, such as driving. Thus, programmer 14 that delivers a notification to patient 12 of the occurrence and imminent onset of motor activity from a seizure can be useful.

As previously mentioned, graphical user interface 67 may, in some examples, be useful for training a support vector machine or another type of supervised machine learning algorithm to automatically detect a particular patient state, e.g., a seizure, based on a sensed physiological signal. Commonly-assigned U.S. patent application Ser. Nos. 12/694,042 by Carlson et al., 12/694,053 by Denison et al., 12/694,044 by Carlson et al., and U.S. Ser. No. 12/694,035 by Carlson et al. describe patient state detection with a classification algorithm that is determined based on supervised machine learning.

As described by U.S. patent application Ser. Nos. 12/694,042 by Carlson et al., 12/694,053 by Denison et al., 12/694,044 by Carlson et al., and U.S. Ser. No. 12/694,035 by Carlson et al., supervised machine learning can be applied, for example, using a support vector machine (SVM) or other artificial neural network techniques. Supervised machine learning can be implemented to generate a classification boundary during a learning phase based on a feature vector, e.g., two or more feature values, of one or more patient parameter signals known to be indicative of the patient being in the patient state and a feature vector of one or more patient parameter signals known to be indicative of the patient not being in the patient state. A feature is a characteristic of the patient parameter signal, such as an amplitude or an energy level in a specific frequency band. The classification boundary delineates the feature values indicative of the patient being in the patient state and the feature values indicative of the patient not being in the patient state.

Once the classification boundary is determined based on the known patient state data, processor 40 of IMD 16 or another device (e.g., processor 60 of programmer 14) can automatically determine a patient state by determining the side of the classification boundary on which a feature vector extracted from a sensed patient parameter signal lies. The patient state detection may be used to control various courses of action, such as controlling therapy delivery, generating a patient notification, or evaluating a patient condition. In addition, various metrics for monitoring and evaluating a patient condition can be determined based on the classification boundary and a signal indicative of a patient parameter.

Graphical user interface 67 may be useful for training a support vector machine or another type of supervised machine learning algorithm, e.g., by receiving user input that allows processor 60, to generate a classification boundary. FIG. 9 is a flow diagram of an example technique for generating a classification boundary via a support vector machine-based algorithm or another supervised machine learning-based algorithm based on training vectors determined via graphical user interface 67. The technique shown in FIG. 9 is described with respect to programmer 14. However, in other examples, a processor of another device can perform any part of the technique shown in FIG. 9. In addition, in some examples, at least part of the technique shown in FIG. 9 is implemented based on user input.

Processor 60 of programmer 14 generates and displays graphical user interface 67 via a display of user interface 66, where graphical user interface 67 temporally correlates bioelectrical brain signal 76 with patient motion data (e.g., patient posture indicators 80) (150). A user views the patient data displayed on graphical user interface 67 and provides input via, e.g., user interface 66 of programmer 14 that indicates a particular segment of a physiological signal, e.g., bioelectrical brain signal 76, that is associated with a patient event (e.g., a seizure or a particular motor activity) of interest.

Processor 60 receives and processes the user input indicating a particular segment of the physiological signal (152). For example, the user may be particularly interested in seizure events of patient 12. The user may identify via graphical user interface 67 one or more segments of bioelectrical brain signal 76 associated with a seizure event based on one or more particular characteristics that are recognized by the user as being indicative of seizure activity within brain 28 of patient 12. The user may provide input, e.g., via a stylus or a finger, to select the one or more segments of bioelectrical brain signal 76 indicative of seizure activity. As another example, the user may provide input by indicating the time indicator 83 that corresponds to the time at which the segment of interest of the physiological signal occurred. Processor 60 receives the user input indicating one or more segments of interest of the physiological signal.

As mentioned above, a support vector machine or another supervised machine learning algorithm generates a classification boundary based on data indicative of the patient being in a particular patient state and data indicative of the patient not being in the particular patient state. Thus, in the example technique illustrated in FIG. 9, a user provides input to select one or more segments of the physiological signal, e.g., bioelectrical brain signal 76, that are not indicative of the patient event of interest. Processor 60 receives the user input indicating segments of the physiological signal that are not associated with the patient event of interest (154). For example, in examples in which the user is interested in seizure activity of patient 12, the user may provide input indicating one or more segments of bioelectrical brain signal 76 that do not indicate seizure activity, and processor 60 receives the user input.

After receiving both the user input indicating segments of the physiological signal that are associated with the patient event of interest (152) and the user input indicating segments of the physiological signal that are not associated with the patient event of interest (154), processor 60 determines distinguishing characteristics of the segments of patient data associated with the patient event of interest and the segments of patient data not associated with the patient event of interest (156). For example, after receiving user input indicating segments of bioelectrical brain signal 76 that are associated with seizure activity and user input indicating segments of bioelectrical brain signal 76, processor 60 analyzes each of the segments of bioelectrical brain signal 76 and determines one or more characteristics that distinguish the segments of bioelectrical brain signal 76 associated with seizure activity from the segments of bioelectrical brain signal 76 not associated with seizure activity. For example, in some examples the one or more distinguishing characteristics may include a particular characteristic of a physiological signal, e.g., the amplitude or frequency of bioelectrical brain signal 76. That is, as an example, processor 60 may determine that segments of bioelectrical brain signal 76 identified by a user as indicative of seizure generally exhibit a higher frequency than segments of bioelectrical brain signal 76 identified by a user as not indicative of seizure.

In some examples, after receiving user input indicating segments of bioelectrical brain signal 76 that are associated with seizure activity and user input indicating segments of bioelectrical brain signal 76, processor 60 can determine one or more characteristics of the segments of patient motion signal 78 corresponding to the user-identified segments of bioelectrical brain signal 76. In addition, processor 60 can determine one or more characteristics that distinguish the segments of patient motion signal 78 associated with seizure activity from the segments of patient motion signal 78 not associated with seizure activity. In this way, processor 60 can train a support vector machine or another supervised machine learning technique based on two different types of patient data.

After determining one or more distinguishing characteristics of segments of patient data associated with the patient event of interest and/or one or more distinguishing characteristics of segments of patient data not associated with the patient event of interest, processor 60 determines one or more training vectors for training the support vector machine or the other supervised machine learning algorithm based on the plurality of segments of patient data associated with the patient event and the plurality of segments of patient data not associated with the patient event (158). For example, if processor 60 determines that segments of bioelectrical brain signal 76 identified by a user as indicative of seizure generally exhibit a higher frequency than segments of patient motion signal 78 temporally correlated to segments of bioelectrical brain signal 76 identified by a user as not indicative of seizure, processor 60 may determine particular values for the frequency of segments of patient motion signal 78 associated with seizure activity and segments of patient motion signal 78 not associated with seizure activity. The particular values for the frequency of various segments of patient motion signal 78 may comprise a training vector. The training vector can include values for any suitable number of features, such as two, three or more. As discussed above, each feature comprises a different characteristic, such as the energy level within a respective frequency band.

Processor 60 generates a classification boundary based on the training vectors (160). The classification boundary may be used to identify when patient 12 is or is not experiencing the patient event of interest. That is, processor 60 generates a classification boundary that specifies particular values of one or more distinguishing characteristics of patient data. The classification boundary delineates the particular values of the distinguishing characteristics that are indicative of patient 12 experiencing the patient event of interest and the particular values of the distinguishing characteristics that are indicative of patient 12 not experiencing the patient event of interest. Processor 60 may use the classification boundary to identify future occurrences of the patient event of interest, e.g., to more effectively treat a disorder of patient 12, to identify the frequency of the patient event of interest, and the like. Processor 60 may, in some examples, identify, e.g., highlight (e.g., with a window or a different color) or mark in some other manner, segments of patient data indicative of the patient event via graphical user interface 67 based on the classification boundary in order that a user may more easily identify patient data of interest.

The classification boundary may be linear or non-linear. Techniques for generating linear and nonlinear classification boundaries are described in U.S. patent application Ser. Nos. 12/694,042 by Carlson et al., 12/694,053 by Denison et al., 12/694,044 by Carlson et al., and U.S. Ser. No. 12/694,035 by Carlson et al., which were previously incorporated by reference in their entireties.

Some patients periodically experience behavioral events during which the patients may suddenly and temporarily lose consciousness, e.g., fall events. Behavioral events may be caused by a number of different patient disorders. For example, in some examples, fall events may be associated with abnormal activity within brain 28 of patient 12, e.g., seizure activity. In other examples, fall events may be associated with another patient condition, such as syncope. Syncope may occur relatively infrequently and fall events associated with syncope may have a relatively short duration and/or a relatively sudden onset. Syncope can be triggered by a variety of patient conditions such as, in some examples, a neurocardiogenic syndrome, which may be a disregulation of the peripheral and/or central autonomic nervous system. Neurocardiogenic syncope may also be referred to as neurogenic syncope, vasovagal syncope, or neutrally mediated syncope. In some examples, neurocardiogenic syndrome may cause anoxia, e.g., a decrease in the level of oxygen of patient 12, which may lead to syncope. In other examples, syncope can be triggered by a cardiac arrhythmia, such as bradycardia, tachycardia, etc., that may lead to a fall event. In some examples, syncope associated with a neurocardiogenic syndrome can also lead to a seizure.

Fall events associated with syncope may be misdiagnosed as fall events associated with seizures because of similarities in the motor activity associated with different types of behavioral events, e.g., loss of consciousness. For example, in some examples, a fall event associated with syncope triggered by a cardiac arrhythmia in the heart of patient 12 may have characteristics similar to a fall event associated with seizure activity in brain 28 of patient 12.

A device that senses a bioelectrical brain signal of patient 12, a cardiac signal of patient 12, and patient motion may be a useful tool for long-term monitoring of patient 12 in order to help diagnose the source of a behavioral event of patient 12, e.g., a fall event of an unknown cause, convulsive events, and the like. In order to present the physiological information in a meaningful way, programmer 14 or another computing device can generate and display a graphical user interface that displays a representation of a bioelectrical brain signal of patient 12, a cardiac signal, and patient motion data (e.g., patient motion signal 78 or patient posture indicators 80). Such a graphical user interface can present information with which a clinician can diagnose the source of the patient's behavioral event.

Figure 10:
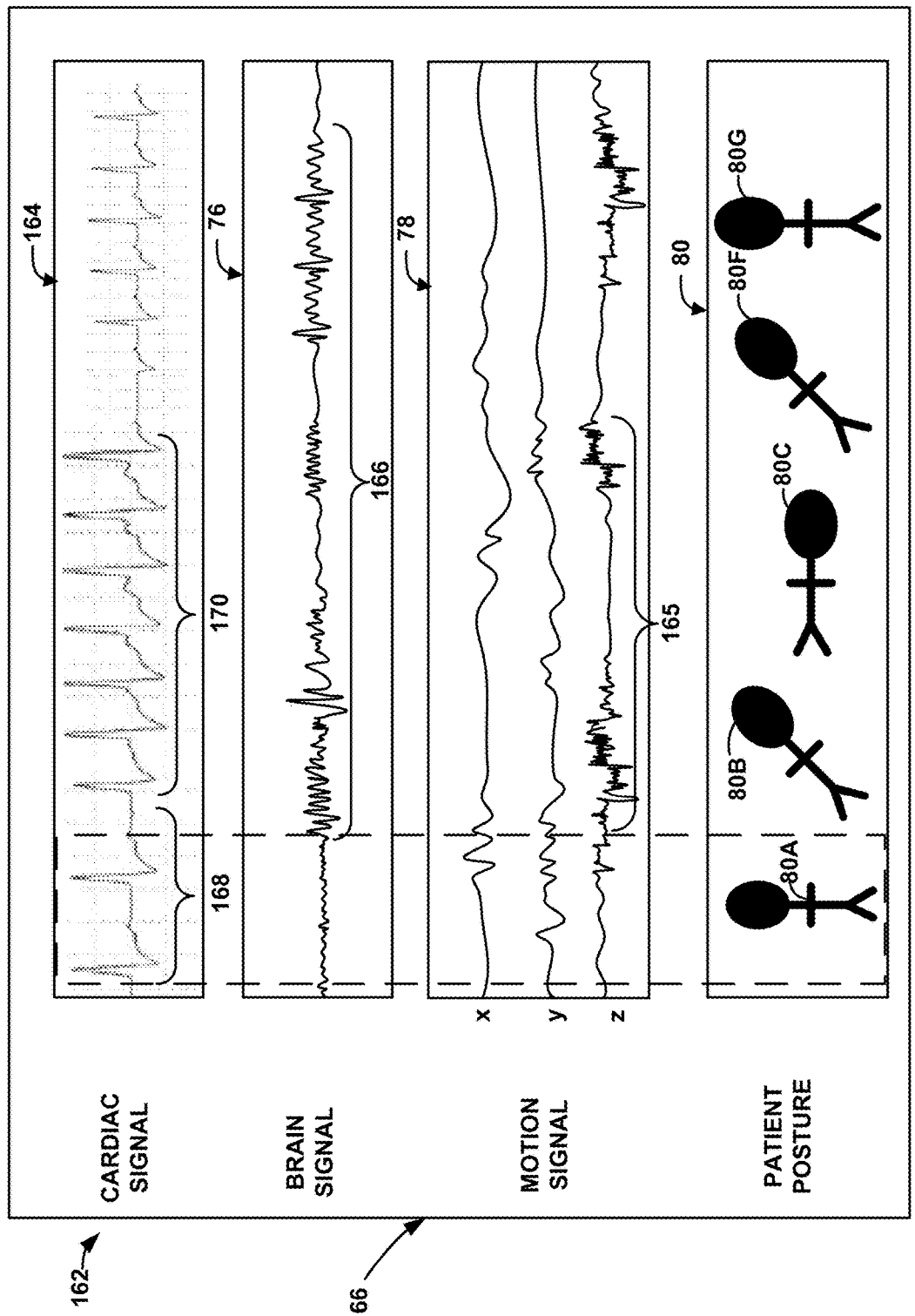
FIG. 10 is diagram illustrating an example user interface that temporally correlates a bioelectrical brain signal, a signal indicative of patient motion, and a signal indicative of cardiac activity.

FIG. 10 illustrates another example graphical user interface 162 (also illustrated in FIG. 5) generated by programmer 14 and presented on a display of user interface 66. Graphical user interface 162 includes a representation of bioelectrical brain signal 76 sensed by sensing module 46 of IMD 16, as well as temporally correlated patient posture indicators 80. In addition, graphical user interface 162 includes patient motion signal 78 generated by motion sensor 36, whereby signal 78 indicates patient motion, and cardiac signal 164. Graphical user interface 162 temporally correlates cardiac signal 164, bioelectrical brain signal 76, patient motion signal 78, and patient posture indicators 80 and provides a visual indication of the temporal correlation between the signals 164, 76, 78 by aligning the signals with each other.

Although various example system and methods are described herein, additional example systems and methods for obtaining and comparing cardiac signals and bioelectrical brain signals are described in commonly-assigned U.S. Patent Application Publication No. 2006/0135877 by Giftakis et al., entitled "SYSTEM AND METHOD FOR MONITORING OR TREATING NERVOUS SYSTEM DISORDERS" and filed on Dec. 19, 2005; U.S. Patent Application Publication No. 2007/0238939 by Giftakis et al., entitled "SYSTEM AND METHOD FOR MONITORING OR TREATING NERVOUS SYSTEM DISORDERS" and filed on Apr. 27, 2007, and U.S. Patent Application Publication No. 2007/0260289 by Giftakis et al., entitled "SYSTEM AND METHOD FOR USING CARDIAC EVENTS TO TRIGGER THERAPY FOR TREATING NERVOUS SYSTEM DISORDERS" and filed on Jun. 22, 2008. U.S. Patent Application Publication Nos. 2006/0135877 by Giftakis et al., 2007/0238939 by Giftakis et al., and 2007/0260289 by Giftakis et al. are herein incorporated by reference in their entireties.

Cardiac signal 164 may be any signal related to cardiac function of patient 12. In the example illustrated in FIG. 10, cardiac signal 164 is an electrogram (EGM) or an electrocardiogram (ECG) signal that represents the electrical activity of the heart of patient 12. Cardiac signal 164 may be generated by a sensor that senses electrical activity of the heart of patient 12 via one or more electrodes and generates signal 164 based on the sensed electrical activity. The cardiac activity sensor can be implanted within patient 12 and sense electrical activity of the heart via implanted electrodes or may be external to patient 12, and, e.g., sense electrical activity of the heart via external surface electrodes.

In some examples, sensing module 46 of IMD 16 generates cardiac signal 164 based on signals from a selected subset of electrodes 24, 26, or via another set of electrodes that are, e.g., positioned proximate heart 14 or at least not within cranium 32. The electrodes with which cardiac activity is sensed can be coupled to leads that extend from outer housing 34 of IMD 16 or can include electrodes on outer housing 34. Processor 40 of IMD 16 may transmit raw cardiac signal 164, a parameterized signal or another type of signal to processor 60 of programmer 14 for generation of graphical user interface 162.

In other examples, cardiac signal 164 can be generated by a sensor that is physically separate from IMD 16. For example, cardiac signal 164 can be generated by a relatively small ECG sensor (compared to IMD 16) that is implanted within a subcutaneous tissue layer of patient 12 or another tissue site, such as a submuscular location. An example of a cardiac monitoring device includes, but is not limited to, the Reveal Plus Insertable Loop Recorder, which is available from Medtronic, Inc. of Minneapolis, Minn. The cardiac sensor can be a temporary diagnostic tool employed to monitor one or more physiological parameters of patient 12 for a relatively short period of time (e.g., days or weeks), or may be used on a more permanent basis, such as to control therapy delivery to patient 12. In other examples, cardiac signal 164 may be generated by chemical sensors, biological sensors, pressure sensors, temperature sensors, or any other sensor capable of generating a signal indicative of cardiac function.

Graphical user interface 162 that includes cardiac signal 164 in addition to bioelectrical brain signal 76 and patient posture indicators 80 provides physiological information in a meaningful way for determining the cause of a particular behavioral event. Based on the physiological data presented in graphical user interface 162, a user can determine the time course of the behavioral event, brain activity, and cardiac activity, which can be revealing of the cause of the behavioral event. That is, whether or not a particular brain activity or cardiac activity occurred before or after the occurrence of the behavioral event, as indicated by graphical user interface 162, can indicate whether the brain activity or cardiac activity caused the behavioral event. For example, a user may identify the occurrence of a particular behavioral event, e.g., a fall event, via patient posture indicators 80 and/or patient motion signal 78. The user may observe the segments of bioelectrical brain signal 76 and cardiac signal 164 that temporally correspond to the patient posture indicators 80 and/or segment of patient motion signal 78 that includes the behavioral event. Based on the temporally correlated segments of brain signal 76 and cardiac signal 164, the user may determine whether the particular behavioral event was caused by brain activity, e.g., brain activity indicative of a seizure or by particular cardiac activity, e.g., an arrhythmia, of patient 12 via user interface 66.

In the example illustrated in FIG. 10, a user may view graphical user interface 162 and determine that a behavioral event of interest, e.g., a fall event, has occurred based on patient motion signal 78 and patient posture indicators 80. For example, patient motion signal 78 exhibits an increase in z-axis motion in segment 165. Patient posture indicators 80B, 80C, which processor 60 generated based on patient motion signal 78, provide a graphical representation of the behavioral event that occurred. A user may determine, based on segment 165 and patient posture indicators 80B, 80C that patient 12 suffered a fall event during the time period represented by the patient data displayed on user interface 66 in the example of FIG. 10. Patient posture indicators 80F, 80G indicate the end of the fall event, e.g., when patient 12 stood up after falling.

The user may observe the segments of bioelectrical brain signal 76 and cardiac signal 164 that temporally correlate to segment 165 of patient motion signal 78. The user may determine that bioelectrical brain signal 76 exhibits activity indicative of a seizure event in segment 166. The user may also determine that segment 168 of cardiac signal 164 represents normal cardiac activity while segment 170 represents arrhythmic cardiac activity (e.g., a tachycardia event or episode). The user may observe that the seizure activity represented by segment 166 begins prior to or at substantially the same time (e.g., within about one second or less) as the abnormal cardiac activity represented in segment 170. That is, prior to seizure activity within bioelectrical brain signal 76, patient 12 exhibited normal cardiac activity. Upon onset of seizure activity, patient 12 began to exhibit abnormal cardiac activity. Based on the observation, the user may determine that the abnormal cardiac activity was caused by the seizure activity and, consequently, that the behavioral event, e.g., the fall event, was caused by the seizure activity and not by the cardiac activity.

Figure 11:
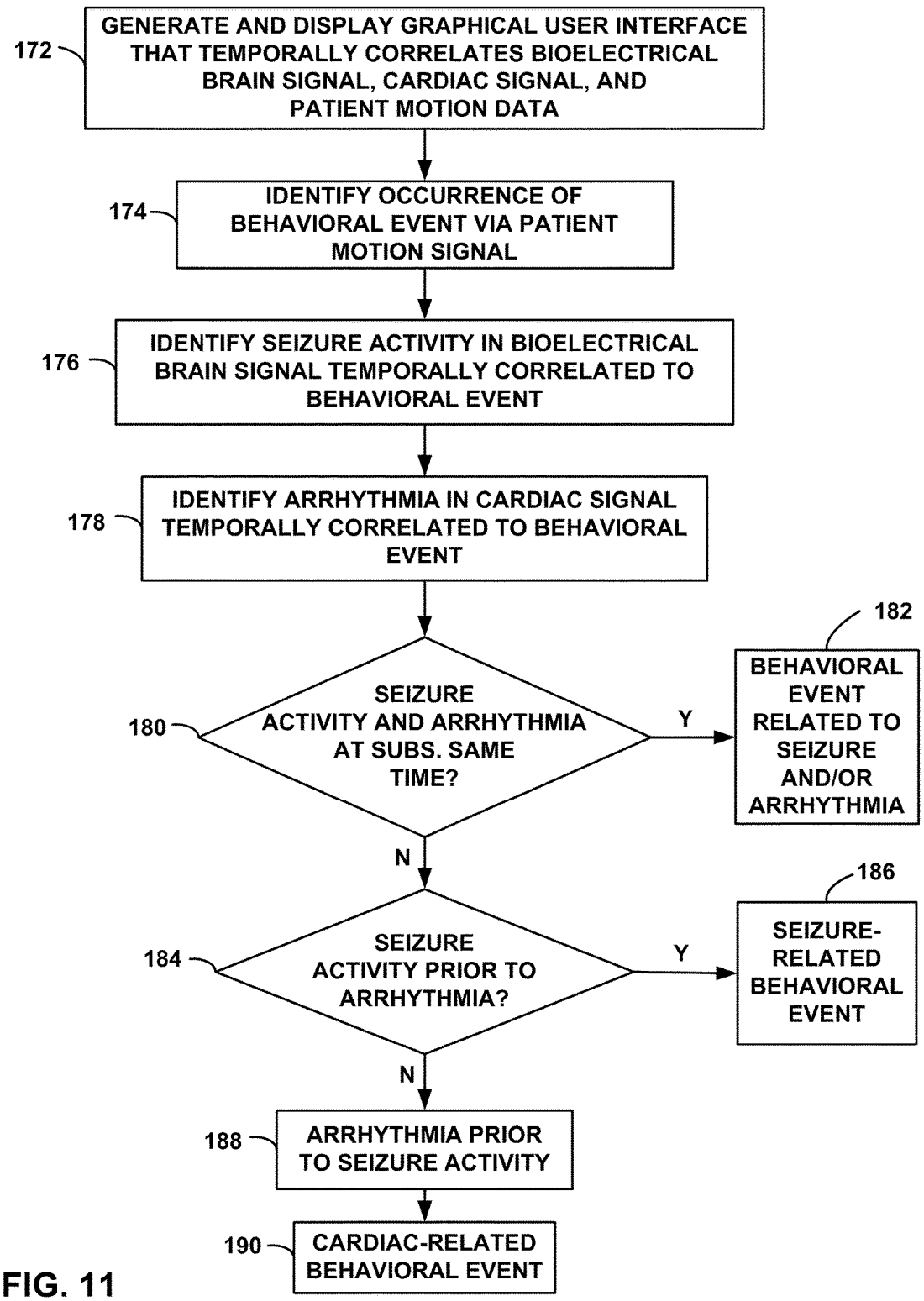
FIG. 11 is a flow diagram illustrating a technique that may be used to determine whether a behavioral event was caused by a cardiac-related condition or a seizure-related condition or both.

FIG. 11 is a flow diagram illustrating a technique for determining whether a behavioral event was caused by a cardiac-related condition or a seizure-related condition or both. While FIG. 11 is described as being performed by processor 60 of programmer 14, in other examples, a processor of another device can automatically perform any part of the technique shown in FIG. 11 alone or with the aid of a user.

Processor 60 of programmer 14, upon receiving bioelectrical brain signal 76, cardiac signal 164, and signal 78 indicative of patient motion from a device (e.g., IMD 16), generates graphical user interface 162 and displays graphical user interface 162 on a display of user interface 66 of programmer 14 (172). As described with respect to FIG. 10, graphical user interface 162 displays bioelectrical brain signal 76, cardiac signal 164, a patient motion signal 78, and patient posture indicators 80 in a manner that illustrates a temporal correlation between the physiological data. That is, graphical user interface 162 aligns bioelectrical brain signal 76, cardiac signal 164, patient motion signal 78, and patient posture indicators 80 on top of each other in a meaningful way. In this way, a segment of bioelectrical brain signal 76 represents data collected from patient 12 at the same time as data represented by the segment of cardiac signal 164 and the segment of patient motion signal 78 that are positioned directly beneath the segment of bioelectrical brain signal 76. In addition, patient posture indicator 80 positioned directly beneath patient motion signal 78 on graphical user interface 162 provides a graphical representation of at least a portion of the body of patient 12 to visually indicate the patient posture state in a meaningful way. In some examples, graphical user interface 162 does not include patient motion signal 78, while in other examples, graphical user interface 162 does not include patient posture indicators 80.

A user may view graphical user interface 162 and identify activity within patient motion signal 78 or a patient posture indicator 80 that is indicative of a particular behavioral event of patient 12 (174). For example, the user may determine that a particular segment of patient motion signal 78 or one or more patient posture indicators 80 indicates that patient 12 underwent a fall event or another behavioral event. In the example illustrated in FIG. 10, for example, the user may identify segment 165 of patient motion signal 76 and/or patient posture indicators 80B, 80C and determine that patient 12 underwent a fall event.

The user may, via user interface 66, provide input to programmer 14 identifying the occurrence of the behavioral event. For example, in response to a prompt generated by processor 60, the user may mark or highlight the segment of patient motion signal 78 or one or more patient posture indicators 80 that indicate that patient 12 underwent a fall event. Processor 60 automatically determines the segments of bioelectrical brain signal 76 and cardiac signal 164 that temporally correspond to the segment of patient motion signal 78 that illustrates the behavioral event. For example, processor 60 can generate a marker that identifies the corresponding segments of bioelectrical brain signal 76 and cardiac signal 164 and display the marker in graphical user interface 162. In other examples, the user visually ascertains the segments of bioelectrical brain signal 76 and cardiac signal 164 that temporally correspond to the segment of patient motion signal 78 that illustrates the behavioral event without the aid of processor 60.

Processor 60 determines whether the segment of bioelectrical brain signal 76 temporally correlated to the behavioral event detected based on patient motion signal 78 or patient posture indicators 80 is indicative of a seizure event. The segment of bioelectrical brain signal 76 that temporally corresponds to the behavioral event may include a biomarker or otherwise illustrate abnormal activity that occurred within brain 28 of patient 12 that indicates that patient 12 underwent a seizure during a similar time period in which the behavioral event occurred. Processor 60 can implement any suitable algorithm for determining whether the segment of bioelectrical brain signal 76 includes the activity indicative of seizure activity, such as the seizure detection algorithms described above. If processor 60 determines the segment of bioelectrical brain signal 76 is indicative of a seizure event, processor 60 identifies the activity within the segment of bioelectrical brain signal 76 that is indicative of seizure activity within brain 28 of patient 12 (176). In the example illustrated in FIG. 10, for example, processor 60 may identify a specific segment 166 of bioelectrical brain signal 76 as being indicative of seizure activity within brain 28. In some examples, processor 60 highlights segment 166 or otherwise marks segment 166. Segment 166 can be, for example, a sub-segment of the segment of bioelectrical brain signal 76 temporally correlated to the behavioral event detected based on patient motion signal 78 or patient posture indicators 80.

In some examples in which patient 12 experiences a behavioral event associated with syncope, patient 12 may experience a period of presyncope, which includes, e.g., symptoms of light-headedness, muscular weakness, and the like, directly prior to loss of consciousness associated with syncope. In these examples, bioelectrical brain signal 76 may exhibit particular characteristics that are indicative of and temporally correlated with the symptoms of presyncope exhibited by patient 12. For example, in some examples, during a period of presyncope, bioelectrical brain signal 76 of patient 12 may exhibit slowing of particular brain waves, e.g., theta or delta waves, and suppression of background brain activity. Processor 60 may analyze bioelectrical brain signal 76, e.g., using an algorithm, and highlight or otherwise mark particular segments of bioelectrical brain signal 76 that include characteristics generally indicative of a time period in which patient 12 experienced presyncope.

Processor 60 also determines whether the segment of cardiac signal 164 that temporally corresponds to the behavioral event is indicative of an arrhythmia within the heart of patient 12. Processor 60 can determine whether the segment of cardiac signal 164 is indicative of arrhythmia using any suitable arrhythmia detection technique. An arrhythmia event or episode, whether the event or episode is a bradycardia or tachycardia event or episode, may be determined, e.g., based on a duration of a cardiac cycle. A cardiac cycle duration may be, for example, measured between successive R-waves or P-waves of the EGM or ECG signal. This duration may also be referred to as an R-R or P-P interval.

If processor 60 determines that the segment of cardiac signal 164 that temporally corresponds to the behavioral event is indicative of an arrhythmia within the heart of patient 12, processor 60 identifies the portion of the cardiac signal 164 indicating the arrhythmia (178). In the example illustrated in FIG. 10, for example, processor 60 may identify segment 170 of cardiac signal 164 that is indicative of arrhythmia and that at least partially temporally corresponds to segment 165 of patient motion signal 76 and/or posture state indicators 80B, 80C. Segment 170 of cardiac signal 164 can be, for example, a sub-segment of the segment of cardiac signal 164 that is temporally correlated to the behavioral event detected based on patient motion signal 78 or patient posture indicators 80

Upon determining that a behavioral event occurred, along with abnormal brain activity and abnormal cardiac activity, processor 60 can analyze the time course of the behavioral event, abnormal brain activity (e.g., a seizure event), and abnormal cardiac activity (e.g., an arrhythmia event) to determine the cause of the behavioral event or at least eliminate possible causes. In the example shown in FIG. 11, processor 60 determines, based on the segments of interests of bioelectrical brain signal 76 and cardiac signal 164, whether the seizure activity within bioelectrical brain signal 76 and the arrhythmia activity within cardiac signal 164 began at substantially the same time (180), such as within less than a threshold range of each other. The threshold may not be specific as to whether the seizure activity or the arrhythmia activity occurred first, but whether they occurred within a particular time range, such as about 0.01 seconds to about 2 seconds of each other.

For example, processor 60 may determine whether segment 166 of bioelectrical brain signal 76 began at substantially the same time as segment 170 of cardiac signal 164. In examples in which the seizure activity and the arrhythmia activity began at substantially the same time, processor 60 (or the user) may determine that the behavioral event was related to (e.g., caused by) either the abnormal cardiac activity, e.g., the arrhythmia, or the abnormal brain activity, e.g., the seizure, or both (182).

If processor 60 determines that the seizure activity and the arrhythmia activity did not begin at substantially the same time, the user determines whether the seizure activity within bioelectrical brain signal 76 began prior to the arrhythmia activity within cardiac signal 164 (184). In examples in which processor 60 determines that the seizure activity began prior to the arrhythmia activity, processor 60 may determine that the behavioral event was related to (e.g., caused by) the seizure activity and not caused by the arrhythmia (186). In some examples, processor 60 may also determine that the arrhythmia was caused by the seizure activity. As an example, in the example illustrated in FIG. 10, processor 60 may determine whether segment 166 of bioelectrical brain signal 76 began before segment 170 of cardiac signal 164. In the example illustrated in FIG. 10, processor 60 determines that the abnormal brain activity began before the abnormal cardiac activity, e.g., segment 166 of bioelectrical brain signal 76 began before segment 170 of cardiac signal 164. Consequently, processor 60 determines that the fall illustrated by segment 165 of patient motion signal 78 and patient posture indicators 80B, 80C was related to (e.g., caused by) the abnormal brain activity (e.g., the brain activity indicative of a seizure), instead of the abnormal cardiac activity (e.g., the cardiac activity indicative of arrhythmia).

In examples in which processor 60 determines that the seizure activity and the arrhythmia did not begin at substantially the same time and that the seizure activity did not occur prior to the arrhythmia, processor 60 can determine that the arrhythmia occurred prior to the seizure activity (188). In these examples, processor 60 may determine that the behavioral event was related to (e.g., caused by) the arrhythmia and not caused by the seizure (190). In some examples, processor 60 may also determine that the seizure was caused by the arrhythmia.

In other examples, a user can manually make the determination of the time course of the behavioral event, abnormal brain activity, and abnormal cardiac activity to determine the cause of the behavioral event by observing graphical user interface 162. For example, the user may view graphical user interface 162 illustrated in FIG. 10 and determine whether segment 166 of bioelectrical brain signal 76 began at substantially the same time as segment 170 of cardiac signal 164. In examples in which the seizure activity and the arrhythmia activity began at substantially the same time, processor 60 (or the user) may determine that the behavioral event was caused by either the abnormal cardiac activity, e.g., the arrhythmia, or the abnormal brain activity, e.g., the seizure, or both (182).

Figure 12:
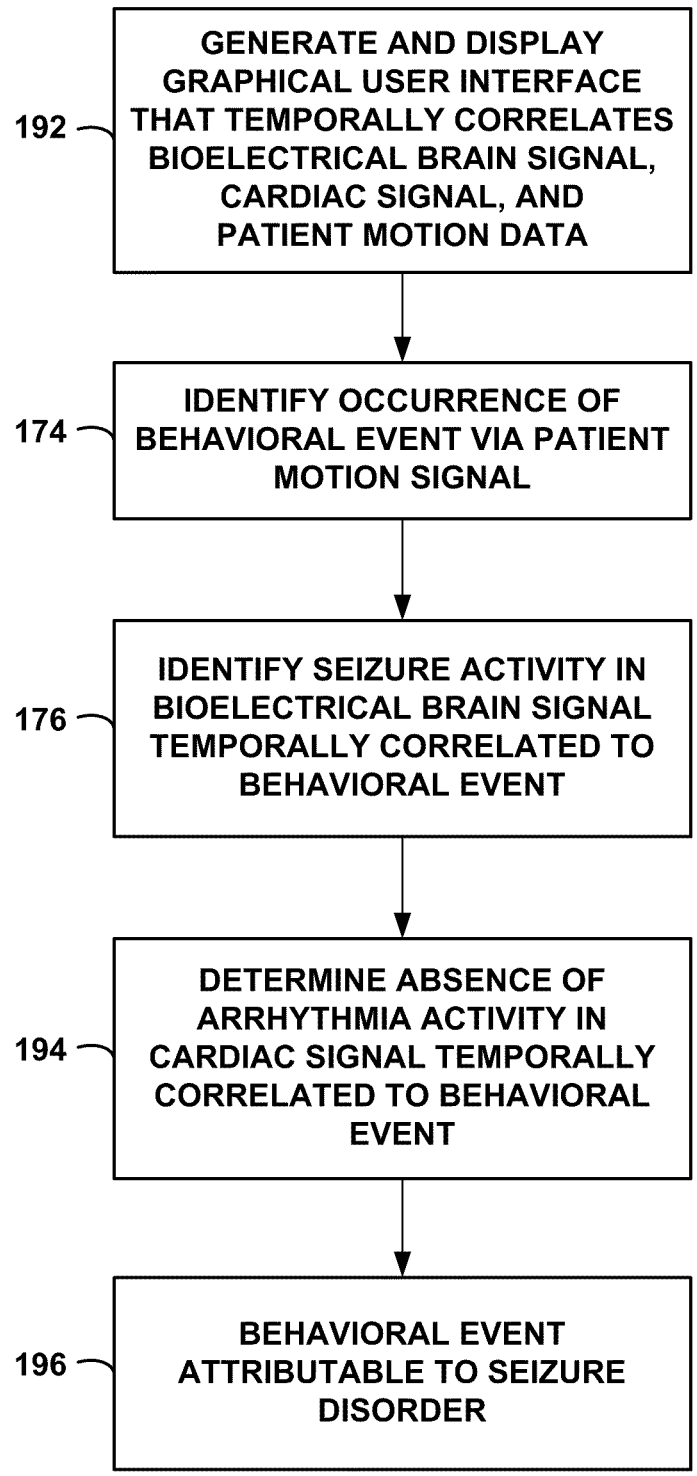
FIG. 12 is a flow diagram illustrating an example technique that may be used to determine that a behavioral event was caused by a seizure.

FIG. 12 is a flow diagram illustrating a technique for determining that a behavioral event was caused by a seizure-related condition, e.g., epilepsy. While FIG. 12 is described as being performed by processor 60 of programmer 14, in other examples, a processor of another device can automatically perform any part of the technique shown in FIG. 12 alone or with the aid of a user.

Processor 60 of programmer 14, upon receiving bioelectrical brain signal 76, cardiac signal 164, and signal 78 indicative of patient motion from a device (e.g., IMD 16), generates a graphical user interface and displays graphical user interface on a display of user interface 66 of programmer 14 in a manner that illustrates a temporal correlation between the physiological data, as discussed with respect to FIG. 11 (192). A user may view the graphical user interface and determine activity within patient motion signal 78 or a patient posture indicator 80 that is indicative of a particular behavioral event of patient 12. The user may, via user interface 66, provide input to programmer 14 identifying the occurrence of the behavioral event. For example, in response to a prompt generated by processor 60, the user may mark or highlight the segment of patient motion signal 78 or one or more patient posture indicators 80 that indicate that patient 12 underwent a fall event. Processor 60 can then identify the occurrence of a behavioral event based on patient motion signal 78 or, more indirectly, based on a patient posture indicator 80, which itself is based on patient motion signal 78 (174). For example, the user may determine that a particular segment of patient motion signal 78 or one or more patient posture indicators 80 indicates that patient 12 underwent a fall event.

Processor 60 automatically determines the segments of bioelectrical brain signal 76 and cardiac signal 164 that temporally correspond to the segment of patient motion signal 78 that illustrates the behavioral event. Processor 60 can update the graphical user interface 67 presented via user interface 66 to visually indicate the segments of bioelectrical brain signal 76 and cardiac signal 164 that temporally correspond to the segment of patient motion signal 78 that illustrates the behavioral event. For example, processor 60 can generate a marker that identifies the corresponding segments of bioelectrical brain signal 76 and cardiac signal 164 and display the marker in the graphical user interface. In other examples, the user visually ascertains the segments of bioelectrical brain signal 76 and cardiac signal 164 that temporally correspond to the segment of patient motion signal 78 that illustrates the behavioral event without the aid of processor 60.

Processor 60 determines whether the segment of bioelectrical brain signal 76 temporally correlated to the behavioral event detected based on patient motion signal 78 or patient posture indicators 80 is indicative of a seizure event. The segment of bioelectrical brain signal 76 that temporally corresponds to the behavioral event may include a biomarker or otherwise illustrate abnormal activity that occurred within brain 28 of patient 12 that indicates that patient 12 underwent a seizure during a similar time period in which the behavioral event occurred. Processor 60 can implement any suitable algorithm for determining whether the segment of bioelectrical brain signal 76 includes the activity indicative of seizure activity, such as the seizure detection algorithms described above. If processor 60 determines the segment of bioelectrical brain signal 76 is indicative of a seizure event, processor 60 identifies the activity within the segment of bioelectrical brain signal 76 that is indicative of seizure activity within brain 28 of patient 12 (176).

Processor 60 also determines whether the segment of cardiac signal 164 that temporally corresponds to the behavioral event is indicative of an arrhythmia within the heart of patient 12. Processor 60 can determine whether the segment of cardiac signal 164 is indicative of arrhythmia using any suitable arrhythmia detection technique. An arrhythmia event or episode, whether the event or episode is a bradycardia or tachycardia event or episode, may be determined, e.g., based on a duration of a cardiac cycle. A cardiac cycle duration may be, for example, measured between successive R-waves or P-waves of the EGM or ECG signal. This duration may also be referred to as an R-R or P-P interval.

In the example illustrated in FIG. 12, processor 60 determines there is an absence of arrhythmia activity in the segment of cardiac signal 164 that temporally corresponds to the behavioral event (194). That is, processor 60 may determine that the segment of cardiac signal 164 that temporally corresponds to the behavioral event, indicates a normal sinus rhythm of the heart of patient 12. Processor 60 may, in some examples, update the graphical user interface presented to a user, such as by generating a marker that identifies the segment of interest of cardiac signal 164 to a user, e.g., processor 60 may highlight the segment or otherwise mark the segment. Based on determining that the segment of bioelectrical brain signal 76 that temporally corresponds to the behavioral event indicates seizure activity and that the segment of cardiac signal 164 that temporally corresponds to the behavioral event does not include activity indicative of an arrhythmia, processor 60 may determine that the behavioral event was caused by a seizure disorder of patient 12 (196). Processor 60 may generate an indication, e.g., an alert, in order to communicate to a user via graphical user interface 67 that the behavioral event was caused by a seizure disorder of patient 12. In some examples, processor 60 can also transmit the indication to a remote user (e.g., a remote database or a remote clinician's office), e.g., via a network. In other examples, a user may manually make the determination that the behavioral event was caused by a seizure disorder of patient 12, e.g., by viewing the segment of patient data associated with the behavioral event on graphical user interface 67. The user can provide user input indicating the determination that the behavioral event was caused by a seizure disorder of patient 12, e.g., via user interface 66.

Figure 13:
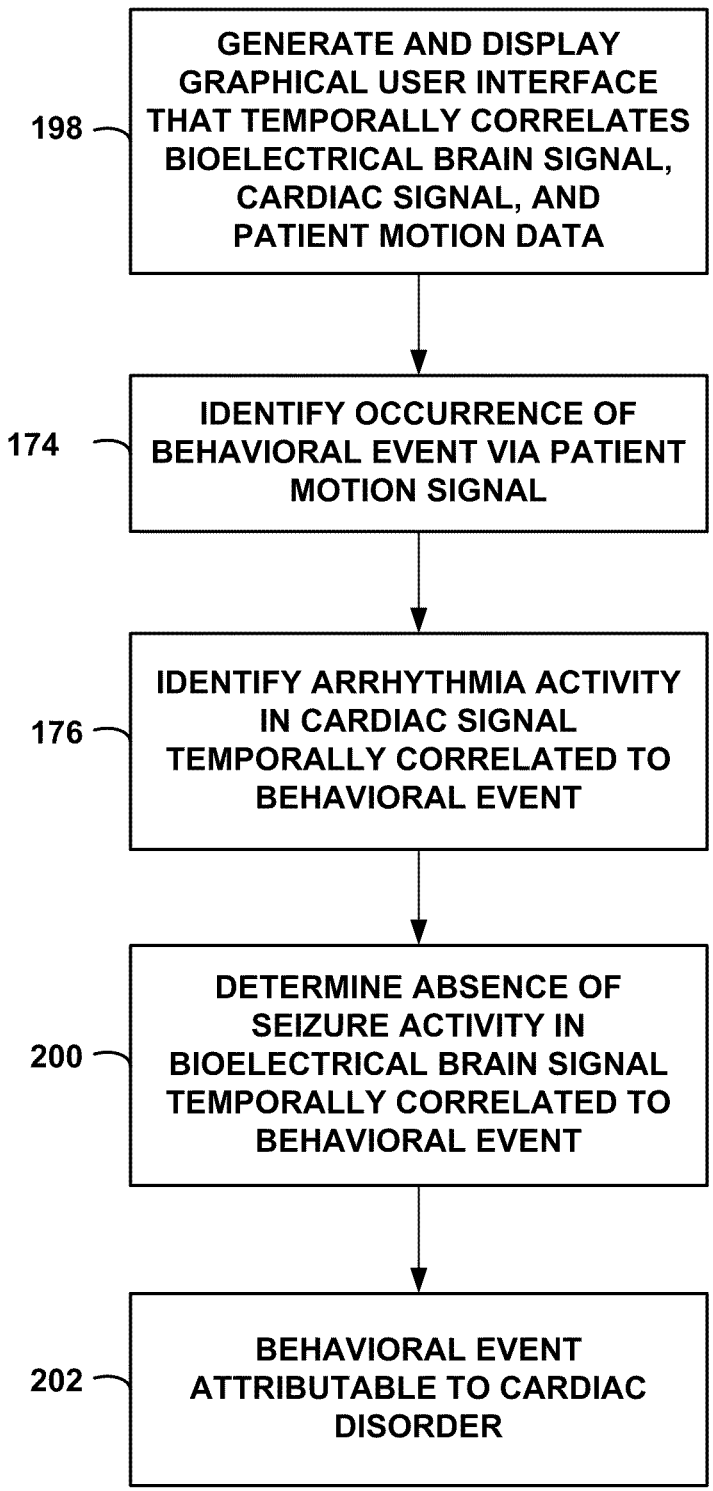
FIG. 13 is a flow diagram illustrating an example technique that may be used to determine that a behavioral event was caused by a cardiac event or episode.

FIG. 13 is a flow diagram illustrating a technique for determining that a behavioral event (e.g., a fall event) was caused by a cardiac-related condition, e.g., an arrhythmia. While FIG. 13 is described as being performed by processor 60 of programmer 14, in other examples, a processor of another device can automatically perform any part of the technique shown in FIG. 13 alone or with the aid of a user.

Processor 60 of programmer 14, upon receiving bioelectrical brain signal 76, cardiac signal 164, and signal 78 indicative of patient motion from a device (e.g., IMD 16), generates a graphical user interface and displays the graphical user interface on a display of user interface 66 of programmer 14 in a manner that illustrates a temporal correlation between the physiological data, as discussed with respect to FIG. 11 (198). As with the technique shown in FIG. 12, processor 60 identifies an occurrence of a behavioral event based on patient motion signal 76, e.g., based on patient input identifying activity within patient motion signal 78 or a patient posture indicator 80 that is indicative of a particular behavioral event of patient 12 (174).

In addition, as discussed with respect to FIG. 12, processor 60 determines whether a segment of cardiac signal 164 that temporally corresponds to the behavioral event is indicative of an arrhythmia within the heart of patient 12. If processor 60 determines that the segment of cardiac signal 164 that temporally corresponds to the behavioral event is indicative of an arrhythmia within the heart of patient 12, processor 60 identifies the portion of the cardiac signal 164 indicating the arrhythmia (178).

Processor 60 also determines whether the segment of bioelectrical brain signal 76 temporally correlated to the behavioral event detected based on patient motion signal 78 or patient posture indicators 80 is indicative of a seizure event. The segment of bioelectrical brain signal 76 that temporally corresponds to the behavioral event may include a biomarker or otherwise illustrate abnormal activity that occurred within brain 28 of patient 12 that indicates that patient 12 underwent a seizure during a similar time period in which the behavioral event occurred. Processor 60 can implement any suitable algorithm for determining whether the segment of bioelectrical brain signal 76 includes the activity indicative of seizure activity, such as the seizure detection algorithms described above.

In the example illustrated in FIG. 13, processor 60 determines there is an absence of seizure activity in the segment of bioelectrical brain signal 76 that temporally corresponds to the behavioral event (200). That is, processor 60 may determine that the segment of bioelectrical brain signal 76 that temporally corresponds to the behavioral event indicates normal activity within brain 28 of patient 12. Processor 60 may, in some examples, update the user interface to illustrate the segment of interest of bioelectrical brain signal 76, e.g., by generating a marker that identifies the segment of interest of bioelectrical brain signal 76. For example, processor 60 may highlight the segment or otherwise mark the segment.

Based on determining that the segment of cardiac signal 164 that temporally corresponds to the behavioral event indicates arrhythmia activity and that the segment of bioelectrical brain signal 76 that temporally corresponds to the behavioral event does not include activity indicative of seizure, processor 60 may determine that the behavioral event was caused by a cardiac disorder of patient 12 (202). Processor 60 may generate an indicator, e.g., an alert, in order to communicate to a user via graphical user interface 67 that the behavioral event was caused by a cardiac disorder of patient 12. In some examples, processor 60 can also transmit the indication to a remote user (e.g., a remote database or a remote clinician's office), e.g., via a network. In other examples, a user may manually make the determination that the behavioral event was caused by a cardiac disorder of patient 12, e.g., by viewing the segment of patient data associated with the behavioral event on graphical user interface 67. The user can provide user input indicating the determination that the behavioral event was caused by a cardiac disorder of patient 12, e.g., via user interface 66.

As previously described, in some examples, therapy system 10 can include one or more activity sensors in addition to or instead of activity sensors 25, 36 (FIGS. 1 and 2). FIG. 14 is a diagram illustrating therapy system 10 that includes additional activity sensors. In the example illustrated in FIG. 14, therapy system 10 includes implantable activity sensor 204 and external activity sensors 206, 208, and 210, in addition to or instead of activity sensors 25 and 36 (FIGS. 1 and 2).

Activity sensors 204, 206, 208, and 210 may be sensors that generate signals indicative of patient motion. For example, activity sensors 204, 206, 208, and 210 may be sensors that generate a signal related to the change in acceleration of patient 12 in multiple directions, e.g., in the x-axis direction, the y-axis direction, and the z-axis direction. In other examples, activity sensors 204, 206, 208, and 210 may include one or more gyroscopes, pressure transducers, piezoelectric crystals, or other sensors that generate a signal indicative of patient activity.

In the example illustrated in FIG. 14, activity sensor 204 is an implantable sensor that is separate from, e.g., not integral with, IMD 16. Although activity sensor 204 in FIG.

14 is implanted within the torso of patient 12, in other examples, activity sensor 204 may be implanted in any suitable location within the body of patient 12. For example, in some examples, activity sensor 204 may be implanted within a limb of patient 12, e.g., an arm or leg.

In some examples, activity sensors 204, 206, 208, and 210 may be configured to wirelessly communicate with IMD 16. Alternatively or additionally, activity sensors 204, 206, 208, and 210 may be configured to wirelessly communicate with programmer 14. In this way, activity sensors 204, 206, 208, and 210 may transfer signals that are indicative of patient motion to IMD 16 and/or programmer 14. In some examples, the signals are displayed on a user interface, e.g., user interface 66 of programmer 14, that temporally correlates the signals to bioelectrical brain signals of patient 12 and, in some cases, cardiac signals of patient 12, e.g., as illustrated by user interface 66 in FIGS. 5 and 9. In addition, in some examples, processor 60 of programmer 14 generates and displays one or more patient state indicators based at least in part on the signals generated by one or more of activity sensors 204, 206, 208, and 210.

Activity sensors 206, 208, and 210 are placed externally on the body of patient 12, e.g., are not implanted within patient 12. For example, in the example illustrated in FIG. 14, activity sensor 206 is positioned on the waist of patient 12, activity sensor 208 is positioned on the leg of patient 12, and activity sensor 210 is positioned on a wrist of patient 12. Activity sensor 206, 208, and 210 may be attached to patient 12 via any suitable mechanism. For example, activity sensors 206, 208, and 210 may be attached to patient 12 via an elastic band that couples the activity sensor to patient 12.

In some examples, an activity sensor such as activity sensor 206 that indicates motion of a limb of patient 12 may provide a more accurate indication of the motion of patient 12 in comparison to an activity sensor implanted within the head or torso of patient 12, e.g., activity sensors 25, 36, and 204. For example, patient 12 may exhibit a high amount of motion in a limb, e.g., an arm, during a seizure that may be more accurately measured by an activity sensor attached to the limb in comparison to an activity sensor within the head or torso.

As described above, in some examples, the graphical user interface that includes a bioelectrical brain signal of a patient and a patient posture indicator that provides a graphical representation of a posture state of the patient at a particular point in time can be useful for determining a characteristic of a bioelectrical brain signal that is indicative of a seizure event. In other examples, the graphical user interface can be used to determine a characteristic of a bioelectrical brain signal that is indicative of another type of patient state or for otherwise evaluating a patient condition. For example, the patient state can be a movement state (e.g., a state in which patient 12 is moving, attempting to move, or intending on moving). A user can identify a characteristic of a bioelectrical brain signal that is temporally correlated with a patient posture indicator that indicates patient movement (e.g., a change in patient posture states). This characteristic of the bioelectrical brain signal can then be used to later detect the patient movement state to, e.g., control therapy delivery to patient 12 or to evaluate the patient condition.

In other examples, patient 12 may suffer from a movement disorder or another neurodegenerative impairment that includes symptoms such as, for example, muscle control impairment, motion impairment or other movement problems, such as rigidity, bradykinesia, rhythmic hyperkinesia, nonrhythmic hyperkinesia, and akinesia. In some cases, the movement disorder may be a symptom of Parkinson's disease or, in other examples, the movement disorder may be attributable to other patient conditions. A graphical user interface that temporally correlates a bioelectrical brain signal and a signal indicative of patient motion may be useful for evaluating the severity of movement disorders or neurodegenerative impairments that include symptoms associated with patient movement, e.g., to generate a therapy regimen for the patient.

As an example, patient 12 may be afflicted with a movement disorder that includes symptoms associated with Parkinson's disease. Depending upon the quantity and severity of symptoms experienced by patient 12 at a particular point in time, patient 12 may be in either an off-state or an on-state of the movement disorder. That is, during periods of time in which patient 12 experiences a relatively large quantity and/or relatively severe or frequent symptoms associated with the movement disorder, patient 12 may be said to be in an off-state (also referred to as an off-time). During periods of time in which patient 12 experiences a relatively small quantity and/or relatively mild symptoms associated with the movement disorder, patient 12 may be said to be in an on-state (also referred to as an on-time). In some examples, the transition from an off-state to an on-state may be initiated by delivery of therapy, e.g., electrical stimulation therapy or delivery of a drug to patient 12.

A graphical user interface that temporally correlates a bioelectrical brain signal and a patient motion signal, e.g., graphical user interface 67 (FIG. 5), may be useful for assessing a movement disorder of patient 12. For example, in some examples, a user can view a plurality of patient posture indicators that are indicative of the motion of patient 12 and determine whether patient 12 is in an off-state or an on-state of the movement disorder. As an example, patient 12 may suffer from akinesia, e.g., inability to initiate movement, that results from the movement disorder. During periods of time in which patient 12 is in an off-state, patient 12 may suffer from relatively severe akinesia. A user can view patient posture indicators on a graphical user interface and identify time periods in which patient 12 may have experienced relatively severe akinesia, e.g., by identifying one or more particular patient posture indicators that are generally representative of lack of movement of patient 12. Similarly, during periods of time in which patient 12 is in an on-state, patient 12 may suffer from relatively mild akinesia. A user can view patient posture indicators on a graphical user interface and identify time periods in which patient 12 may have experienced relatively mild akinesia, e.g., by identifying one or more particular patient posture indicators that are generally representative of movement of patient 12. In some examples, a user may provide input to the graphical user interface indicating particular segments of patient data that are indicative of an off-state, particular segments of patient data that are indicative of an on-state, and particular segments of patient data that are indicative of a transition between an on-state and an off-state based on identifying one or more particular patient posture indicators.

In some examples, tissue within the brain of patient 12 may exhibit a different pattern of electrical activity during time periods in which patient 12 is in an off-state, e.g., during time periods in which patient 12 is experiencing relatively severe symptoms of a movement disorder, in comparison to time periods in which patient 12 is in an on-state. Thus, in some examples, a graphical user interface that temporally correlates a signal indicative of patient motion with a bioelectrical brain signal may be useful for identifying patterns of motion of patient 12 that are indicative of varying degrees of symptoms associated with a movement disorder, e.g., via patient posture indicators, and subsequently identifying one or more bioelectrical brain signal characteristics associated with an off-state, an on-state, a transition from an off-state to an on-state, or a transition from an on-state to an off-state.

In some examples, the power level within a selected frequency band of the bioelectrical brain signal may be particularly indicative of activity within the brain of patient 12 that is associated with a particular disorder. For example, it is believed that abnormal activity within a beta band (e.g., about 8 hertz (Hz) to about 30 Hz or about 16 Hz to about 30 Hz) of a bioelectrical brain signal is indicative of brain activity associated with a movement disorder, and may also be revealing of a target tissue site for therapy delivery to manage the patient condition. Therefore, in some examples, the one or more bioelectrical brain signal characteristics can include a power level within a beta band of a bioelectrical brain signal.

In general, a spectrogram may provide a visual illustration of the power level within a range of frequency bands of a bioelectrical brain signal. In some examples, processor 60 of programmer 14 or another device can generate a spectrogram and include the spectrogram in a graphical user interface that also includes a representation of a bioelectrical brain signal and one or more patient posture indicators that are temporally correlated to the bioelectrical brain signal. Processor 60 can determine the power of a sensed bioelectrical brain signal using any suitable technique. For example, processor 60 may determine an overall power level of a sensed bioelectrical brain signal based on the total power level of a swept spectrum of the brain signal. To generate the swept spectrum, processor 60 may control a sensing module to tune to consecutive frequency bands over time, and processor 60 may assemble a pseudo-spectrogram of the sensed bioelectrical brain signal based on the power level in each of the extracted frequency bands. The pseudo-spectrogram may be indicative of the energy of the frequency content of the bioelectrical brain signal within a particular window of time. Processor 60 may generate and store the pseudo-spectrograms for all of the sensed bioelectrical brain signal data or for particular segments of the sensed bioelectrical brain signal data, e.g., segments of data that are indicative of a particular behavioral event of interest of patient 12.

Upon identification by a user of a particular patient data segment of interest, e.g., a particular segment in which patient 12 was in an off-state, an on-state, or a transition between an off-state and an on-state, processor 60 can update the graphical user interface to display the pseudo-spectrogram that temporally corresponds to the segment of patient data and is derived from the segment of the bioelectrical brain signal of the patient data. For example, a user may provide input indicating a particular patient posture indicator that represents a symptom associated with a movement disorder, e.g., akinesia. Processor 60 may identify other segments of patient data, e.g., segments of a bioelectrical brain signal, that are temporally correlated to the particular patient posture indicator. Processor 60 may mark the entire segment of patient data, e.g., by highlighting the temporally correlated portions of the bioelectrical brain signal and the patient posture indicator on the graphical user interface.

In addition, processor 60 may also access and display on the graphical user interface the corresponding pseudo-spectrogram, e.g., the pseudo-spectrogram derived from the segment of interest of the bioelectrical brain signal. For example, upon viewing the segment of bioelectrical brain signal that is temporally correlated to the patient posture indicator of interest, e.g., based on the segment of the bioelectrical brain signal that is highlighted on the graphical user interface, the user may click on the segment of the bioelectrical brain signal and the processor may display the pseudo-spectrogram that corresponds to the segment of the bioelectrical brain signal.

The user can view the pseudo-spectrogram associated with the particular patient posture indicator or indicators of interest via the graphical user interface. The user may then identify particular patterns or relationships associated with the pseudo-spectrograms for one or more particular periods of time. For example, the user may determine that spectrograms associated with an off-state exhibit different features than spectrograms associated with an on-state of patient 12. As an example, the user may determine that, during an off-state, a particular region of the brain of patient 12 in which the sensing electrodes are located exhibits a relatively high beta band power level based on viewing the pseudo-spectrogram associated with an off-state of patient 12. The user, e.g., a clinician, may determine that the beta band level determined based on the segment of the bioelectrical brain signal corresponding to the off-state is a suitable biomarker for the off-state. The biomarker can be used to, for example, control automatic detection of the off-state by IMD 16 or another device, e.g., to control therapy delivery to patient 12.

Additionally, the user may identify via the graphical user interface other types of patterns within the pseudo-spectrograms associated with off-states, on-states, or transitions between off-states and on-states of patient 12 that may be useful in more effectively treating the movement disorder of patient 12. Additionally or alternatively, the user may be able to determine, based on the data displayed on the graphical user interface, the amount (e.g., a percentage) of time that patient 12 was in off-states or on-states during a particular period of time, e.g., over the course of a day, month, or year. This may be useful for, e.g., quantifying the effectiveness of therapy delivered to patient 12, evaluating the severity of the patient's movement disorder, and/or modifying parameters of therapy to more effectively treat the movement disorder of patient 12.

In general, the graphical user interfaces described herein are useful for presenting patient information for any suitable patient state. As another example, the patient state can be a mood state (e.g., a depressed state or an anxious state) and a user can identify a characteristic of a bioelectrical brain signal that is temporally correlated with a patient posture indicator that indicates patient movement associated with the patient mood state. For example, if patient 12 has obsessive compulsive disorder, a plurality of patient posture indicators can indicate a compulsive motor activity. The user can then identify a characteristic of a bioelectrical brain signal that temporally correlate with (e.g., precedes or occurs at substantially the same time as) the compulsive motor activity. This bioelectrical brain signal characteristic can then be stored and used to detect the compulsive motor activity to, e.g., control therapy delivery to patient 12 or to evaluate the patient condition.

As one example, a patient may have a compulsion to turn a light switch on and off a particular number of consecutive times during a particular activity, e.g., before leaving a room. One or more implanted or external patient motion sensors may generate a signal indicative of the motion of patient 12 associated with turning the compulsive act, which, in this case, includes turning the light switch on and off, e.g., indicative of the motion of an arm of patient 12. A user interface may generate one or more patient posture indicators that are indicative of the motion of patient 12 in turning the light switch on and off based on the signals generated by the patient motion sensors, and temporally correlate the patient posture indicators with a bioelectrical brain signal of patient 12.

For example, the user interface may include a first patient posture indicator that represents the motion of patient 12 in turning the light switch on, e.g., moving the light switch up, and a second patient posture indicator that represents the motion of patient 12 in turning the light switch off, e.g., moving the light switch down. The patient posture indicator can illustrate the entire body of patient 12 or a part of the body of patient 12, e.g., the patient's hand or arm. In other examples, the user interface may include only one patient posture indicator representative of both turning the light switch on and turning the light switch off, e.g., representative of the entire compulsive activity. The user interface may display the patient posture indicators temporally correlated with the bioelectrical brain signal of patient 12 sensed during the same time period in which patient 12 performed the compulsive activity. In this way, a user may identify particular characteristics of the bioelectrical brain signal that temporally correlate with the compulsive motion of patient 12 in turning the light switch on and off via the user interface.

If patient 12 has a tic disorder, patient posture indicators 80 can indicate the occurrence of a tic. The one or more bioelectrical brain signal characteristics that are temporally correlated with and indicative of the tics can be determined and stored for patient monitoring or therapy control purposes. If patient 12 is depressed, a lack of patient movement, as indicated by the patient posture indicators, can be used to identify the one or more bioelectrical brain signal characteristics that are temporally correlated with and indicative of the depressed patient mood state. Other types of mood states and patient states are contemplated.

The characteristics of the bioelectrical brain signal that are indicative of a particular patient state can generally be used to generate a classification boundary using a supervised machine learning technique, as described above with respect to seizure disorders. In this way, the graphical user interface that includes a bioelectrical brain signal of a patient and one or more patient posture indicators can be used to program IMD 16 or another device to automatically detect a particular patient state. Patient state detection can be used for patient monitoring and evaluation, generating patient notification, therapy control, or and the like.

While examples described herein discuss medical devices that provide therapy to a patient, the disclosed systems and methods may also be employed with implantable or external devices that are used solely for monitoring and diagnostic purposes, e.g., loop recorders. Additionally, other types of sensors can be utilized to record and generate other types of physiological signals that can be displayed on the graphical user interface, in addition to the example signals described herein.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 40 of IMD 16 and/or processor 60 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
   displaying, with a display device, a bioelectrical brain signal of a patient;
   generating and displaying, with the display device, a patient posture indicator that is temporally correlated with a segment of the bioelectrical brain signal indicative of a seizure event of the patient, wherein the patient posture indicator comprises a graphical representation of at least a portion of a body of the patient during the seizure event, and wherein displaying the bioelectrical brain signal and displaying the patient posture indicator comprises displaying a graphical user interface that includes the bioelectrical brain signal and the patient posture indicator;
   displaying, with the display device, a representation of a temporal correlation between the bioelectrical brain signal of a patient and a signal indicative of motion of the patient; and
   displaying, with the display device, a sliding window that highlights the segment of the bioelectrical brain signal indicative of the seizure event of the patient and a portion of the signal indicative of motion of the patient that were sensed during a common time period.

2. The method of claim 1, wherein generating the patient posture indicator comprises:
   determining a posture state of the patient based on a segment of the signal indicative of motion of the patient temporally correlated with the segment of the bioelectrical brain signal indicative of the seizure event of the patient;

selecting the patient posture indicator based on the determined posture state; and displaying the selected patient posture indicator.

3. The method of claim 2, wherein the patient posture state comprises a posture state associated with at least one of a fall, a sitting upright after a fall, standing upright after a fall, a tonic seizure component, a clonic seizure component, a tonic-clonic seizure, convulsive activity, nocturnal seizure activity, a dystonic-type movement, a compulsive motor activity, or a tic behavior.

4. The method of claim 1, wherein displaying the patient posture indicator comprises displaying a plurality of patient posture indicators, each of the plurality of patient posture indicators being temporally correlated with a respective segment of a plurality of segments of the bioelectrical brain signal of the patient, the plurality of segments of the bioelectrical brain signal comprising the segment of the bioelectrical brain signal indicative of the seizure event of the patient.

5. The method of claim 4, wherein displaying the plurality of patient posture indicators comprises displaying one patient posture indicator of the plurality of patient posture indicators at a time.

6. The method of claim 1, further comprising displaying, with the display device, a marker that identifies a portion of the bioelectrical brain signal temporally correlated with a change in a posture state of the patient.

7. The method of claim 1, further comprising displaying, with the display device, a signal indicative of cardiac activity of the patient that is temporally correlated with the bioelectrical brain signal of the patient and the patient posture indicator.

8. The method of claim 1, further comprising receiving, with the display device, user input selecting a type of patient posture indicator, wherein displaying, with the display device, the bioelectrical brain signal of a patient comprises displaying the bioelectrical brain signal that temporally correlates to the selected type of patient posture indicator.

9. The method of claim 1, further comprising receiving, via the display device, user input characterizing the seizure event of the patient after displaying the bioelectrical brain signal and the patient posture indicator.

10. The method of claim 1, further comprising, with the display device, identifying the segment of the bioelectrical brain signal indicative of the seizure event of the patient by at least executing a seizure detection algorithm.

11. The method of claim 10, further comprising receiving, with the display device, user input modifying the seizure detection algorithm after displaying the bioelectrical brain signal and the patient posture indicator.

12. The method of claim 1, wherein the segment of the bioelectrical brain signal comprises a first segment of the bioelectrical brain signal, the method further comprising:

identifying, with the display device, a second segment of the bioelectrical brain signal indicative of the seizure event of the patient, wherein the second segment of the bioelectrical brain signal indicates that the seizure event is impending; and presenting, with the display device, a visual alert indicating that the seizure event is impending.

13. A system comprising:

a user interface; and a processor configured to generate and display, via the user interface, a graphical user interface comprising a bioelectrical brain signal of a patient, a patient posture indicator, a signal indicative of motion of the patient, and a sliding window, wherein the patient posture indicator is temporally correlated with a segment of the bioelectrical brain signal indicative of a seizure event of the patient, wherein the patient posture indicator comprises a graphical representation of at least a portion of a body of the patient during the seizure event, and wherein the sliding window highlights the segment of the bioelectrical brain signal indicative of the seizure event of the patient and a portion of the signal indicative of motion of the patient temporally correlated with the segment of the bioelectrical brain signal.

14. The system of claim 13, wherein the processor is configured to generate the patient posture indicator by at least determining a posture state of the patient based on a segment of the signal indicative of motion of the patient temporally correlated with the segment of the bioelectrical brain signal indicative of the seizure event of the patient, and selecting the patient posture indicator based on the determined posture state.

15. The system of claim 13, wherein the graphical user interface further comprises a plurality of patient posture indicators, each of the plurality of patient posture indicators being temporally correlated with a respective segment of a plurality of segments of the bioelectrical brain signal of the patient, the plurality of segments of the bioelectrical brain signal comprising the segment of the bioelectrical brain signal indicative of the seizure event of the patient.

16. The system of claim 13, wherein the graphical user interface further comprises a marker that identifies a portion of the bioelectrical brain signal temporally correlated with a change in a posture state of the patient.

17. The system of claim 13, further comprising a first sensor configured to generate the bioelectrical brain signal of the patient and a second sensor configured to generate the signal indicative of motion of the patient, wherein the processor is configured to generate the patient posture indicator based on the signal indicative of motion of the patient.

18. The system of claim 13, wherein the graphical user interface further comprises a signal indicative of cardiac activity of the patient that is temporally correlated with the bioelectrical brain signal of the patient and the patient posture indicator.

19. The system of claim 13, wherein the processor is configured to receive, via the user interface, user input selecting a type of patient posture indicator, wherein the bioelectrical brain signal temporally correlates to the selected type of patient posture indicator.

20. The system of claim 13, wherein the processor is further configured to receive, via the user interface, user input characterizing the seizure event of the patient after displaying the bioelectrical brain signal and the patient posture indicator.

21. The system of claim 13, wherein the segment of the bioelectrical brain signal comprises a first segment of the bioelectrical brain signal, and wherein the processor is further configured to:

identify a second segment of the bioelectrical brain signal indicative of the seizure event of the patient, wherein the second segment of the bioelectrical brain signal indicates that the seizure event is impending, and present, via the user interface, a visual alert indicating that the seizure event is impending.

22. A system comprising:

means for displaying a bioelectrical brain signal of a patient; and means for generating a patient posture indicator that is temporally correlated with a segment of the bioelectrical brain signal indicative of a seizure event of the patient, wherein the patient posture indicator comprises a graphical representation of at least a portion of a body of the patient during the seizure event, wherein the means for displaying displays a graphical user interface comprising the patient posture indicator, the bioelectrical brain signal, a signal indicative of motion of the patient, and a sliding window that highlights the segment of the bioelectrical brain signal indicative of the seizure event of the patient and a portion of the signal indicative of motion of the patient temporally correlated with the segment of the bioelectrical brain signal.

23. The system of claim 22, wherein the graphical user interface further comprises a signal indicative of cardiac activity of the patient that is temporally correlated with the bioelectrical brain signal of the patient and the patient posture indicator.

24. A non-transitory computer-readable medium comprising instructions that cause a programmable processor to:
display a bioelectrical brain signal of a patient;
generate and display a patient posture indicator that is temporally correlated with a segment of the bioelectrical brain signal indicative of a seizure event of the patient, wherein the patient posture indicator comprises a graphical representation of at least a portion of a body of the patient during the seizure event, and wherein the instructions cause the programmable processor to display the bioelectrical brain signal and the patient posture indicator by at least displaying a graphical user interface that includes the bioelectrical brain signal and the patient posture indicator; and
display a signal indicative of motion of the patient and a sliding window that highlights the segment of the bioelectrical brain signal indicative of the seizure event of the patient and a portion of the signal indicative of motion of the patient temporally correlated with the segment of the bioelectrical brain signal.

25. The non-transitory computer-readable medium of claim 24, further comprising instructions that cause the programmable processor to display a signal indicative of cardiac activity of the patient that is temporally correlated with the bioelectrical brain signal of the patient and the patient posture indicator.

* * * * *